United States Patent
Fujita et al.

(10) Patent No.: US 9,876,177 B2
(45) Date of Patent: Jan. 23, 2018

(54) THIADIAZOLE-BASED COMPOUND, LIGHT EMITTING ELEMENT COMPOUND, LIGHT EMITTING ELEMENT, LIGHT EMITTING DEVICE, AUTHENTICATION DEVICE, AND ELECTRONIC DEVICE

(75) Inventors: Tetsuji Fujita, Chino (JP); Hidetoshi Yamamoto, Suwa (JP)

(73) Assignee: SEIKO EPSON CORPORATION, Tokyo (JP)

(*) Notice: Subject to any disclaimer, the term of this patent is extended or adjusted under 35 U.S.C. 154(b) by 828 days.

(21) Appl. No.: 13/444,107

(22) Filed: Apr. 11, 2012

(65) Prior Publication Data
US 2012/0267615 A1    Oct. 25, 2012

(30) Foreign Application Priority Data

Apr. 12, 2011  (JP) .................. 2011-088559
Apr. 12, 2011  (JP) .................. 2011-088560
Apr. 12, 2011  (JP) .................. 2011-088562

(51) Int. Cl.
*C07D 513/04*    (2006.01)
*H01L 51/54*     (2006.01)
(Continued)

(52) U.S. Cl.
CPC ........ *H01L 51/0071* (2013.01); *C07D 513/04* (2013.01); *C09K 11/06* (2013.01);
(Continued)

(58) Field of Classification Search
None
See application file for complete search history.

(56) References Cited

U.S. PATENT DOCUMENTS 4,769,292 A    9/1988  Tana et al.
5,104,740 A    4/1992  Shinkai et al.
(Continued)

FOREIGN PATENT DOCUMENTS

CN    103187532 A    7/2013
EP    0 281 381 B1   7/1992
(Continued)

OTHER PUBLICATIONS

Jan. 22, 2015 Office Action issued in U.S. Appl. No. 13/564,384.
(Continued)

*Primary Examiner* — J. L. Yang
(74) *Attorney, Agent, or Firm* — Oliff PLC

(57) ABSTRACT

Provided is a thiadiazole compound with high efficiency and long life which emits light in a near-infrared region and represented by Formula (I).

[Chem. 1]

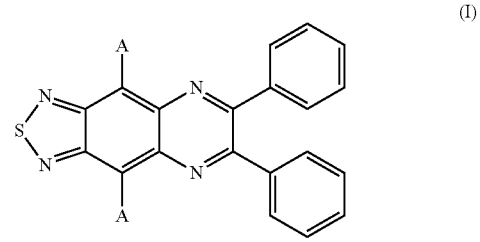

(I)

[In the Formula (I), As each independently represent an aryl group which may have a substituent or a diarylamino group.]

15 Claims, 7 Drawing Sheets

(51) Int. Cl.
  *H01L 51/00* (2006.01)
  *C09K 11/06* (2006.01)
  *H05B 33/14* (2006.01)

(52) U.S. Cl.
  CPC ...... *H01L 51/0054* (2013.01); *H01L 51/0058* (2013.01); *H01L 51/0059* (2013.01); *H01L 51/0061* (2013.01); *H05B 33/14* (2013.01); *C09K 2211/1007* (2013.01); *C09K 2211/1011* (2013.01); *C09K 2211/1014* (2013.01); *C09K 2211/1044* (2013.01); *C09K 2211/1051* (2013.01)

(56) References Cited

U.S. PATENT DOCUMENTS

| | | | |
|---|---|---|---|
| 5,294,869 | A | 3/1994 | Tang et al. |
| 5,449,564 | A | 9/1995 | Nishio et al. |
| 5,862,434 | A | 1/1999 | Yamakawa |
| 6,004,685 | A | 12/1999 | Antoniadis et al. |
| 6,680,131 | B1 | 1/2004 | Ishibashi et al. |
| 7,097,917 | B1 | 8/2006 | Fujita et al. |
| 7,632,579 | B2 | 12/2009 | Ise et al. |
| 7,714,099 | B2 | 5/2010 | Morishita et al. |
| 7,902,542 | B2 | 3/2011 | Haase et al. |
| 7,919,773 | B2 | 4/2011 | Kawakami et al. |
| 7,947,992 | B2 | 5/2011 | Yasukawa et al. |
| 7,960,912 | B2 | 6/2011 | Yasukawa et al. |
| 8,039,128 | B2 | 10/2011 | Watanabe et al. |
| 8,803,138 | B2 | 8/2014 | Fujita et al. |
| 9,067,952 | B2 | 6/2015 | Yamamoto et al. |
| 9,072,150 | B2 | 6/2015 | Fujita et al. |
| 9,159,932 | B2 | 10/2015 | Fujita et al. |
| 2002/0089560 | A1 | 7/2002 | Katayama et al. |
| 2003/0008172 | A1 | 1/2003 | Leclerc et al. |
| 2003/0027016 | A1* | 2/2003 | Ara et al. ................ 428/690 |
| 2004/0018382 | A1 | 1/2004 | Kinlen |
| 2005/0079381 | A1 | 4/2005 | Hamada et al. |
| 2005/0106415 | A1 | 5/2005 | Jarikov et al. |
| 2006/0063027 | A1 | 3/2006 | Vestweber et al. |
| 2006/0154105 | A1* | 7/2006 | Yamamoto et al. ........ 428/690 |
| 2007/0077453 | A1 | 4/2007 | Sano et al. |
| 2007/0254432 | A1* | 11/2007 | Yamazaki et al. ........ 438/253 |
| 2007/0285005 | A1 | 12/2007 | Itai |
| 2008/0061681 | A1 | 3/2008 | Thompson et al. |
| 2008/0067479 | A1 | 3/2008 | Kimura et al. |
| 2008/0125593 | A1 | 5/2008 | Kim et al. |
| 2008/0230123 | A1 | 9/2008 | Mitsui et al. |
| 2009/0079335 | A1 | 3/2009 | Mitsuya et al. |
| 2009/0091250 | A1 | 4/2009 | Yasukawa et al. |
| 2009/0115348 | A1 | 5/2009 | Yamazaki et al. |
| 2009/0243476 | A1 | 10/2009 | Nomura et al. |
| 2009/0261360 | A1 | 10/2009 | Yasukawa et al. |
| 2010/0108992 | A1* | 5/2010 | Ikeda ............... C09K 11/06 257/40 |
| 2010/0133434 | A1 | 6/2010 | Meng et al. |
| 2010/0155694 | A1 | 6/2010 | Miller et al. |
| 2010/0194807 | A1 | 8/2010 | Hirasawa et al. |
| 2010/0237338 | A1 | 9/2010 | Yamamoto et al. |
| 2010/0237990 | A1 | 9/2010 | Amano et al. |
| 2010/0244671 | A1 | 9/2010 | Nomura et al. |
| 2010/0244679 | A1 | 9/2010 | Fujita et al. |
| 2010/0252823 | A1 | 10/2010 | Kambe et al. |
| 2010/0317858 | A1 | 12/2010 | Konno |
| 2011/0058192 | A1 | 3/2011 | Hatanaka et al. |
| 2011/0087034 | A1 | 4/2011 | Miyata et al. |
| 2011/0127505 | A1* | 6/2011 | Nakamura ........ H01L 51/5088 257/40 |
| 2011/0253988 | A1 | 10/2011 | Molt et al. |
| 2011/0279020 | A1 | 11/2011 | Inoue et al. |
| 2011/0303901 | A1 | 12/2011 | Cheng et al. |
| 2012/0056213 | A1 | 3/2012 | Yamamoto et al. |
| 2012/0091923 | A1 | 4/2012 | Kastner-Jung et al. |
| 2012/0262057 | A1 | 10/2012 | Fujita et al. |
| 2012/0267615 | A1 | 10/2012 | Fujita et al. |
| 2013/0009909 | A1 | 1/2013 | Yamazaki et al. |
| 2013/0032791 | A1 | 2/2013 | Bazan et al. |
| 2013/0037784 | A1 | 2/2013 | Yamamoto et al. |
| 2013/0037785 | A1 | 2/2013 | Fujita et al. |
| 2013/0099209 | A1 | 4/2013 | Hartmann et al. |
| 2013/0168654 | A1 | 7/2013 | Fujita et al. |
| 2013/0221334 | A1 | 8/2013 | Yamamoto et al. |
| 2014/0332835 | A1 | 11/2014 | Fujita et al. |
| 2015/0236226 | A1 | 8/2015 | Fujita et al. |

FOREIGN PATENT DOCUMENTS

| | | |
|---|---|---|
| JP | A-63-264692 | 11/1988 |
| JP | A-2-255788 | 10/1990 |
| JP | A-3-791 | 1/1991 |
| JP | A-3-792 | 1/1991 |
| JP | A-3-162481 | 7/1991 |
| JP | A-3-177486 | 8/1991 |
| JP | A-5-32966 | 2/1993 |
| JP | A-5-214334 | 8/1993 |
| JP | A-5-258859 | 10/1993 |
| JP | A-6-73374 | 3/1994 |
| JP | A-6-93257 | 4/1994 |
| JP | A-6-136359 | 5/1994 |
| JP | A-6-145146 | 5/1994 |
| JP | A-6-240246 | 8/1994 |
| JP | H07-52375 A | 2/1995 |
| JP | H09-236965 A | 9/1997 |
| JP | A-10-330295 | 12/1998 |
| JP | H11-179895 A | 7/1999 |
| JP | A-11-233261 | 8/1999 |
| JP | H11-217776 A | 8/1999 |
| JP | A-2000-91073 | 3/2000 |
| JP | 2001-097949 A | 4/2001 |
| JP | A-2001-110570 | 4/2001 |
| JP | 2001-270585 A | 10/2001 |
| JP | A-2002-097465 | 4/2002 |
| JP | A-2003-55652 | 2/2003 |
| JP | 2003-109760 A | 4/2003 |
| JP | 2004-002297 A | 1/2004 |
| JP | A-2005-63938 | 3/2005 |
| JP | 2005-531552 A | 10/2005 |
| JP | 2006-045398 A | 2/2006 |
| JP | 2006-511939 A | 4/2006 |
| JP | 2007-000769 A | 1/2007 |
| JP | A-2007-115626 | 5/2007 |
| JP | 2008-069100 A | 3/2008 |
| JP | 2008-133277 A | 6/2008 |
| JP | 2008-162921 A | 7/2008 |
| JP | 2008-546185 A | 12/2008 |
| JP | A-2009-016693 | 1/2009 |
| JP | 2009-049094 A | 3/2009 |
| JP | 2009-256343 A | 11/2009 |
| JP | 2009-272144 A | 11/2009 |
| JP | 2010-147179 A | 7/2010 |
| JP | 2010-179544 A | 8/2010 |
| JP | 2010-245211 A | 10/2010 |
| JP | 2010-254674 A | 11/2010 |
| JP | 2011-508368 A | 3/2011 |
| JP | 2011-073432 A | 4/2011 |
| JP | 2011-134810 A | 7/2011 |
| WO | 2003-095445 A1 | 11/2003 |
| WO | 2004-058911 A2 | 7/2004 |
| WO | 2006-127315 A2 | 11/2006 |
| WO | WO 2008/069322 A1 | 6/2008 |
| WO | 2008-094187 A2 | 8/2008 |
| WO | 2009075741 A1 | 6/2009 |

OTHER PUBLICATIONS

Jeff D. Debad et al., Dibenzotetraphenylperiflanthene: Synthesis, Photophysical Properties, and Electrogenerated Chemiluminescence, *Journal of American Chemical Society*, 1996, vol. 118, pp. 2374-2379.

Mitsuo Kawabe, Electroluminescence of Green Light Region in Doped Anthracene, *Japanese Journal of Applied Physics*, 1971, vol. 10, pp. 527-527, Japan.

Apr. 22, 2015 Office Action issued in U.S. Appl. No. 13/773,033.

(56) References Cited

OTHER PUBLICATIONS

U.S. Appl. No. 14/693,484, filed Apr. 22, 2015 in the name of Yamamoto et al.
U.S. Appl. No. 14/700,751, filed Apr. 30, 2015 in the name of Fujita et al.
Qian, G. et al., "Synthesis and Application of Thiadiazoloquinoxaline-Containing Chromophores as Dopants for Efficient Near-Infrared Organic Light-Emitting Diodes," *J. Phys. Chem. C*, 2009, pp. 1589-1595, vol. 113.
Aug. 21, 2014 Office Action issued in U.S. Appl. No. 13/564,376.
Du et al., "Efficient Non-doped Near Infrared Organic Light-Emitting Devices Based on Fluorophores with Aggregation-Induced Emission Enhancement" *Chemistry of Materials* (2012) pp. 2178-2185.
Jan. 10, 2014 Office Action issued in U.S. Appl. No. 13/445,523.
Jun. 18, 2014 Office Action issued in U.S. Appl. No. 13/445,523.
Kajii et al., "Visible to near-infrared organic light-emitting diodes using phosphorescent materials by solution process," *Thin Solid Films* (2009) pp. 551-554.
U.S. Appl. No. 13/445,523 in the name of Fujita et al., filed Apr. 12, 2012.
U.S. Appl. No. 13/564,384 in the name of Fujita et al., filed Aug. 1, 2012.
U.S. Appl. No. 13/564,376 in the name of Yamamoto et al., filed Aug. 1, 2012.
U.S. Appl. No. 14/319,410 in the name of Fujita et al., filed Jun. 30, 2014.
U.S. Appl. No. 13/773,033 in the name of Yamamoto et al., filed Feb. 21, 2013.
U.S. Appl. No. 14/055,241 in the name of Fujita et al., filed Oct. 16, 2013.
Sep. 5, 2014 Notice of Allowance issued in U.S. Appl. No. 13/445,523.
Aug. 15, 2014 Office Action issued in U.S. Appl. No. 13/564,384.
Mar. 26, 2014 Notice of Allowance issued in U.S. Appl. No. 13/727,339.
Oct. 3, 2014 Office Action issued in U.S. Appl. No. 14/319,410.
Oct. 7, 2015 Office Action issued in U.S. Appl. No. 14/700,751.
Aug. 24, 2015 Office Action issued in U.S. Appl. No. 13/773,033.
Dec. 18, 2015 Office Action issued in U.S. Appl. No. 14/693,484.
Wang et al., "Syntheses, characterization and fluorescent properties of two series of dehydroabietic acid C-ring derivatives," Spectrochimica Acta Part A: Molecular and Biomolecular Spectroscopy, vol. 76, pp. 328-335, 2010.
May 9, 2016 Office Action issued in U.S. Appl. No. 14/693,484.
Aug. 9, 2016 Office Action issued in U.S. Appl. No. 14/055,241.
Apr. 6, 2017 Office Action issued in U.S. Appl. No. 14/693,484.
May 11, 2017 Notice of Allowance issued in U.S. Appl. No. 14/693,484.
Hamada et al., "Red organic light-emitting diodes using an emitting assist dopant," Applied Physics Letters, vol. 75, No. 12, pp. 1682-1684, Sep. 20, 1999.
Hamada et al., "Red organic light-emitting diodes using an emitting assist dopant," Applied Physics Letters, vol. 75, No. 12, pp. 1602-1604, Sep. 20, 1999.

\* cited by examiner (a) LIGHT EMITTING WAVEFORM IN EXAMPLE 3-2

(b) LIGHT EMITTING WAVEFORM IN EXAMPLE 3-8

(c) LIGHT EMITTING WAVEFORM IN EXAMPLE 3-9

(d) LIGHT EMITTING WAVEFORM IN COMPARATIVE EXAMPLE 3-1

THIADIAZOLE-BASED COMPOUND, LIGHT EMITTING ELEMENT COMPOUND, LIGHT EMITTING ELEMENT, LIGHT EMITTING DEVICE, AUTHENTICATION DEVICE, AND ELECTRONIC DEVICE

TECHNICAL FIELD

The present invention relates to a thiadiazole-based compound, a light emitting element compound, a light emitting element, a light emitting device, an authentication device, and an electronic device.

RELATED ART

An organic electroluminescence element (a so-called organic EL element) is a light emitting element with a structure where a light emitting organic layer with at least one layer is interposed between an anode and a cathode. In the light emitting element such as this, through the application of an electric field between the anode and the cathode, in the light emitting layer, a hole is injected from the anode at the same time as an electron is injected from the cathode, therefore an exciton is generated by the reunion of the electron and the hole in the light emitting layer and the energy is released as light when the exciton returns to the ground state.

As the light emitting element such as this, an element which emits at a long wavelength region over 700 nm is known (see Patent Document 1 and Patent Document 2, for example).

For example, in a light emitting element disclosed in Patent Documents 1 and 2, an emitting wavelength is made longer by using a material, in which, an amine as an electron donor, and a nitrile group as an electron acceptor, co-exist as a functional group in the molecule, as dopants of the light emitting layer.

However, in the past, an element with high efficiency and long life, which emits light in a near-infrared region was not able to be achieved.

Also, the light emitting element which plane emits with high efficiency and long life in a near-infrared region is in demand as a light source for biometric authentication which authenticates a person using biometric information such as a vein or a fingerprint.

PRIOR ART DOCUMENTS

Patent Documents

[Patent Document 1] JP-A-2000-091073
[Patent Document 2] JP-A-2001-110570

SUMMARY OF INVENTION

Problems to be Solved by the Present Invention

An object of the present invention is to provide a thiadiazole-based compound, a light emitting element compound, a light emitting element, a light emitting device provided with the light emitting element, an authentication device, and an electronic device with high efficiency and long life which emit light in a near-infrared region.

Means for Solving the Problems

The above-described object is achieved by the following inventions.

A thiadiazole compound according to the present invention is characterized in that it is represented by following Formula (I).

[Chem. 1]

(I)

[In Formula (I), As each independently represent an aryl group which may have a substituent or a diarylamino group.]

A thiadiazole compound according to the present invention is characterized in that it is represented by following Formula (4).

[Chem. 2]

(4)

[In Formula (4), Rs each independently represent a hydrogen atom, an alkyl group, an aryl group which may have a substituent, or a diarylamino group.]

The thiadiazole-based compound such as this may emit light in a near-infrared region when, for example, used as a light emitting material for an organic EL element.

A thiadiazole compound according to the present invention is characterized in that it is represented by following Formula (6).

[Chem. 3]

(6)

[In Formula (6), Rs each independently represent a hydrogen atom, an alkyl group, or an aryl group which may have a substituent. Also adjacent carbons in two Rs may be connected and form a cyclic shape.]

The thiadiazole-based compound such as this may emit light in a near-infrared region when, for example, used as a light emitting material for an organic EL element.

A light emitting element compound according to the present invention is characterized in that it is represented by following Formula (4).

[Chem. 2]

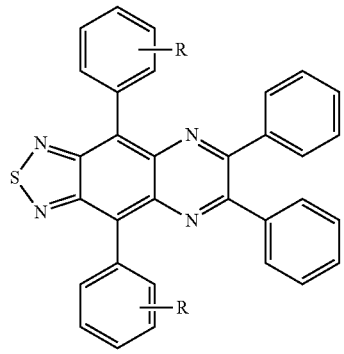

(4)

[In Formula (4), Rs each independently represent a hydrogen atom, an alkyl group an aryl group which may have a substituent, or a diarylamino group.]

The light emitting element compound such as this may emit light in a near-infrared region when, for example, used as a light emitting material.

A light emitting element compound according to the present invention is characterized in that it is represented by following Formula (6).

[Chem. 3]

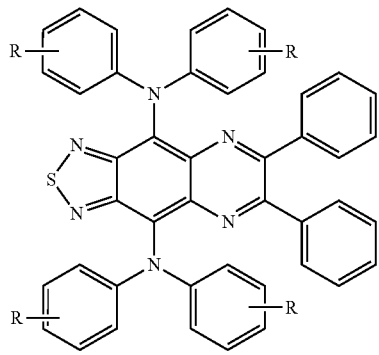

(6)

[In Formula (6), Rs each independently represent a hydrogen atom, an alkyl group, or an aryl group which may have a substituent. Also adjacent carbons in two Rs may be connected and form a cyclic shape.]

The light emitting element compound such as this may emit light in a near-infrared region when, for example, used as a light emitting material.

A light emitting element is characterized in that it includes an anode, a cathode, and a light emitting layer which is installed between the anode and the cathode and emits light by applying an electric current between the anode and the cathode, wherein the light emitting layer includes a compound expressed by following Formula (1) as a light emitting material, and a compound represented by following Formula IRH-1 as a host material which contains the light emitting material.

[Chem. 4]

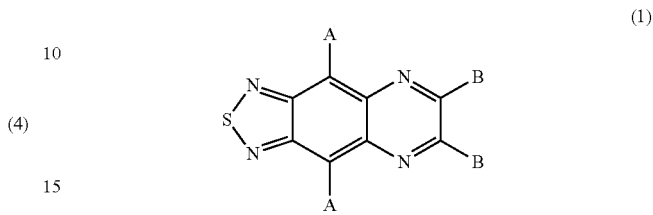

(1)

[In the Formula (1), A and B each independently represent a hydrogen atom, an alkyl group, an aryl group which may have a substituent, an arylamino group, or triarylamine.]

[Chem. 5]

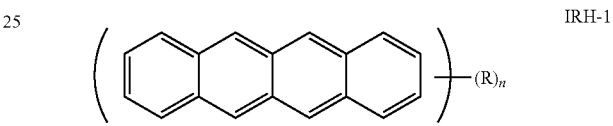

IRH-1

[In the Formula IRH-1, n represents a natural number of 1 to 12, Rs represent a substituent or a functional group, and each independently represents a hydrogen atom, an alkyl group, an aryl group which may have a substituent, or an arylamino group.]

According to the light emitting element of such a composition, it is possible to obtain a light emission in a wavelength region equal to or more than 700 nm (a near-infrared region) since the compound expressed by Formula (1) is used as the light emitting material.

Also, since a tetracene-based material is used as the host material, it is possible to transport energy from the host material to the light emitting material effectively. Therefore, light emitting efficiency of the light emitting element may be excellent.

Also, since the tetracene-based material shows an excellent stability (tolerance) toward electrons and holes, it is possible to extend the life of the light emitting layer, furthermore, to extend the life of the light emitting element.

In the light emitting element according to the present invention, in the Formula (1), it is preferable that B be a phenyl group or a methyl group, respectively.

The phenyl group and the methyl group each have high chemical stability. Thus, by using this type of compound as the light emitting material, it is possible to extend the life of the light emitting element. Also from the fact that the molecular weight of the light emitting material is able to be reduced, the light emitting layer may be formed with high accuracy using a vapor deposition film formation. As a result, it is possible to achieve high efficiency and long life of the light emitting element.

In the light emitting element according to the present invention, it is preferable that the light emitting layer further include a compound represented by following Formula IRH-2 as the host material.

[Chem. 6]

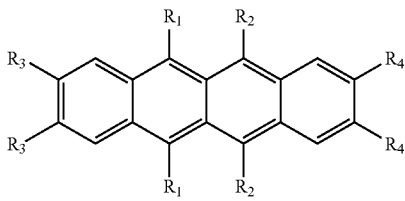

IRH-2

[In the Formula IRH-2, $R_1$ to $R_4$ each independently represent a hydrogen atom, an alkyl group, an aryl group which may have a substituent, or an arylamino group. In addition, $R_1$ to $R_4$ may be the same as or different from each other.]

As a result, it is possible to suppress a voltage build-up during continuous driving. Also it is possible to extend the life of the light emitting element and at the same time to increase the light emitting efficiency of the light emitting element.

In the light emitting element according to the present invention, it is preferable that the light emitting layer further include a compound represented by following Formula IRH-3 as the host material.

[Chem. 7]

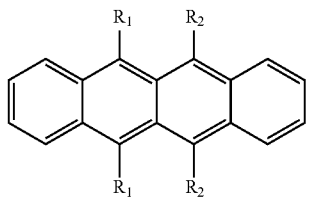

IRH-3

[In the Formula IRH-3, $R_1$ and $R_2$ each independently represent a hydrogen atom, an alkyl group, an aryl group which may have a substituent or an arylamino group. In addition, $R_1$ and $R_2$ may be the same as or different from each other.]

As a result, it is possible to suppress a voltage build-up during a continuous driving. Also it is possible to extend the life of the light emitting element and at the same time to increase the light emitting efficiency of the light emitting element.

A light emitting element is characterized in that it includes an anode, a cathode, and a light emitting layer which is installed between the anode and the cathode and emits light by applying an electric voltage between the anode and the cathode, wherein the light emitting layer includes a compound expressed by following Formula (1) as a light emitting material, and a compound represented by following Formula IRH-4 as a host material which contains the light emitting material.

[Chem. 4]

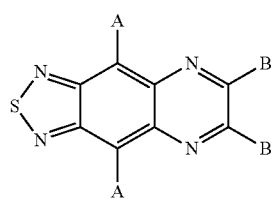

(1)

[In the Formula (1), A and B each independently represent a hydrogen atom, an alkyl group, an aryl group which may have a substituent, an arylamino group, or triarylamine.]

[Chem. 8]

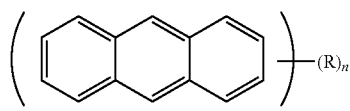

IRH-4

[In the Formula IRH-4, n represents a natural number of 1 to 10, Rs represent a substituent or a functional group, and each independently represents a hydrogen atom, an alkyl group, an aryl group which may have a substituent, or an arylamino group.]

According to the light emitting element of such a composition, it is possible to obtain a light emission in a wavelength region equal to or more than 700 nm (a near-infrared region) since the compound expressed by the Formula (1) is used as the light emitting material.

Also, since an anthracene-based material is used as the host material, it is possible to transport energy from the host material to the light emitting material effectively. Therefore, light emitting efficiency of the light emitting element may be excellent.

Also, since the anthracene-based material shows an excellent stability (tolerance) toward electrons and holes, it is possible to extend the life of the light emitting layer, furthermore, to extend the life of the light emitting element.

In the light emitting element according to the present invention, it is preferable that B be a phenyl group or a methyl group in the Formula (1), respectively.

The phenyl group and the methyl group each have high chemical stability. Thus, by using this type of compound as the light emitting material, it is possible to extend the life of the light emitting element. Also from the fact that the molecular weight of the light emitting material is able to be reduced, the light emitting layer may be formed with high accuracy using a vapor deposition film formation. As a result, it is possible to achieve high efficiency and long life of the light emitting element.

In the light emitting element according to the present invention, it is preferable that the light emitting layer further include a compound represented by following Formula IRH-5 as the host material.

[Chem. 9]

IRH-5

[In the Formula IRH-5, $R_1$ and $R_2$ each independently represent a hydrogen atom, an alkyl group, an aryl group which may have a substituent, or an arylamino group. In addition, $R_1$ and $R_2$ may be the same as or different from each other.]

As a result, it is possible to suppress a voltage build-up during continuous driving. Also it is possible to extend the life of the light emitting element and at the same time to increase the light emitting efficiency of the light emitting element.

In the light emitting element according to the present invention, it is preferable that the light emitting layer further include a compound represented by following Formula IRH-7 as the host material.

[Chem. 10]

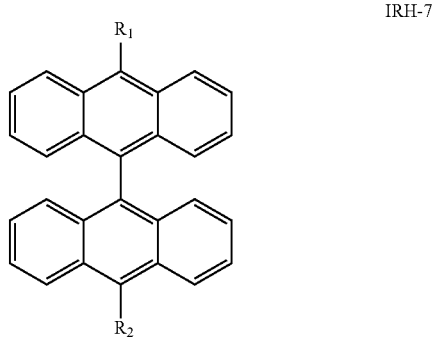

IRH-7

[In the Formula IRH-7, $R_1$ and $R_2$ each independently represent a hydrogen atom, an alkyl group, an aryl group which may have a substituent or an arylamino group. In addition, $R_1$ and $R_2$ may be the same as or different from each other.]

As a result, it is possible to suppress a voltage build-up during continuous driving. Also it is possible to extend the life of the light emitting element and at the same time to increase the light emitting efficiency of the light emitting element.

In the light emitting element according to the present invention, it is preferable that the light emitting layer further include a compound represented by following Formula IRH-8 as the host material.

[Chem. 11]

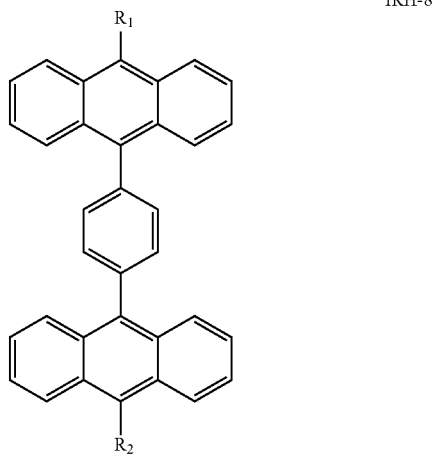

IRH-8

[In the Formula IRH-8, $R_1$ and $R_2$ each independently represent a hydrogen atom, an alkyl group, an aryl group which may have a substituent or an arylamino group. In addition, $R_1$ and $R_2$ may be the same as or different from each other.]

As a result, it is possible to suppress a voltage build-up during continuous driving. Also it is possible to extend the life of the light emitting element and at the same time to increase the light emitting efficiency of the light emitting element.

In the light emitting element according to the present invention, it is preferable that the host material include carbon atoms and hydrogen atoms.

As a result, it is possible to prevent an involuntary interaction between the host material and the light emitting material. Therefore light emitting efficiency of the light emitting element may be increased. Also, tolerance of the host material to a potential and holes may be increased. Therefore, it is possible to extend the life of the light emitting element.

A light emitting element is characterized in that it includes an anode, a cathode, a light emitting layer which is installed between the anode and the cathode and emits light by applying an electric voltage between the anode and the cathode, an electron transport layer which is installed between the anode and the light emitting layer, is in contact with the light emitting layer and has an electron transport property, wherein the light emitting layer includes a compound represented by following Formula (1) as a light emitting material, and wherein the electron transport layer includes a compound having an azaindolizine skeleton and an anthracene skeleton within the molecule as an electron transporting material.

[Chem. 4]

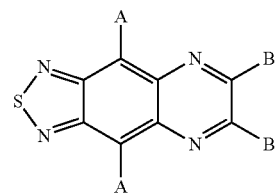

(1)

[In the Formula (1), A and B each independently represent a hydrogen atom, an alkyl group, an aryl group which may have a substituent, an arylamino group, or triarylamine.]

According to the light emitting element of such a composition, it is possible to obtain a light emission in a wavelength region equal to or more than 700 nm (a near-infrared region) since the compound represented by the Formula (1) is used as the light emitting material.

Also, since the compound having an azaindolizine skeleton and an anthracene skeleton within the molecule is used as the electron transporting material of the electron transport layer adjacent to the light emitting layer, it is possible to transfer an electron from the electron transport layer to the light emitting layer effectively. Therefore, light emitting efficiency of the light emitting element may be excellent.

Also, from the effective electron transfer from the electron transport layer to the light emitting layer, it is possible to lower the driving voltage of the light emitting element, and therefore, it is possible to extend the life of the light emitting element.

In addition, since the compound having an azaindolizine skeleton and an anthracene skeleton within the molecule shows an excellent stability (tolerance) toward electrons and holes, in this regard, it is possible to extend the life of the light emitting element as well.

In the light emitting element according to the present invention, it is preferable that B be a phenyl group or a methyl group in the Formula (1), respectively.

The phenyl group and the methyl group each have high chemical stability. Thus, by using this type of compound as the light emitting material, it is possible to extend the life of the light emitting element. Also from the fact that the molecular weight of the light emitting material is able to be reduced, the light emitting layer may be formed with high accuracy using a vapor deposition film formation. As a result, in this regard, it is possible to achieve high efficiency and long life of the light emitting element as well.

In the light emitting element according to the present invention, as the electron transporting material, it is preferable that the number of the azaindolizine skeletons and the anthracene skeletons included within one molecule be one or two, respectively.

As a result, the electron transport property and the electron injection property of the electron transport layer may be excellent.

In the light emitting element according to the present invention, it is preferable that the light emitting layer further include the host material which contains the light emitting material.

As a result, the host material, along with generating excitons from the reunion of the holes and the electrons, transports the energy of the excitons to the light emitting material, and therefore, may excite the light emitting material. Therefore, light emitting efficiency of the light emitting element may be excellent.

In the light emitting element according to the present invention, it is preferable that the host material include an acene-based material.

As a result, an electron may be effectively transported from the anthracene skeleton portion of the electron transporting material in the electron transport layer to the acene-based material in the light emitting layer.

In the light emitting element according to the present invention, it is preferable that the acene-based material be an anthracene-based material.

As a result, an electron may be effectively transported from the anthracene skeleton portion of the electron transporting material in the electron transport layer to the anthracene-based material in the light emitting layer.

In the light emitting element according to the present invention, it is preferable that the acene-based material be a tetracene-based material.

As a result, an electron may be effectively exchanged from the anthracene skeleton portion of the electron transporting material in the electron transport layer to the tetracene-based material in the light emitting layer.

In the light emitting element according to the present invention, it is preferable that the acene-based material include carbon atoms and hydrogen atoms.

As a result, it is possible to prevent an involuntary interaction between the host material and the light emitting material. Therefore light emitting efficiency of the light emitting element may be increased. Also, tolerance of the host material to a potential and holes may be increased. Therefore, it is possible to extend the life of the light emitting element.

In the light emitting element according to the present invention, it is preferable that the host material include a quinolinolato-based metal complex.

As a result, the quinolinolato-based metal complex, along with generating excitons from the reunion of the holes and electrons, transports the energy of the excitons to the light emitting material, and therefore, may excite the light emitting material.

In the light emitting element according to the present invention, it is preferable that the electron transport layer include a first electron transport layer which includes the compound having the azaindolizine skeleton and the anthracene skeleton within the molecule as a first electron transporting material and a second electron transport layer which is installed between the first electron transport layer and the light emitting layer, is in contact with both of these layers and, includes a second electron transporting material which is different from the first electron transporting material.

As a result, it is possible to extend the life of the light emitting element.

A light emitting device according to the present invention is characterized in that it includes the light emitting element according to the present invention.

The light emitting device such as this may emit light in a near-infrared region. Also, the light emitting device shows an excellent reliability since the light emitting element with high efficiency and long life is included.

An authentication device according to the present invention is characterized in that it includes the light emitting element according to the present invention.

The authentication device such as this may be used for biometric authentication using near-infrared light. Also, the authentication device shows an excellent reliability since the light emitting element with high efficiency and long life is included.

An electronic device according to the present invention is characterized in that it includes the light emitting element according to the present invention.

The electronic device such as this shows an excellent reliability since the light emitting element with high efficiency and long life is included.

BEST MODES FOR CARRYING OUT THE PRESENT INVENTION

Hereinafter, a thiadiazole-based compound, a light emitting compound, a light emitting element, a light emitting device, an authentication device, and an electronic device according to the present invention will be described with reference to the preferred embodiments shown in the accompanying drawings.

Figure 1:
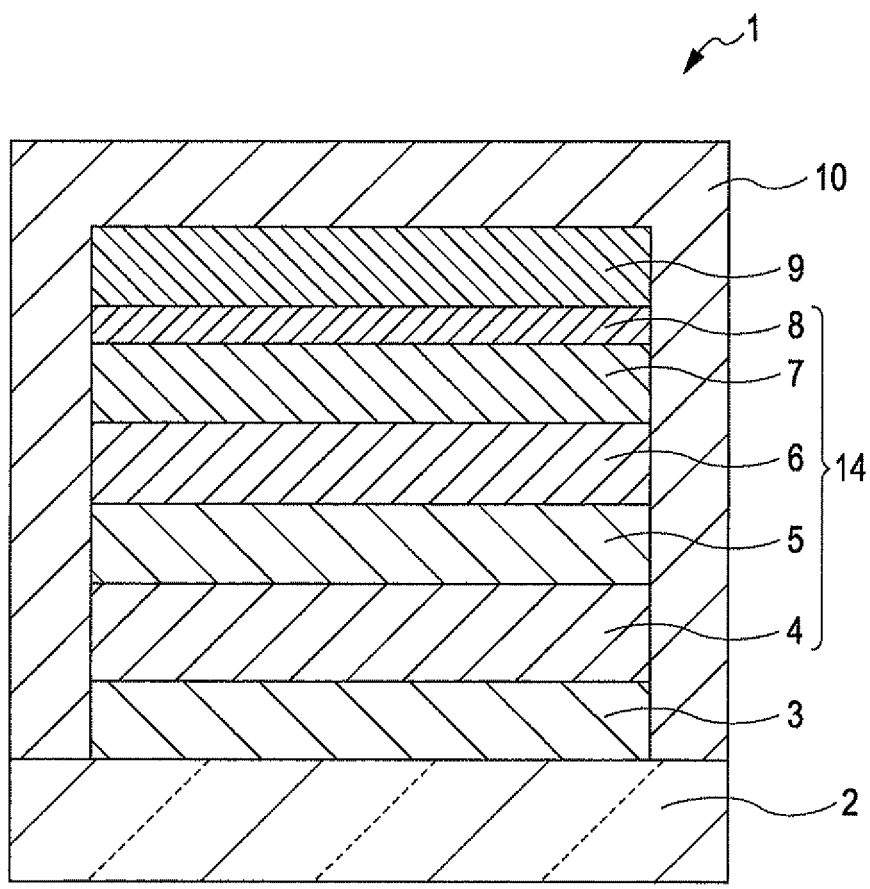
FIG. 1 is a diagram that schematically shows a longitudinal section of a light emitting element according to an embodiment of the present invention.

FIG. 1 is a diagram that schematically shows a longitudinal section of a light emitting element according to the embodiment of the present invention. Also, hereinafter, the upper side of FIG. 1 will be described as "top" and the lower side as "bottom" for convenience sake.

The light emitting element (electroluminescence element) 1 shown in FIG. 1 includes an anode 3, a hole injection layer 4, a hole transport layer 5, a light emitting layer 6, an electron transport layer 7, an electron injection layer 8, and a cathode 9, all being stacked in sequence. That is, in the light emitting element 1, between the anode 3 and the cathode 9, a stacked body 14, in which the hole injection layer 4, the hole transport layer 5, the light emitting layer 6, the electron transport layer 7, and the electron injection layer 8 are stacked starting from the anode 3 to the cathode 9, is interposed.

Additionally, the light emitting element 1 is sealed with a sealing member 10 at the same time as the whole element is installed on a substrate 2.

In the light emitting element 1 such as this, through the application of a driving voltage to the anode 3 and the cathode 9, a hole is introduced (injected) from the anode 3 at the same time as an electron is introduced (injected) from the cathode 9 with regard to the light emitting layer 6. Furthermore in the light emitting layer 6, the hole and the electron are reunited, an exciton is generated by the energy emitted from the reunion, and energy (fluorescence or phosphorescence) is released (emitted light) when the exciton returns to the ground state. This enables the light emitting element 1 to emit light.

The light emitting element 1, in particular, may emit light in a near-infrared region by using a thiadiazole-based compound (light emitting element compound) as an emitting material in the light emitting layer 6 as described later. Also, in this specification, "near-infrared region" represents the wavelength region of equal to or more than 700 nm and equal to or less than 1500 nm.

The substrate 2 supports the anode 3. The light emitting element 1 according to the embodiments is configured to take out the light from the side of the substrate 2 (bottom emission type); therefore, the substrate 2 and the anode 3 are substantially transparent (colorless and transparent, colored and transparent, or semi-transparent), respectively.

As a component material for the substrate 2, for example, a resin material such as polyethylene terephthalate, polyethylene naphthalate, polypropylene, cycloolefin polymer, polyamide, polyethersulfone, polymethylmethacrylate, polycarbonate, or polyarylate; or a glass material such as quartz glass or soda glass or the like may be used and be used either alone or as a combination of two or more.

The average thickness of the substrate 2 such as this, while not particularly limited, is preferably about 0.1 to 30 nm and more preferably about 0.1 to 10 nm.

Also, in a case in which the light emitting element 1 is configured to take out the light from the opposite side of the substrate 2 (top emission type), both a transparent substrate and an opaque substrate may be used as the substrate 2.

As the opaque substrate, for example, a substrate composed of a ceramic material such as alumina, a substrate in which an oxide film (an insulation film) is formed on the surface of a metal substrate such as stainless steel, and a substrate made of a resin material, may be used.

Also, in the light emitting element 1 such as this, the distance between the anode 3 and the cathode 9 (that is, the average thickness of the stacked body 14) is preferably 100 to 500 nm, more preferably 100 to 300 nm, and even more preferably 100 to 250 nm. This, simply and reliably, enables the driving voltage of the light emitting element 1 to be within the practical range.

Hereinafter, each part which configures the light emitting element 1 will be described one by one.

(Anode)

The anode 3 is an electrode in which holes are injected to the hole transport layer 5 through the hole injection layer 4 which is described later. As a component material for the anode 3, it is preferable that a material with large work function and excellent conductivity be used.

As the component material for the anode 3, for example, an oxide such as ITO (Indium Tin Oxide), IZO (Indium Zinc Oxide), $In_3O_3$, $SnO_2$, Sb containing $SnO_2$, or Al containing ZnO, Au, Pt, Ag, Cu, or an alloy containing these or the like may be used and used either alone or as a combination of two or more.

Particularly, it is preferable that the anode 3 be composed of ITO. ITO is a material with a large work function and excellent conductivity and, at the same time, is transparent. Therefore, it is possible for the holes to be injected effectively from the anode 3 to the hole injection layer 4.

Also a surface of the hole injection layer 4 side of the anode 3 (the top in FIG. 1) is preferably subjected to a plasma treatment. This enables the chemical and the mechanical stability of the joint surface of the anode 3 and the hole injection layer 4 to be enhanced. As a result, it is possible to improve the hole injection property from the anode 3 to the hole injection layer 4. Also, regarding the plasma treatment, this will be described in detail in the description of the production method of the light emitting element 1 which is described later.

The average thickness of the anode 3 such as this, while not particularly limited, is preferably about 10 to 200 nm and more preferably about 50 to 150 nm.

(Cathode)

On the other hand, the cathode 9 is an electrode in which electrons are injected to the electron transport layer 7 through the electron injection layer 8 which is described later. As a component material for the cathode 9, it is preferable that a material with a small work function be used.

As the component material for the cathode 9, for example, Li, Mg, Ca, Sr, La, Ce, Er, Eu, Sc, Y, Yb, Ag, Cu, Al, Cs, Rb or an alloy containing these or the like may be used and used either alone or as a combination of two or more (for example, as a stacked body of plural layers, a mixed layer of plural kinds, or the like).

Particularly, in a case in which the alloy is used as the component material for the cathode 9, it is preferable that an alloy with unreactive metal atoms such as Ag, Al, or Cu, more specifically, an alloy such as MgAg, AlLi, or CuLi be used. From the use of such an alloy as the component material for the cathode 9, electron injection efficiency and stability improvement of the cathode 9 may be expected.

The average thickness of the cathode 9 such as this, while not particularly limited, is preferably about 100 to 10000 nm and more preferably about 100 to 500 nm.

Since the light emitting element 1 according to the embodiments is a bottom emission type, light transparency of the cathode 9 is not required. Also, in a case in which a top emission type is used, the average thickness of the cathode 9 is preferably about 1 to 50 nm since light needs to penetrate from the side of the cathode 9.

(Hole Injection Layer)

The hole injection layer 4 has a function to increase the efficiency of hole injection from the anode 3 (that is, has a hole injection property).

In this way, by installing the hole injection layer 4 between the anode 3 and the hole transport layer 5 described later, it is possible to improve the hole injection property from the anode 3 and therefore to increase the light emitting efficiency of the light emitting element 1.

The hole injection layer 4 includes a material having the hole injection property (that is, a hole injection material).

As a hole injection material included in the hole injection layer 4, while not particularly limited, for example, copper phthalocyanine, 4,4',4''-tris(N,N-phenyl-3-methylphenylamino)triphenylamine (m-MTDATA), N,N'-bis-(4-diphenylaminophenyl)-N,N'-diphenylbiphenyl-4-4'-diamine, or the like may be used.

Among these, as the hole injection material included in the hole injection layer 4, an amine-based material is preferable from the viewpoint of a hole injection property and a hole transport property. It is more preferable that a diaminobenzene derivative, a benzidine derivative (a material having a benzidine skeleton), or a triamine-based compound, a tetraamine-based compound having both the "diaminobenzene" unit and the "benzidine" unit in the molecule be used.

The average thickness of the hole injection layer 4 such as this, while not particularly limited, is preferably about 5 to 90 nm and more preferably about 10 to 70 nm.

Also, the hole injection layer 4, depending on the component material of the anode 3 and the hole transport layer 5, may not be included.

(Hole Transport Layer)

The hole transport layer 5 has a function to transport the holes injected from the anode 3 through the hole injection layer 4 to the light emitting layer 6 (that is, has a hole transport property).

The hole transport layer 5 includes a material having the hole transport property (that is, a hole transporting material).

As a hole transporting material included in the hole transport layer 5, a variety of p-type high-molecular-weight materials or a variety of p-type low-molecular-weight materials may be used either alone or as a combination of two or more. For example, a tetraarylbenzidine derivative such as N,N'-di(1-naphthyl)-N,N'-diphenyl-1,1'-diphenyl-4,4'-diamine (NPD), or N,N'-diphenyl-N,N'-bis(3-methylphenyl)-1,1'-diphenyl-4,4'-diamine (TPD), a tetraaryldiaminofluorene compound or a derivatives thereof (an amine-based compound), tetra-p-biphenylbenzidine (HTL-1) or the like may be used and be used either alone or as a combination of two or more.

Among these, as the hole transporting material included in the hole transport layer 5, an amine-based material is preferable from the viewpoint of the hole injection property and the hole transport property and it is particularly preferable that a benzidine derivative (a material having a benzidine skeleton) be used.

The average thickness of the hole transport layer 5 such as this, while not particularly limited, is preferably about 5 to 90 nm and more preferably about 10 to 70 nm.

(Light Emitting Layer)

The light emitting layer 6 emits light by applying an electric voltage between the anode 3 and the cathode 9 described above.

The light emitting layer 6 includes a light emitting material.

The light emitting layer 6, in particular, includes a compound expressed by following Formula (1) as the light emitting material (hereinafter, simply referred to as a "thiadiazole-based compound").

[Chem. 4]

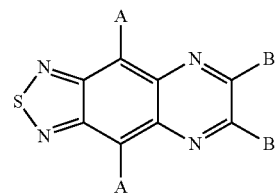

(1)

[In Formula (1), A and B, each independently represent a hydrogen atom, an alkyl group, an aryl group which may have a substituent, an arylamino group, or triarylamine.]

The light emitting layer 6 which includes the thiadiazole-based compound such as this may obtain a light emission in the wavelength region equal to or more than 700 nm (near-infrared region).

Particularly, as a light emitting material (thiadiazole-based compound) used in the light emitting layer 6, it is preferable that a compound expressed by following Formula (2) or Formula (3) be used.

[Chem. 12]

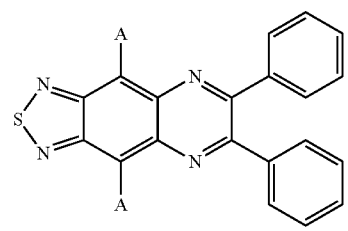

(2)

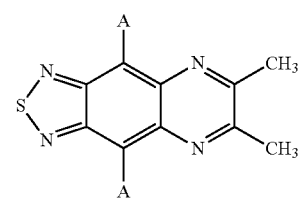

(3)

[In Formulae (2) and (3), A each independently represent a hydrogen atom, an alkyl group, an aryl group which may have a substituent, an arylamino group, or triarylamine.]

That is, in the Formula (1), it is preferable that B be a phenyl group or a methyl group, respectively.

The phenyl group and the methyl group each have high chemical stability. Thus, by using this type of compound as the light emitting material, it is possible to extend the life of the light emitting element 1. Also from the fact that the molecular weight of the light emitting material is able to be reduced, the light emitting layer 6 with high accuracy may be formed using a vapor deposition film formation. As a result, it is possible to achieve high efficiency and long life of the light emitting element 1.

In addition, as the light emitting material used in the light emitting layer 6, it is preferable that compounds expressed by following Formulae (4) to (9) be used. More specifically, in particular, it is preferable that compounds represented by following Formulae D-1 to D-3 be used.
[Chem. 13]
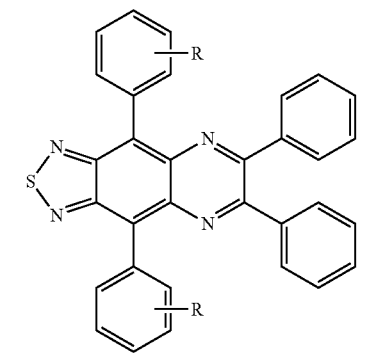
(4)
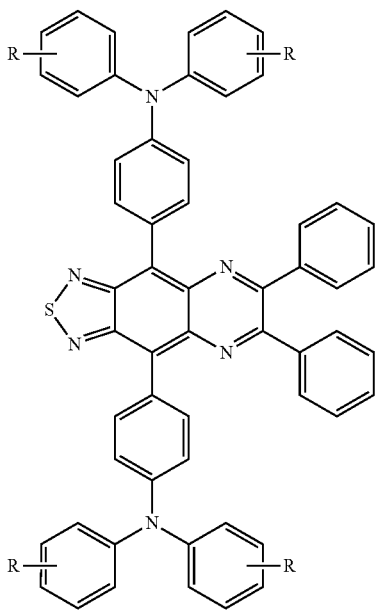
(5)
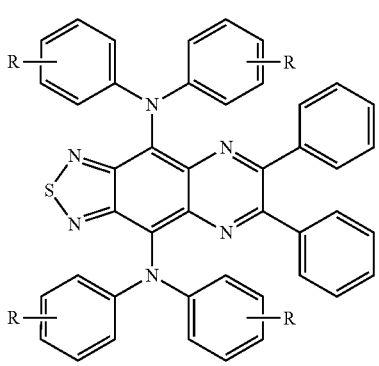
(6)
[Chem. 14]
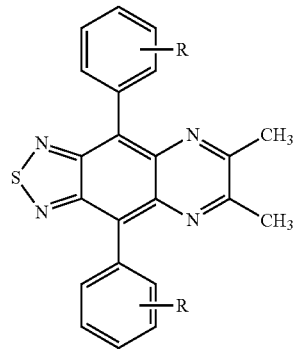
(7)
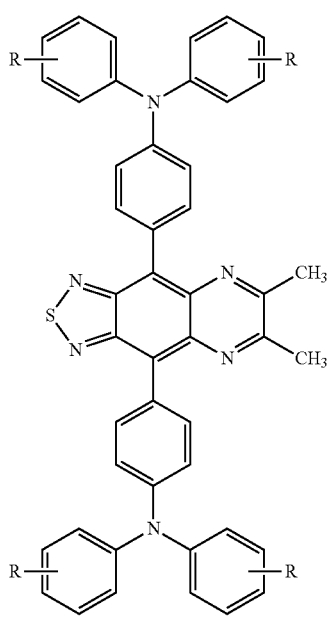
(8)
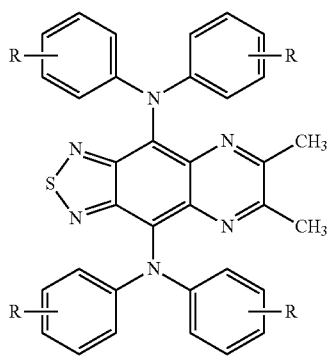
(9)
[In Formulae (4) to (9), R each independently represent a hydrogen atom, an alkyl group, or an aryl group which may have a substituent. Also adjacent carbons in two Rs may be connected and form a cyclic shape.]

[Chem. 15]

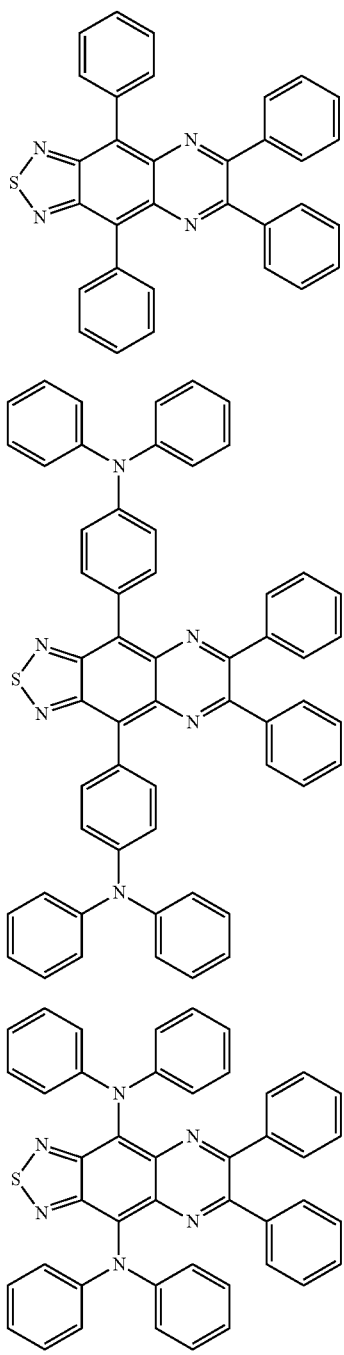

Also, the light emitting layer 6 may include a light emitting material (a variety of fluorescence materials, a variety of phosphorescence materials) other than the light emitting material described above.

Also, as a component material for the light emitting layer 6, in addition to the light emitting material described above, a host material in which this light emitting material is added (contained) as a guest material (dopant) may be used. The host material, along with generating excitons from the reunion of the holes and the electrons, has a function to transport the energy of the excitons to the light emitting material (a Foerster transport or a Dexter transport), and to excite the light emitting material. This makes it possible to increase the light emitting efficiency of the light emitting element 1. In the host material such as this, for example, the light emitting material which is a guest material may be used as a dopant doping to the host material.

As the host material, while not particularly limited as long as it functions as described above with regard to the light emitting material used, for example, a distyrylarylene derivative, a naphthacene derivative represented by following Formulae IRH-1, IRH-2, and IRH-3, an anthracene derivative such as 2-t-butyl-9,10-di(2-naphthyl)anthracene (TBADN), a perylene derivative, a distyrylbenzene derivative, a distyrylamine derivative, a quinolinolato-based metal complex such as bis(2-methyl-8-quinolinolato)(p-phenyl-phenolate)aluminum (BAlq) or tris(8-quinolinolato)aluminum complex ($Alq_3$), a triarylamine derivative such as triphenylamine tetramer, an oxadiazole derivative, rubrene and a derivative thereof, a silole derivative, a dicarbazole derivative, an oligothiophene derivative, a benzopyran derivative, a trizaole derivative, a benzoxazole derivative, a benzothiazole derivative, a quinoline derivative, a carbazole derivative such as 4,4'-bis(2,2'-diphenylvinyl)biphenyl (DPVBi), 3-phenyl-4-(1'-naphthyl)-5-phenylcarbazole, or 4,4'-N,N'-dicarbazolebiphenyl (CBP) or the like may be used and may be used alone or as a combination of two or more.

In particular, as the host material such as this, it is preferable that a tetracene-based material or an anthracene-based material which is an acene-based material be used. If the host material of the light emitting layer 6 includes the acene-based material, electrons may be effectively transferred from the anthracene skeleton portion of the electron transporting material in the electron transport layer 7 to the acene-based material in the light emitting layer 6.

The acene-based material, as described above, has a low level of reactivity with the light emitting material. Also, by using the acene-based material (particularly anthracene-based material and tetracene-based material) as the host material, an energy transfer from the host material to the light emitting material may be effectively performed. This is considered to be possible due to the facts as follows: (a) a generation of the singlet excited state of the light emitting material becomes possible through an energy transfer from the triplet excited state of the acene-based material, (b) an overlap between it electronic clouds of the acene-based material and electronic clouds of the light emitting material is increased, (c) an overlap between the fluorescent spectrum of the acene-based material and the absorption spectrum of the light emitting material is increased.

As a result, by using the acene-based material as the host material, light emitting efficiency of the light emitting element 1 may be increased.

Also, the acene-based material is excellent in tolerance to the electrons and the holes. Also the acene-based material is excellent in thermal stability. Therefore, it is possible to extend the life of the light emitting element 1. Also, since the acene-based material is excellent in thermal stability, in a case in which the light emitting layer is formed using a vapor deposition method, it is possible to prevent a decomposition of the host material due to a heat during the film formation. As a result, the light emitting layer with an excellent film quality may be produced; therefore, it is possible to extend the life of the light emitting element and at the same time to increase the light emitting efficiency of the light emitting element 1.

Also, since it is difficult for the acene-based material to emit light itself, it is possible to prevent an adverse effect of the host material on the light emitting spectrum of the light emitting element 1.

Also, the acene-based material is not particularly limited as long as it has an acene skeleton and also, has an effect as described above, and, for example, a naphthalene derivative, an anthracene derivative, a naphthacene derivative (a tetracene derivative), and a pentacene derivative may be used and may be used alone or as a combination of two or more, however, it is preferable that an anthracene derivative (an anthracene-based material) or a tetracene derivative (a tetracene-based material) be used.

As the tetracene-based material, while not particularly limited as long as it has at least one tetracene skeleton within one molecule and also functions as the host material as described above, it is preferable that a compound represented by following Formula IRH-1 be used, it is more preferable that a compound represented by following Formula IRH-2 be used, and it is even more preferable that a compound represented by following Formula IRH-3 be used. As a result, it is possible to suppress a voltage build-up during the continuous driving and also, it is possible to extend the life of the light emitting element 1 and at the same time to increase the light emitting efficiency of the light emitting element 1.

[Chem. 16]

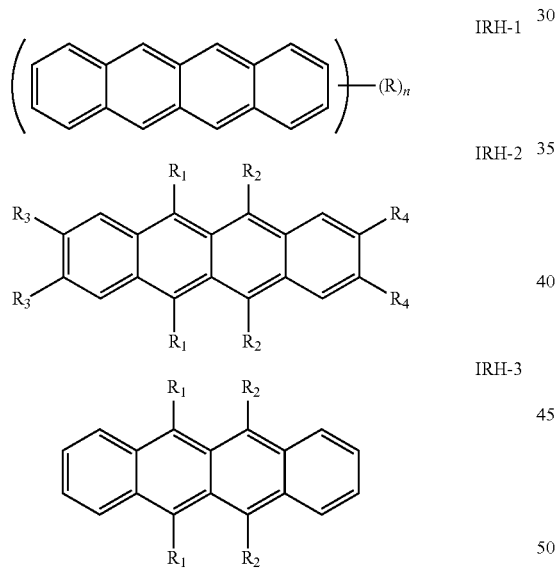

IRH-1

IRH-2

IRH-3

[In the Formula IRH-1, n represents a natural number of 1 to 12, Rs represent a substituent or a functional group, and each independently represents a hydrogen atom, an alkyl group, an aryl group which may have a substituent or an arylamino group. In the Formulae IRH-2 and IRH-3, $R_1$, to $R_4$ each independently represent a hydrogen atom, an alkyl group, an aryl group which may have a substituent or an arylamino group. In addition, $R_1$ to $R_4$ may be the same as or different from each other.]

Also, it is preferable that the tetracene-based material be composed of carbon atoms and hydrogen atoms. As a result, it is possible to prevent an involuntary interaction between the host material and the light emitting material. Therefore light emitting efficiency of the light emitting element 1 may be increased. Also, tolerance of the host material to the potential and the holes may be increased. Therefore, it is possible to suppress a voltage build-up during the continuous driving and also, it is possible to extend the life of the light emitting element 1.

Specifically, as the tetracene-based material, for example, it is preferable that compounds represented by following Formulae H1-1 to H1-11 and compounds represented by following Formulae H1-12 to H1-27 be used.

[Chem. 15]

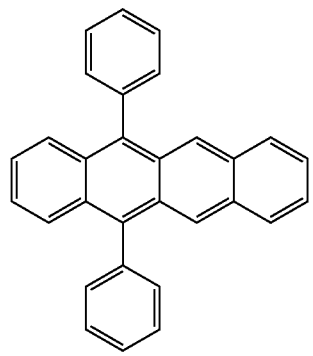

H1-1

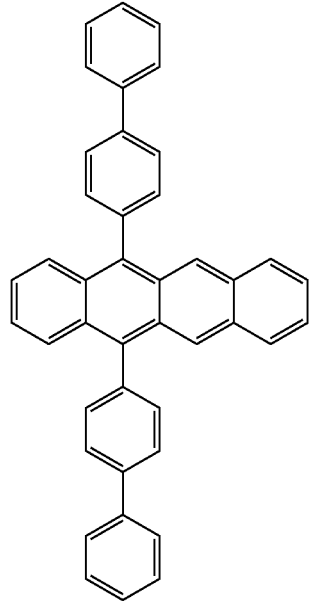

H1-2

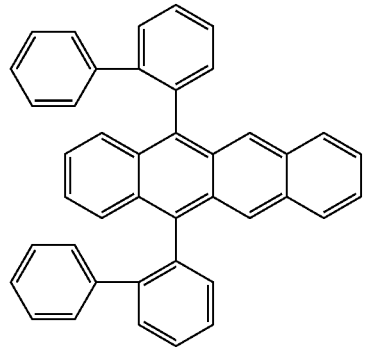

H1-3

H1-4
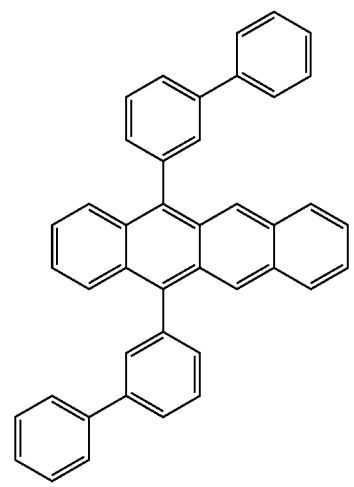
H1-5
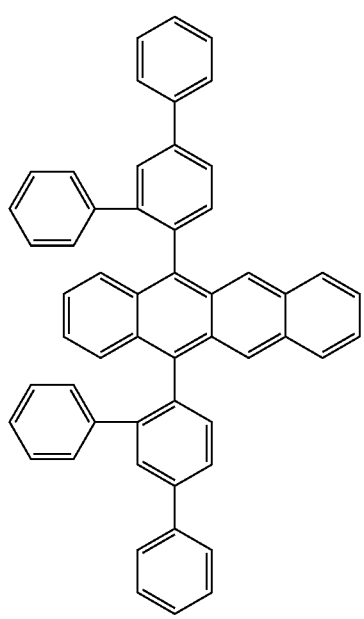
H1-6
H1-7
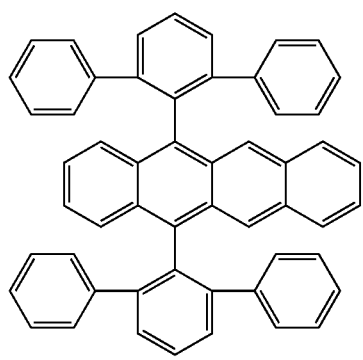
H1-8
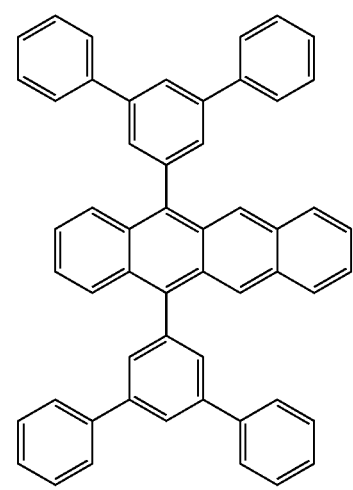
H1-9
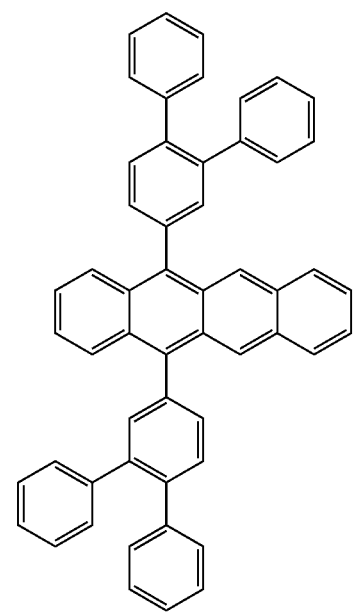

H1-10
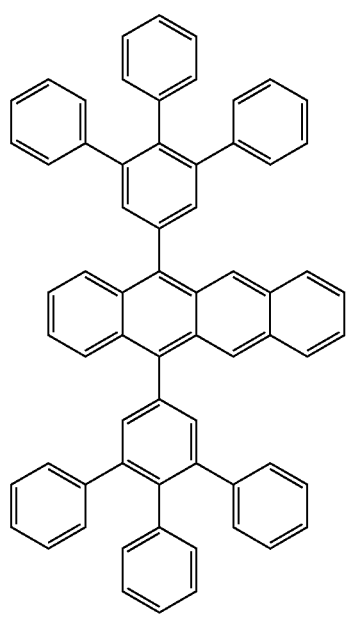
H1-11
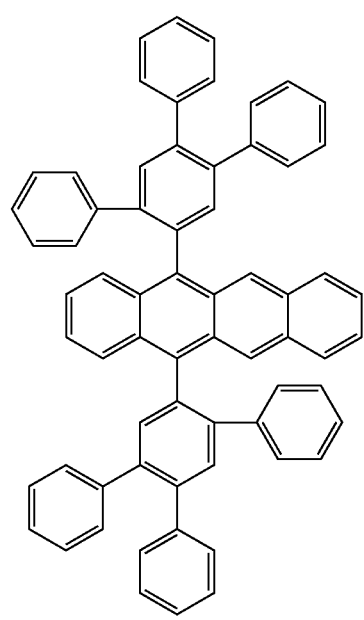
H1-12
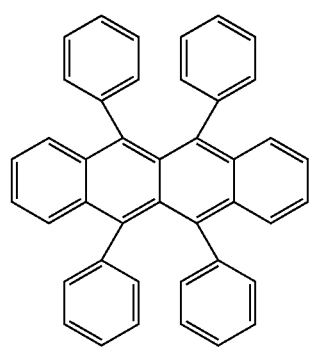
H1-13
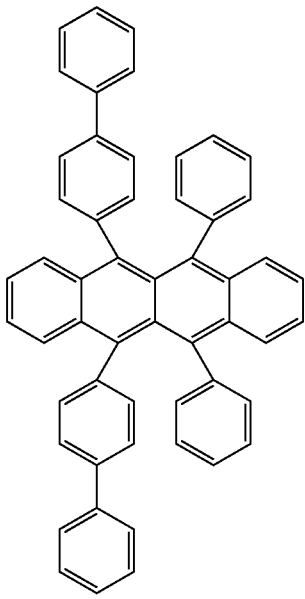
H1-14
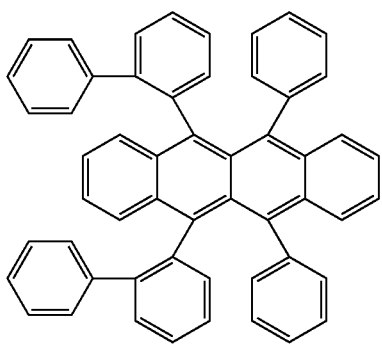
H1-15
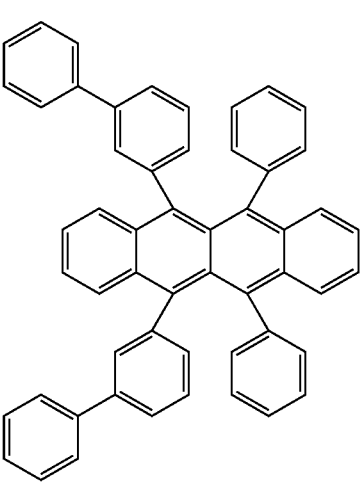

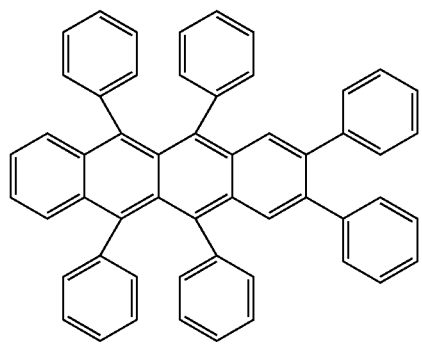
H1-16
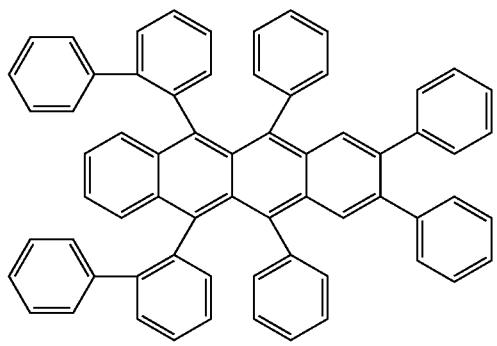
H1-19
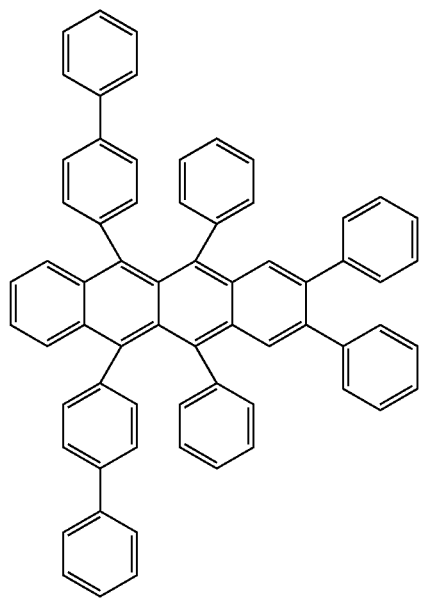
H1-17
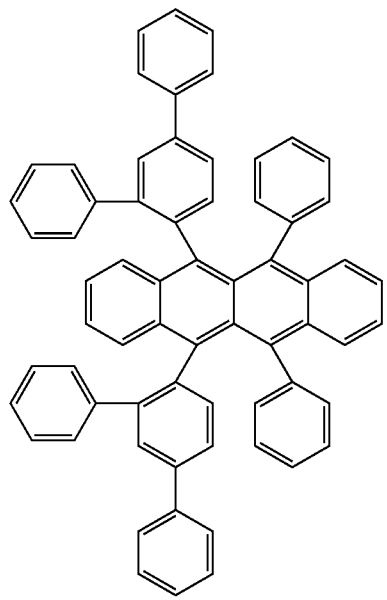
H1-20
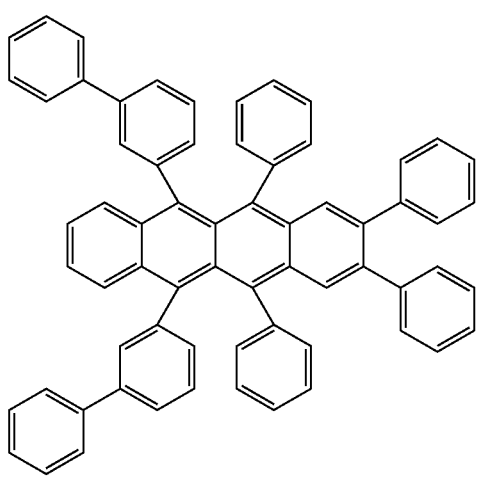
H1-18
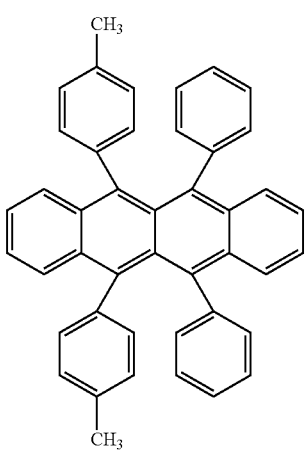
H1-21

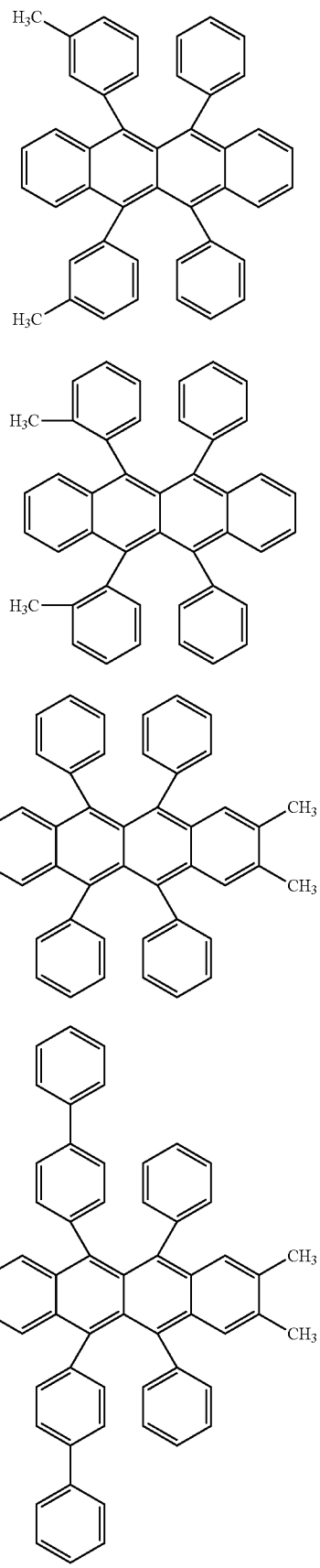

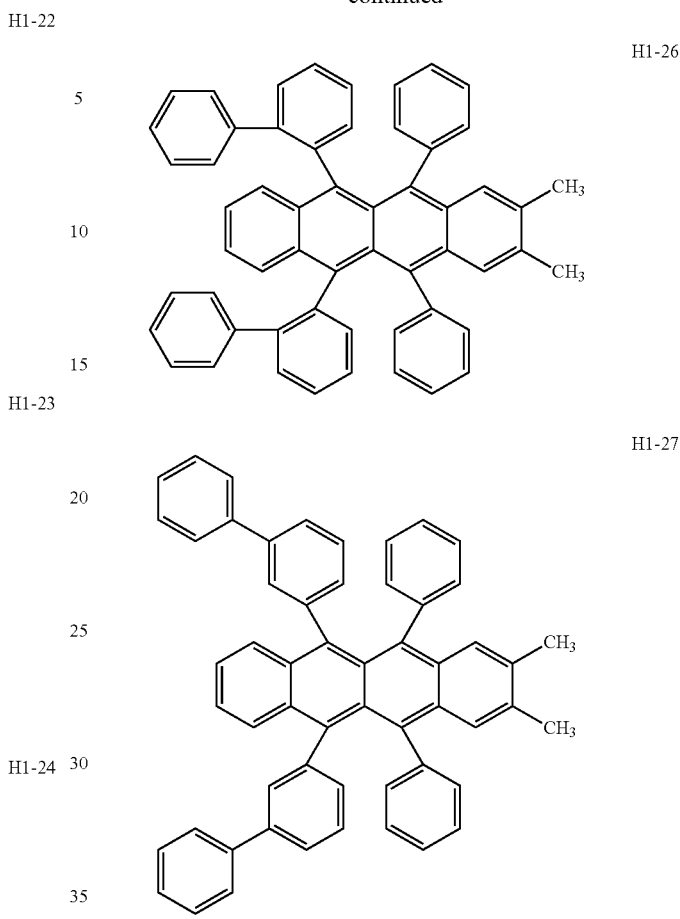

As the anthracene-based material, the compound expressed by following Formula IRH-4 or the derivative thereof may be used and, in particular, the compounds expressed by following Formulae IRH-5 to IRH-8 are preferable. As a result, it is possible to suppress a voltage build-up of the light emitting element 1 during the continuous driving. Also it is possible to extend the life of the light emitting element and at the same time to increase the light emitting efficiency of the light emitting element 1.

[Chem1 18]

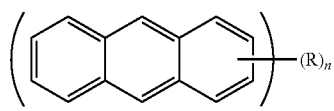

IRH-4

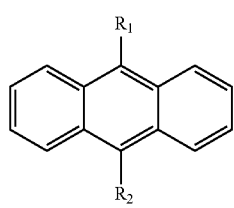

IRH-5

IRH-6

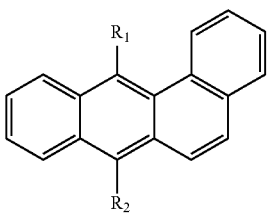

IRH-7

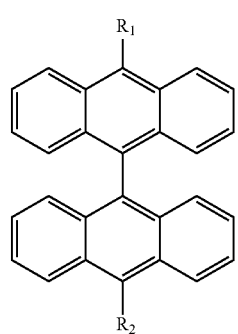

IRH-8

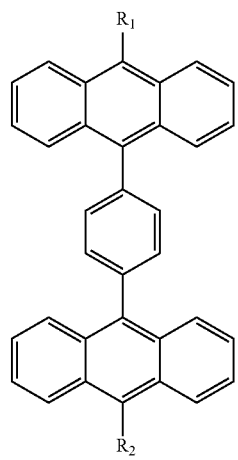

[In the Formula IRH-4, n represents a natural number of 1 to 10, Rs represent a substituent or a functional group, and each independently represents a hydrogen atom, an alkyl group, an aryl group which may have a substituent or an arylamino group. In the Formulae IRH-6 to IRH-8, $R_1$ and $R_2$ each independently represent a hydrogen atom, an alkyl group, an aryl group which may have a substituent or an arylamino group. In addition, $R_1$ and $R_2$ may be the same as or different from each other.]

Also, it is preferable that the anthracene-based material be composed of carbon atoms and hydrogen atoms. As a result, it is possible to prevent an involuntary interaction between the host material and the light emitting material. Therefore light emitting efficiency of the light emitting element 1 may be increased. Also, tolerance of the host material to the potential and the holes may be increased. Therefore, it is possible to extend the life of the light emitting element 1.

Specifically, as the anthracene-based material, for example, it is preferable that the compounds expressed by following Formulae H2-1 to H2-16, the compounds expressed by following Formulae H2-21 to H2-40, the compounds expressed by following Formulae H2-51 to H2-70, be used.

[Chem. 19]

H2-1

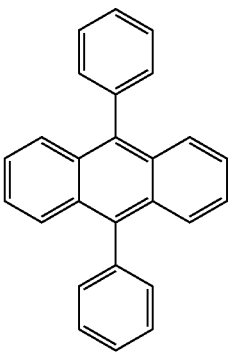

H2-2

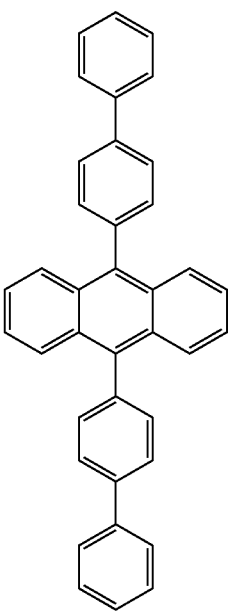

H2-3

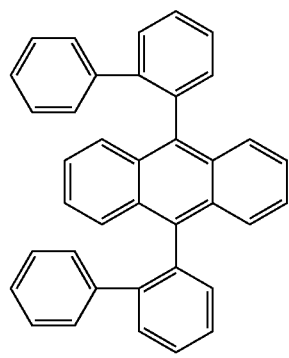

H2-4
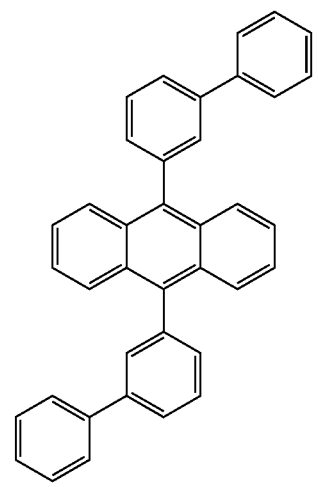
H2-5
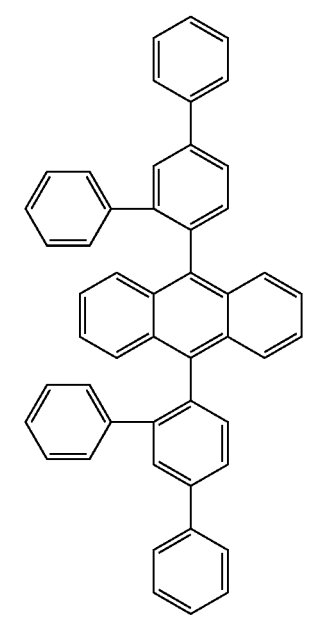
H2-6
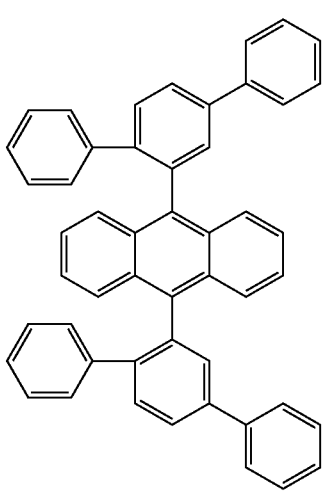
H2-7
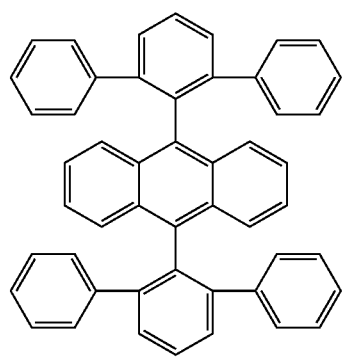
H2-8
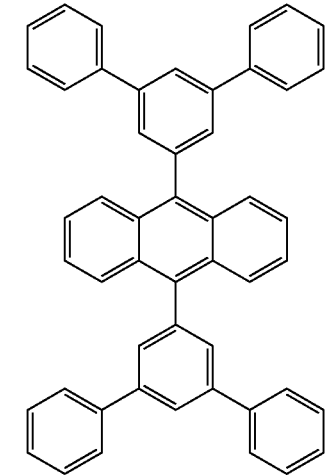
H2-9
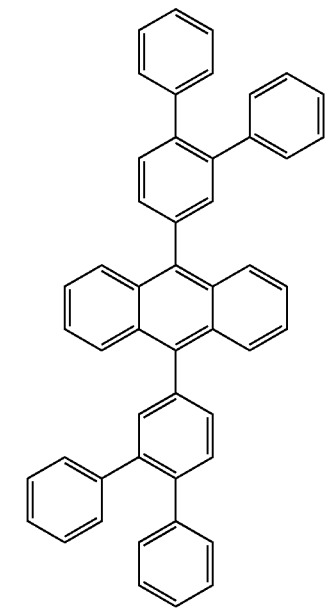

H2-10
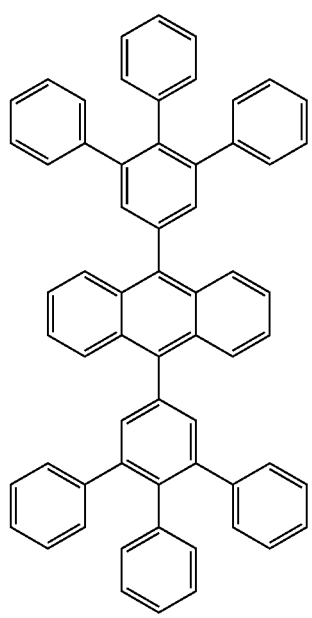
H2-11
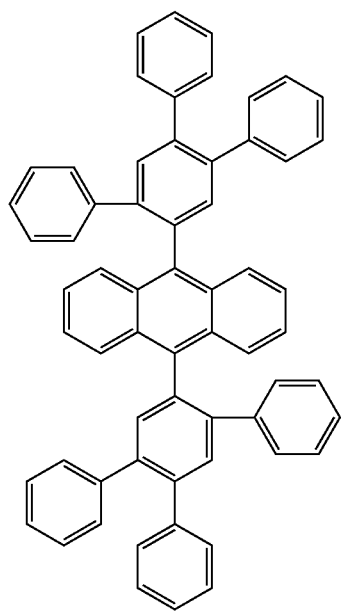
H2-12
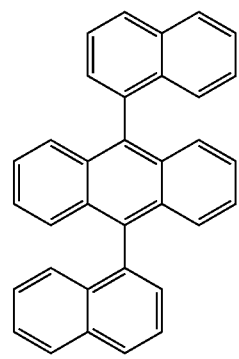
H2-13
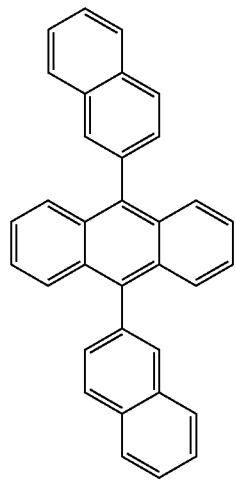
H2-14
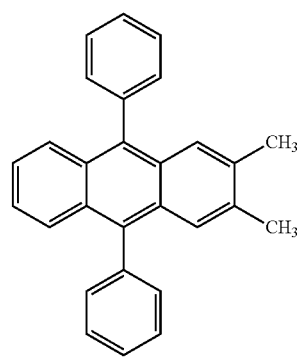
H2-15
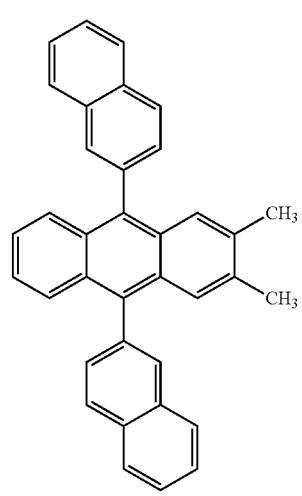

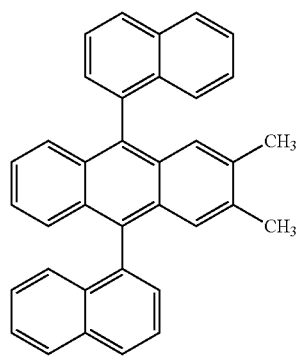
H2-16
[Chem. 20]
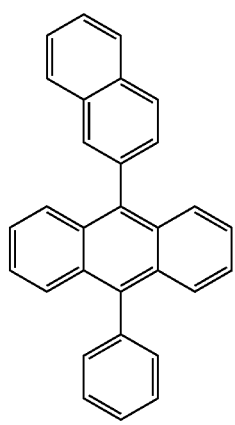
H2-21
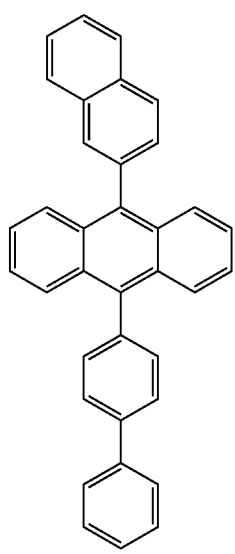
H2-22
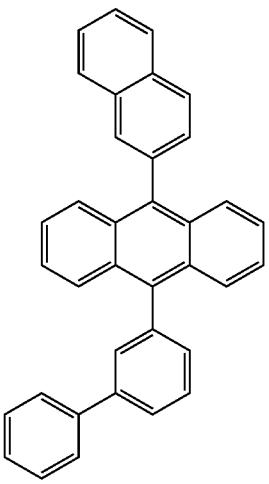
H2-23
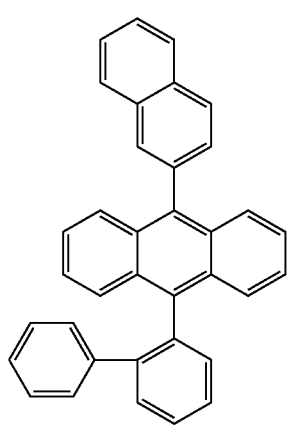
H2-24
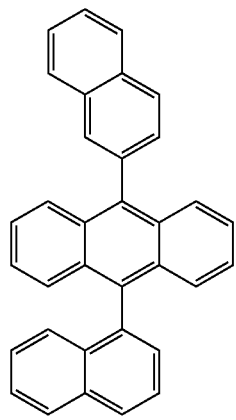
H2-25

-continued
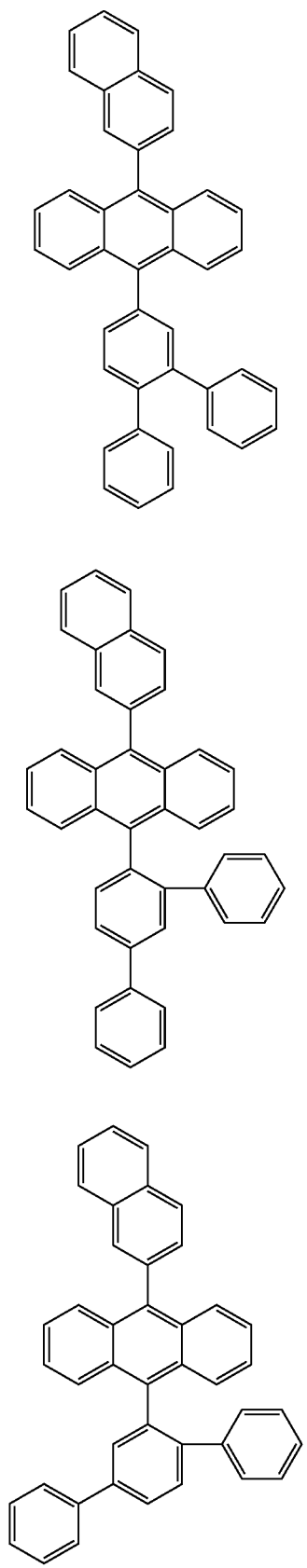
H2-26
H2-27
H2-28
-continued
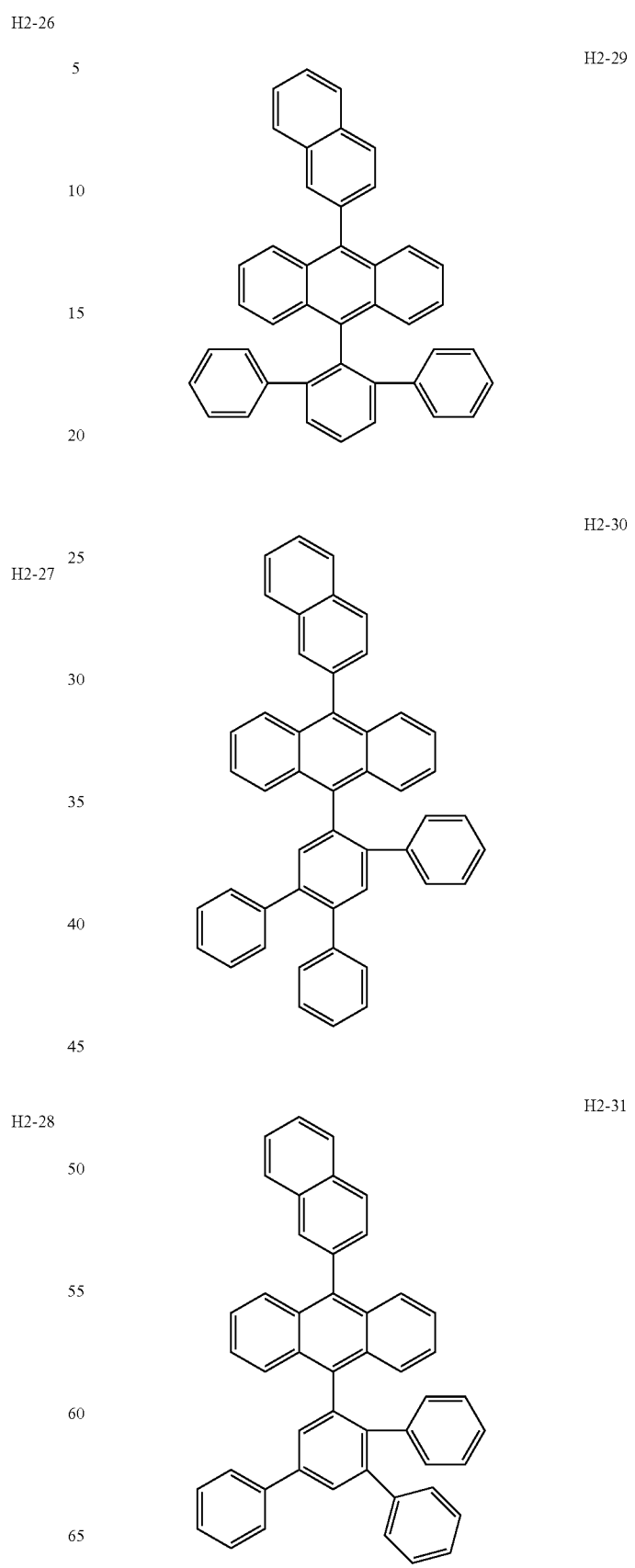
H2-29
H2-30
H2-31

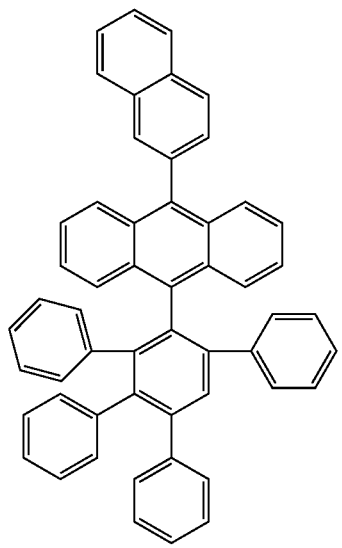
H2-32
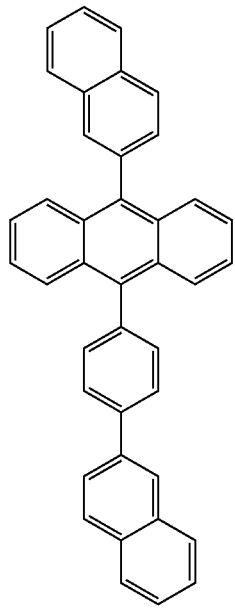
H2-34
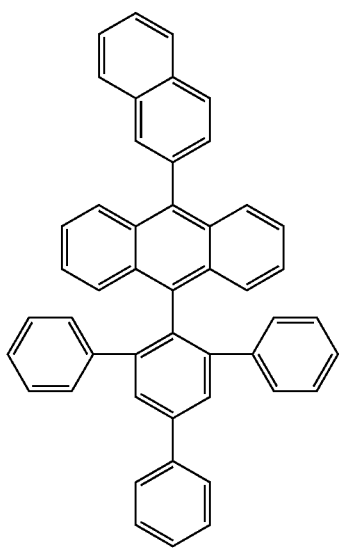
H2-33
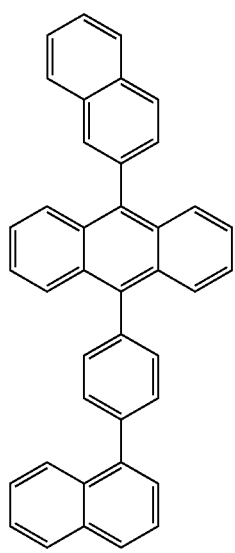
H2-35

H2-36
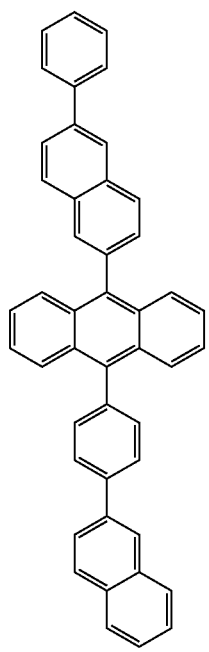
H2-37
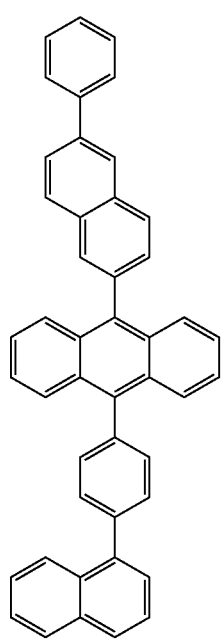
H2-38
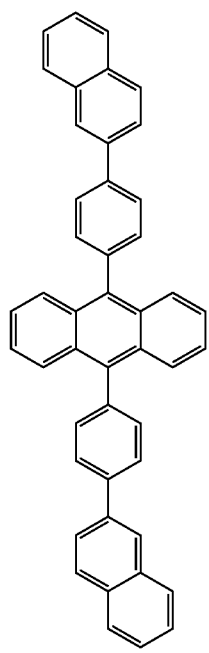
H2-39
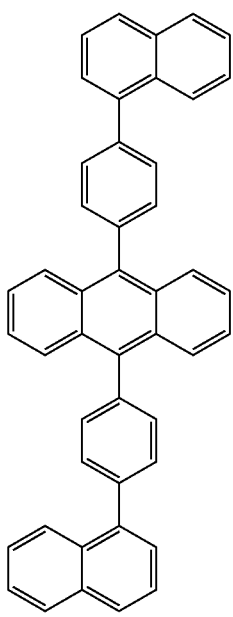

H2-40
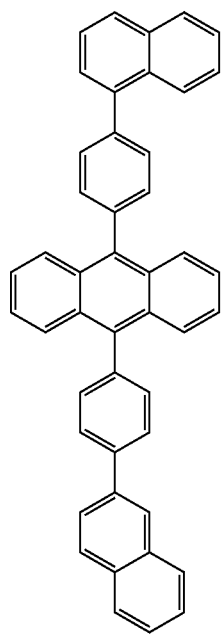
H2-51
H2-52
H2-53
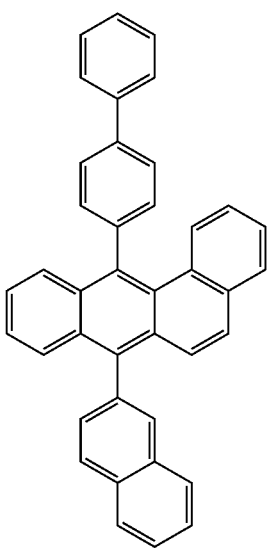
H2-54
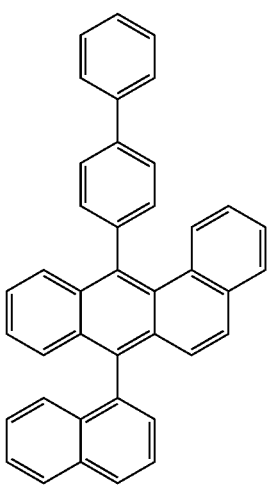
H2-55
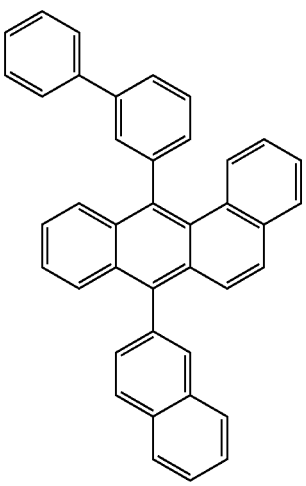

H2-56
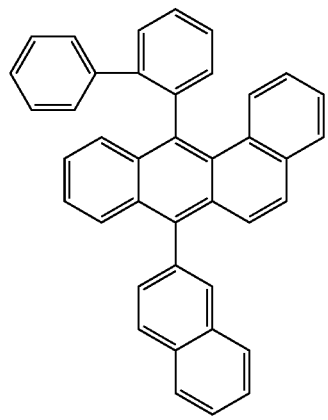
H2-57
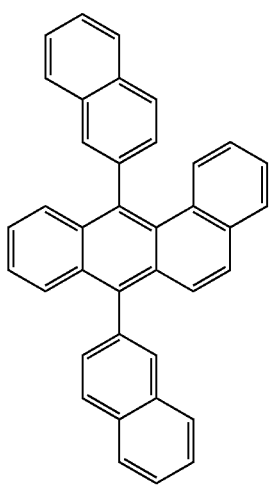
H2-58
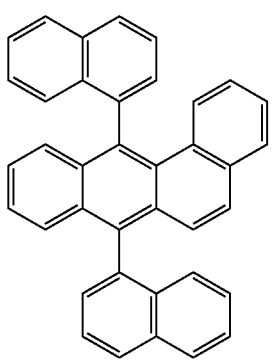
H2-59
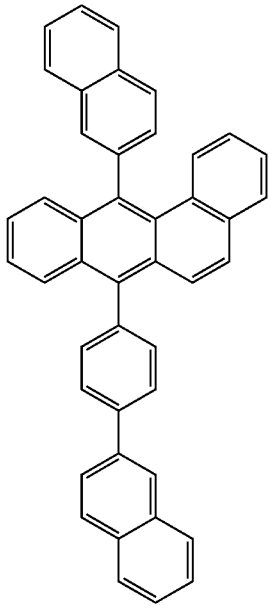
H2-60
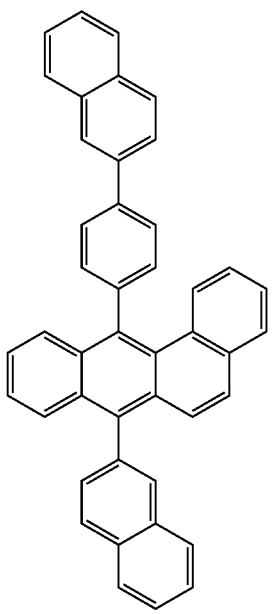

-continued
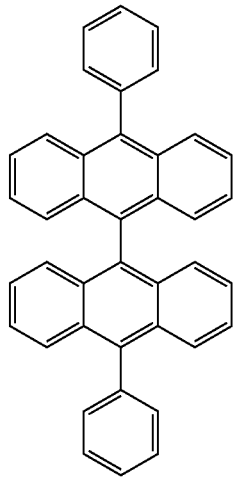
H2-61
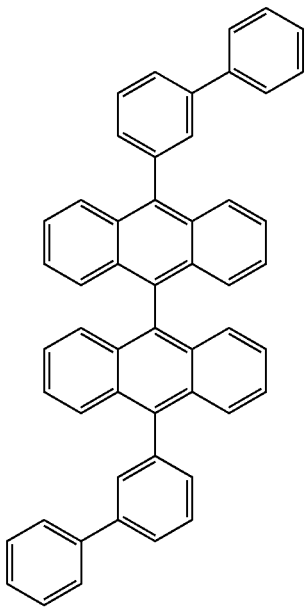
H2-62
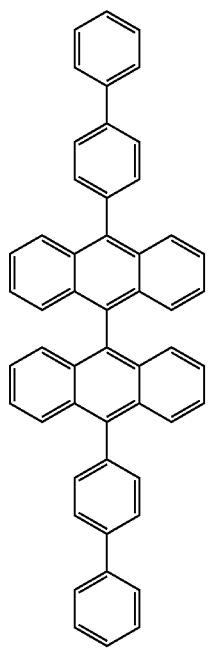
H2-63
H2-64
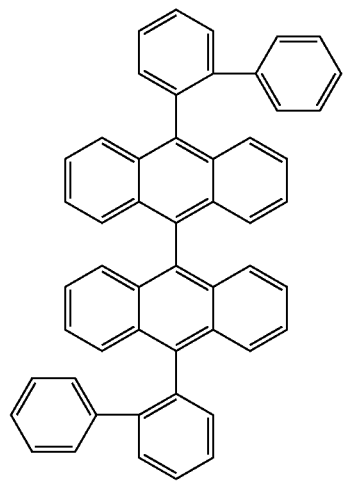

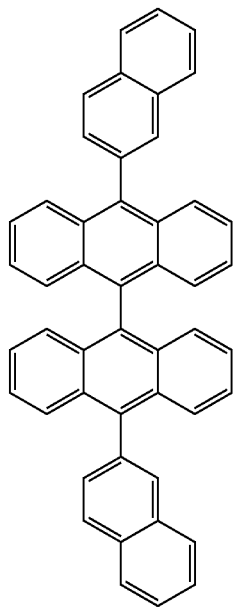
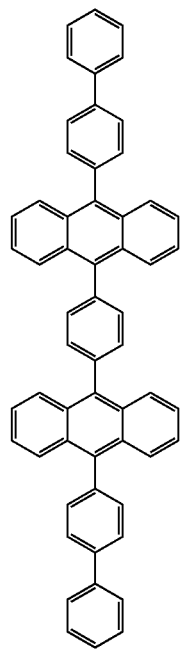
H2-65
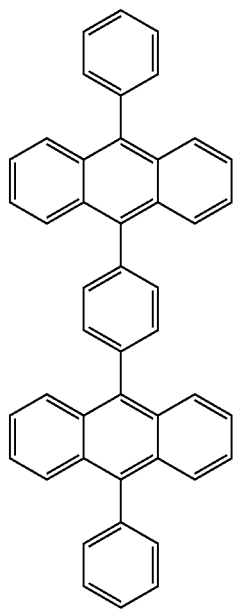
H2-66
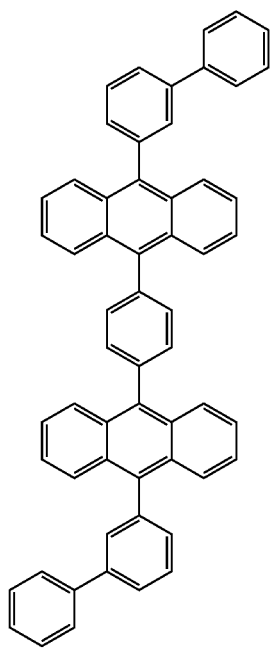
H2-67
H2-68

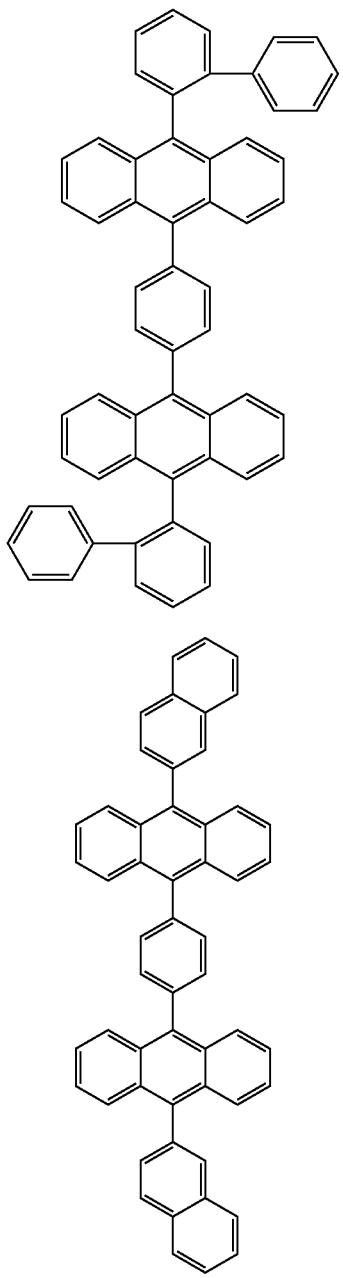

H2-69

H2-70

In the light emitting layer 6 which includes the light emitting material and the host material such as these, the content (doping amount) of the light emitting material is preferably 0.01 to 10 wt % and more preferably 0.1 to 5 wt %. Light emitting efficiency may be optimized by keeping the content of the light emitting material within this range.

Also, the average thickness of the light emitting layer 6, while not particularly limited, is preferably about 1 to 60 nm and more preferably about 3 to 50 nm.

(Electron Transport Layer)

The electron transport layer 7 has a function to transport the electrons injected from the cathode 9 through the electron injection layer 8 to the light emitting layer 6.

As a component material for the electron transport layer 7 (an electron transporting material), for example, a phenanthroline derivative such as 2,9-dimethyl-4,7-diphenyl-1,10-phenanthroline (BCP), a quinoline derivative such as an organic metal complex which uses 8-quinolinol such as tris(8-quinolinolato)aluminum ($Alq_3$) or a derivative thereof as a ligand, an azaindolizine derivative, an oxadiazole derivative, a perylene derivative, a pyridine derivative, a pyrimidine derivative, a quinoxaline derivative, a diphenylquinone derivative, a nitro-substituted fluorene derivative or the like may be used and be used either alone or as a combination of two or more.

Among these, as the electron transporting material used in the electron transport layer 7, an azaindolizine derivative is preferable and it is particularly preferable that a compound having an azaindolizine skeleton and an anthracene skeleton within the molecule (hereinafter, referred to as an "azaindolizine-based compound") be used.

As the electron transporting material used in the electron transport layer 7 adjacent to the light emitting layer 6, since the compound having an azaindolizine skeleton and an anthracene skeleton within the molecule is used, it is possible to effectively transport the electrons from the electron transport layer 7 to the light emitting layer 6. Therefore high light emitting efficiency of the light emitting element 1 may be achieved.

Also, since the electron transport from the electron transport layer 7 to the light emitting layer 6 may be effectively performed, it is possible to lower the driving voltage of the light emitting element 1, therefore, to extend the life of the light emitting element 1.

In addition, since the compound having an azaindolizine skeleton and an anthracene skeleton within the molecule shows an excellent stability (tolerance) toward electrons and holes, in this regard, it is possible to extend the life of the light emitting element 1 as well.

As the electron transporting material (azaindolizine-based compound) used in the electron transport layer 7, for example, it is preferable that the number of the azaindolizine skeletons and the anthracene skeletons included within one molecule be one or two. As a result, the electron transport property and the electron injection property of the electron transport layer 7 may be excellent.

Specifically, as the azaindolizine-based compound used in the electron transport layer 7, for example, it is preferable that compounds represented by following Formulae ELT-A1 to ELT-A24, compounds represented by following Formulae ELT-B1 to ELT-B12, and compounds represented by the following ELT-C1 to ELT-C20 be used.

[Chem. 22]

ETL-A1

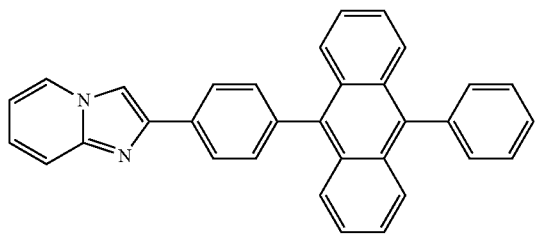

ETL-A2

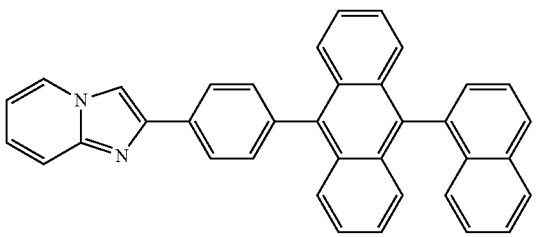

-continued
ETL-A3
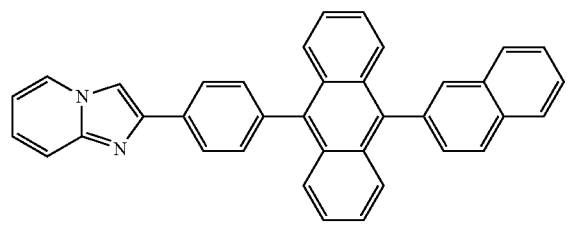
ETL-A4
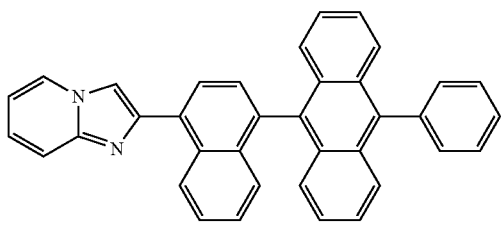
ETL-A5
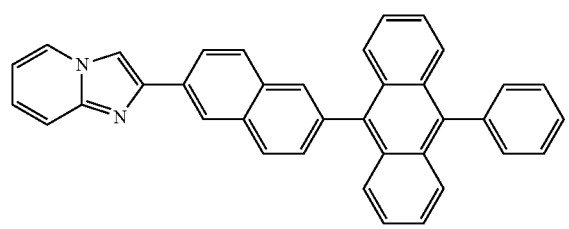
ETL-A6
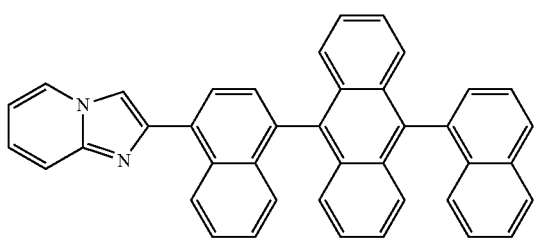
ETL-A7
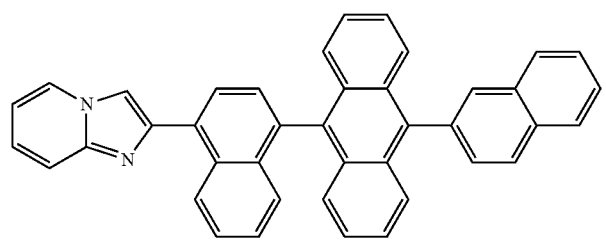
ETL-A8
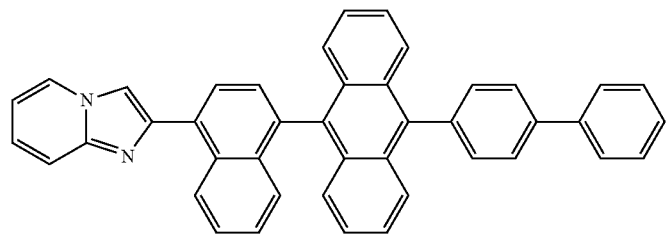
ETL-A9
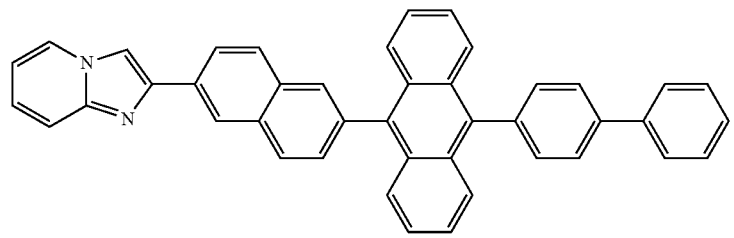
ETL-A10
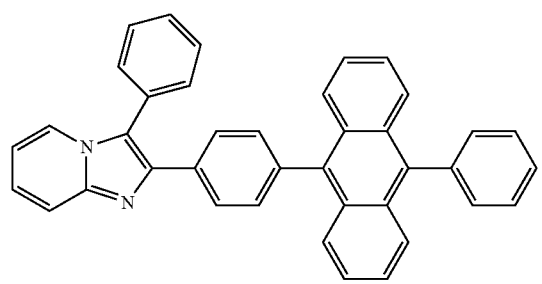
ETL-A11
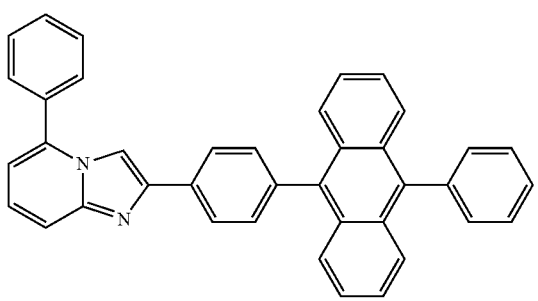

-continued
ETL-A12
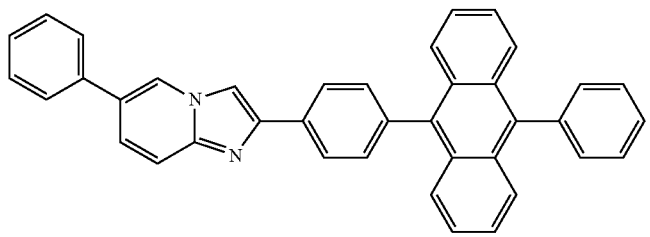
ETL-A13
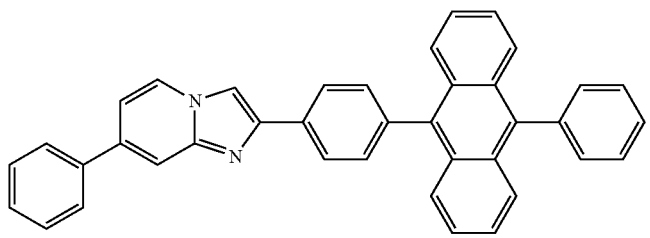
ETL-A14
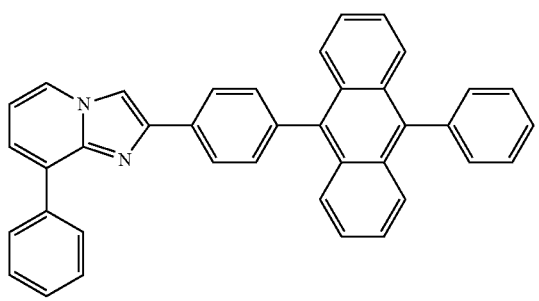
ETL-A15
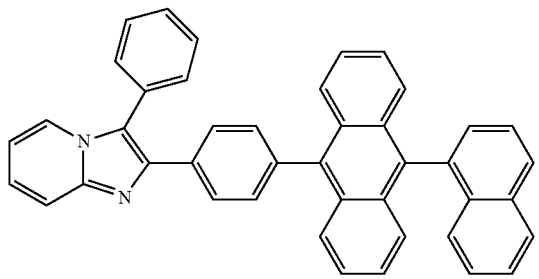
ETL-A16
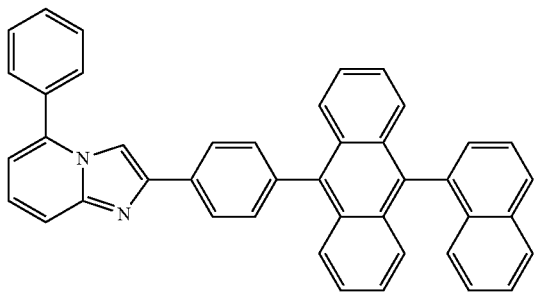
ETL-A17
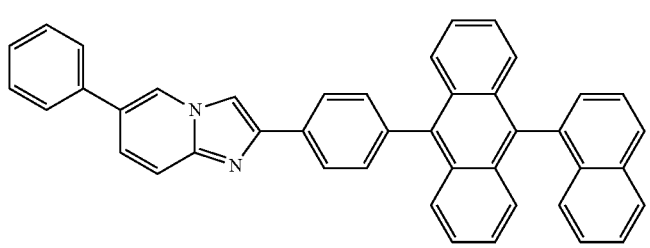
ETL-A18
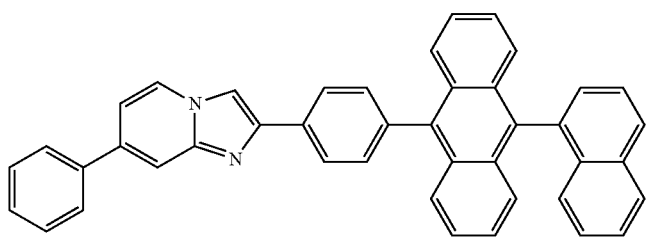

-continued
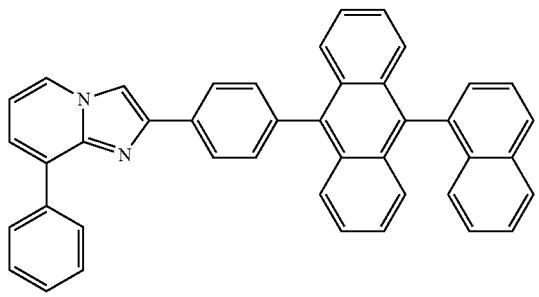
ETL-A19
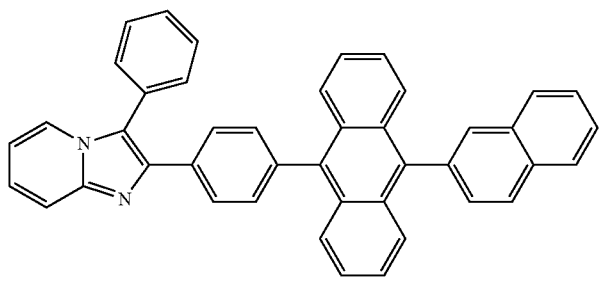
ETL-A20
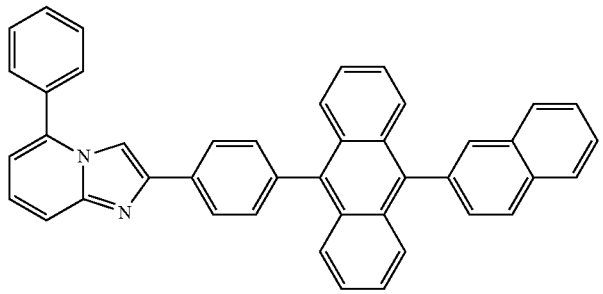
ETL-A21
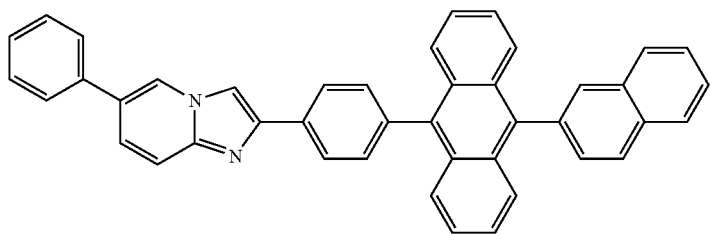
ETL-A22
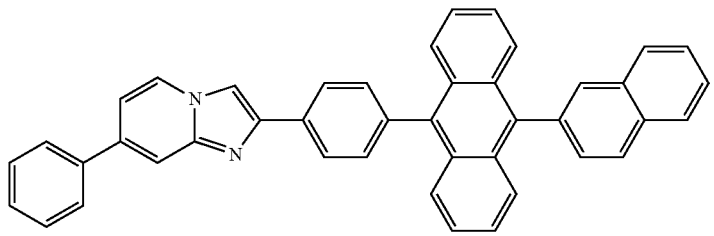
ETL-A23

-continued
ETL-A24
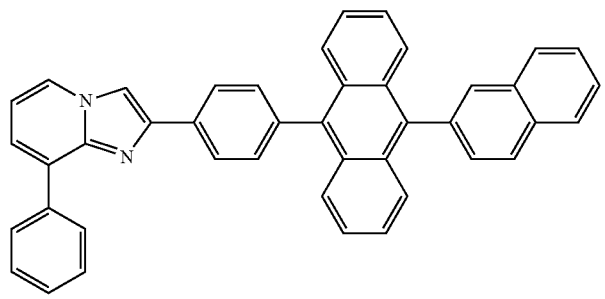
[Chem.23]
ETL-B1
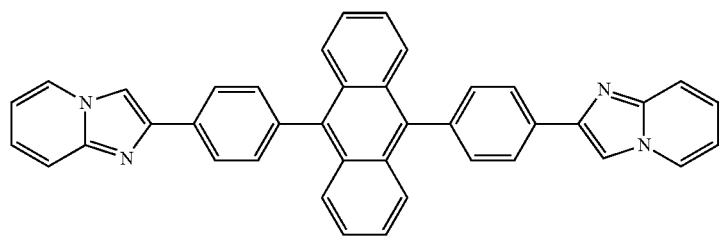
ETL-B2
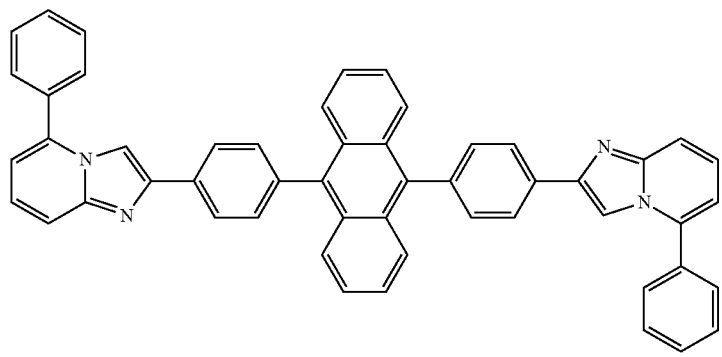
ETL-B3
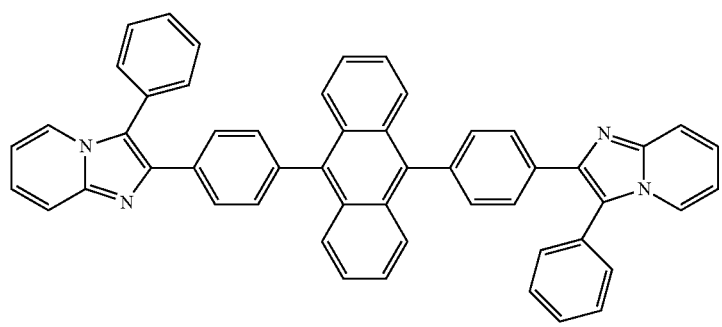
ETL-B4
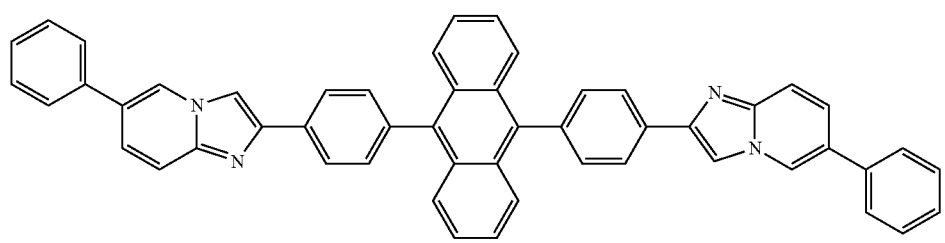

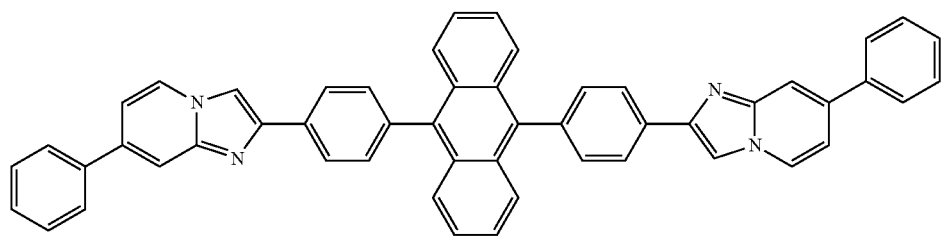
ETL-B5
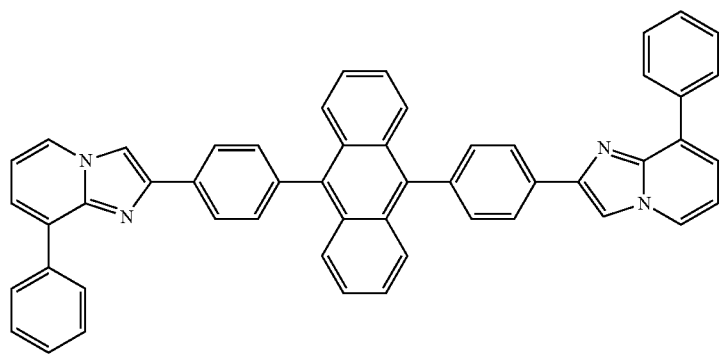
ETL-B6
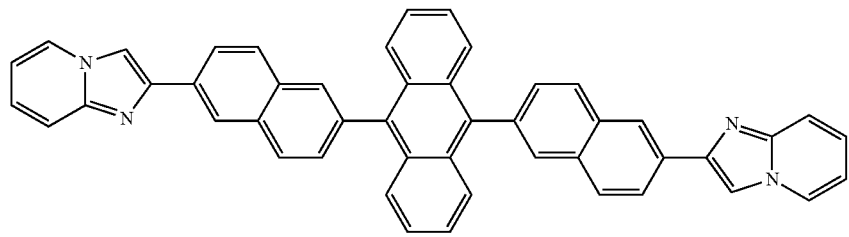
ETL-B7
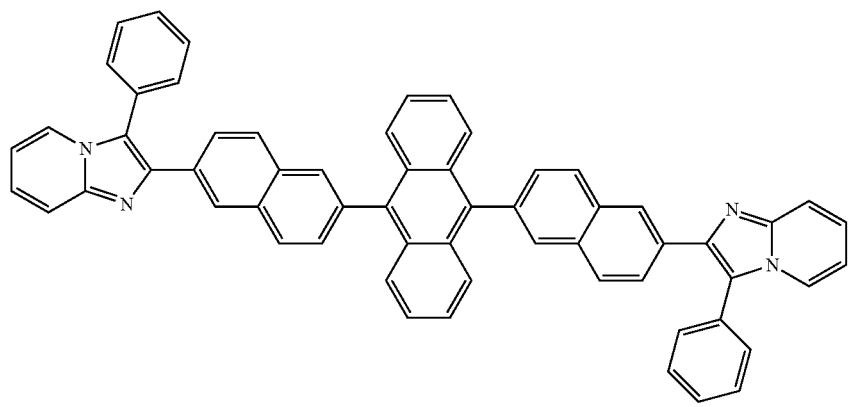
ETL-B8
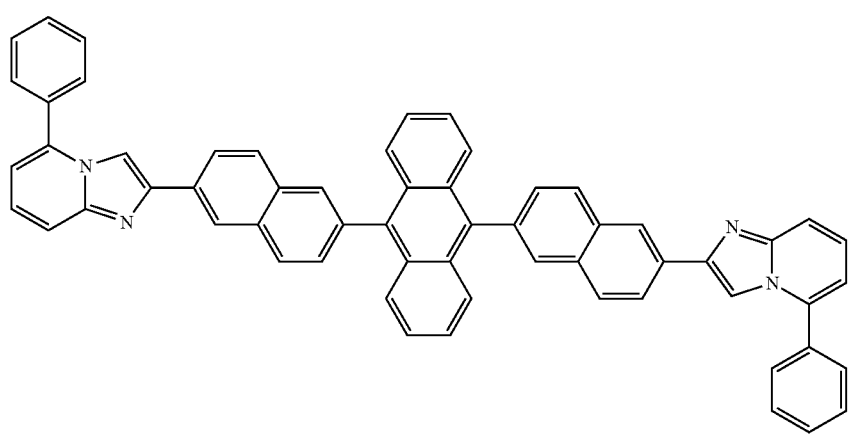
ETL-B9

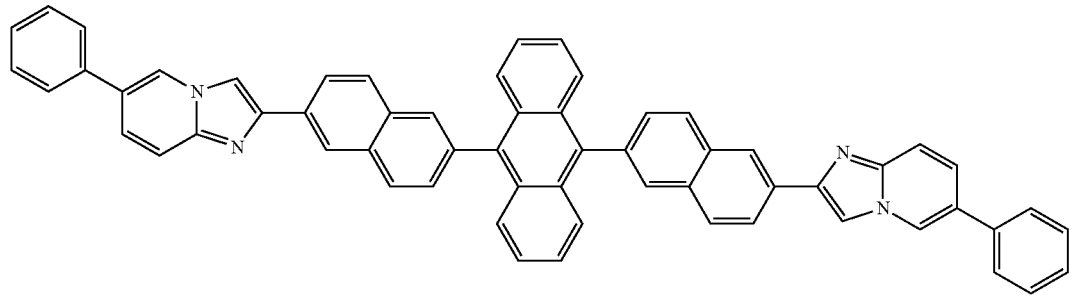
ETL-10
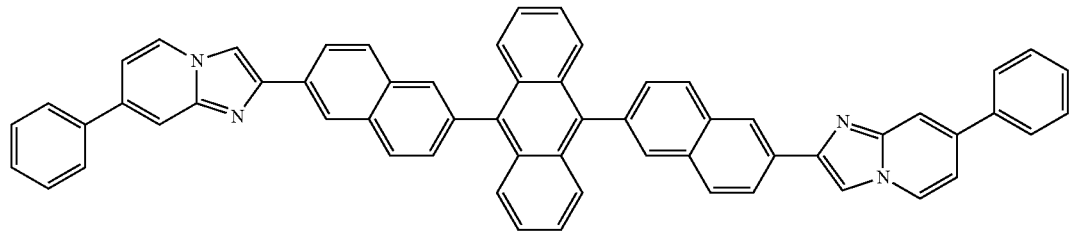
ETL-B11
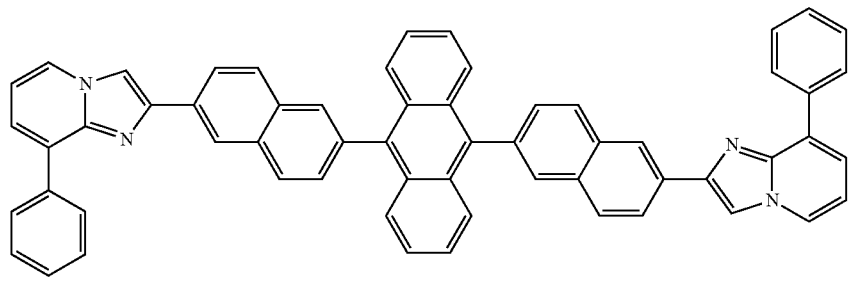
ETL-B12
[Chem. 24]
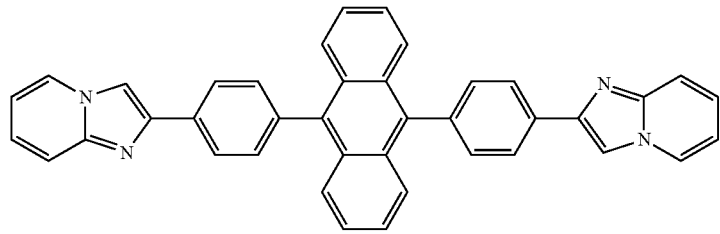
ETL-C1
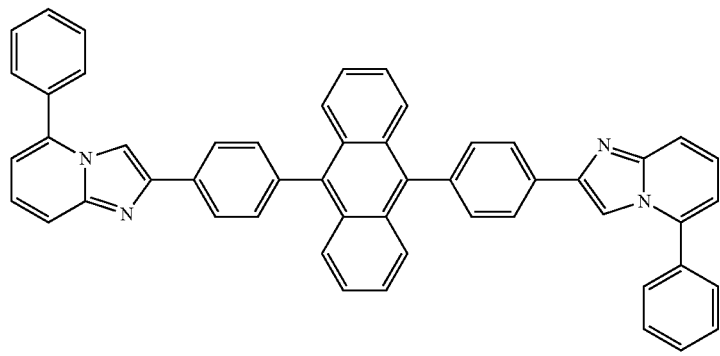
ETL-C2

-continued
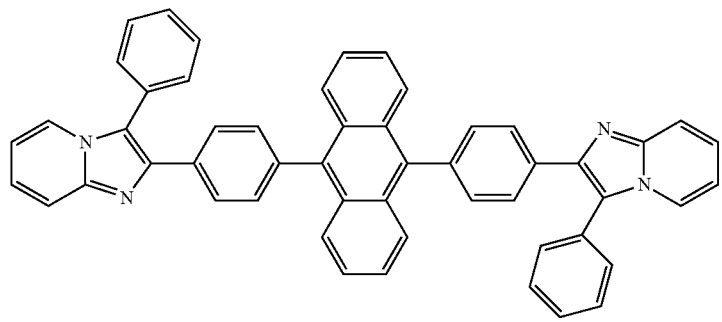
ETL-C3
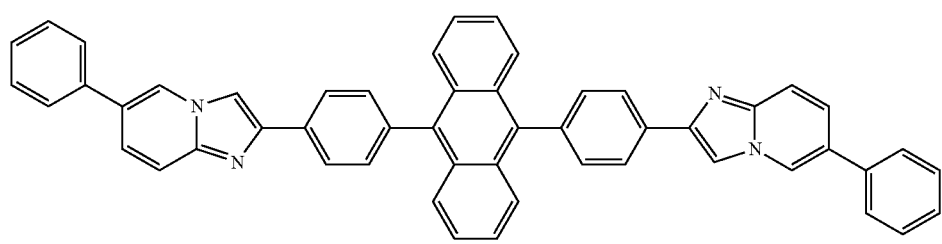
ETL-C4
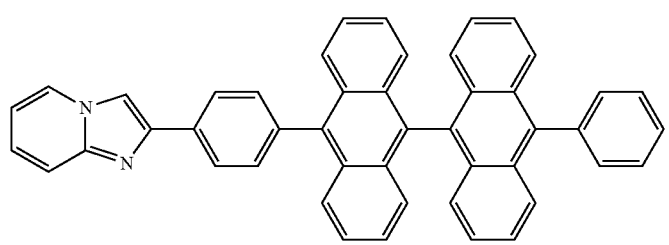
ETL-C5
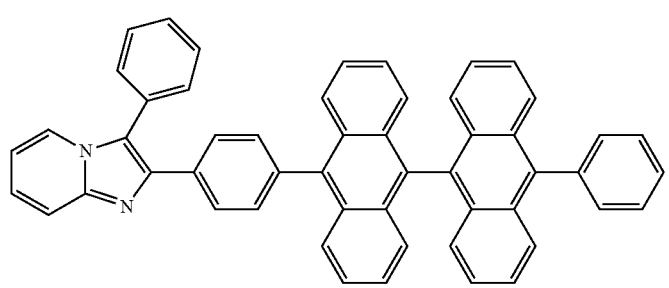
ETL-C6
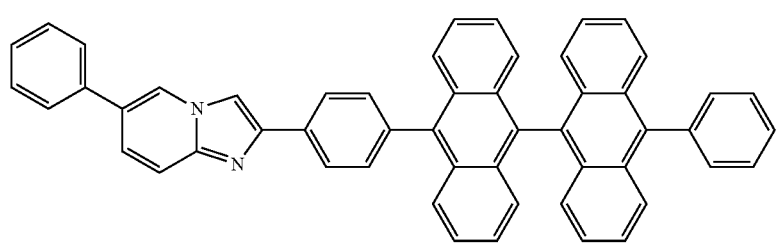
ETL-C7
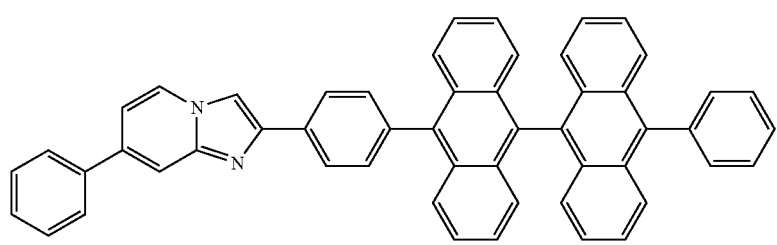
ETL-C8

-continued
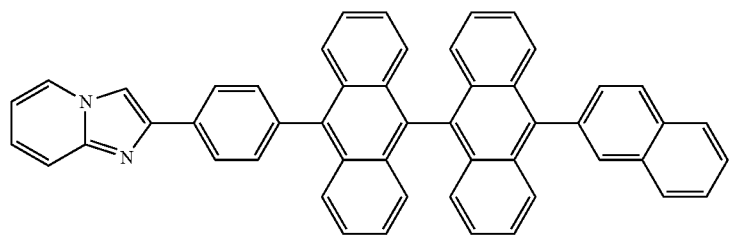
ETL-C9
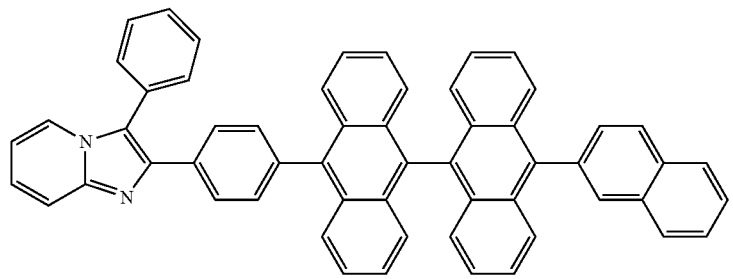
ETL-C10
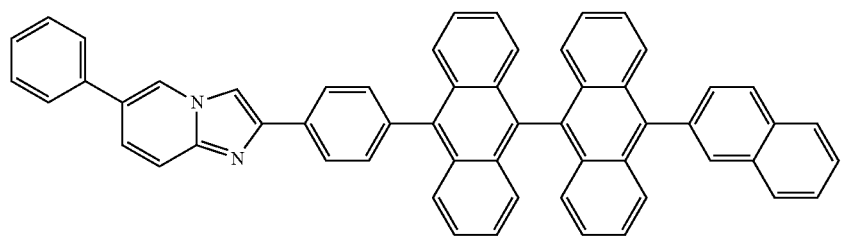
ETL-C11
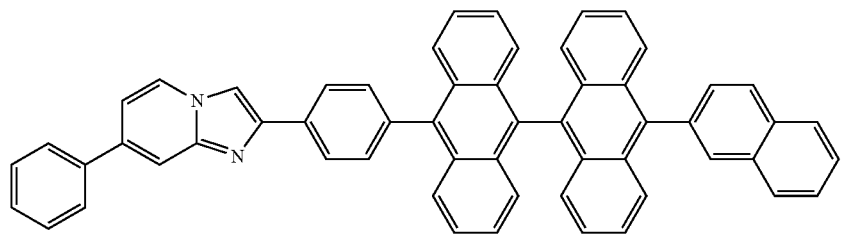
ETL-C12
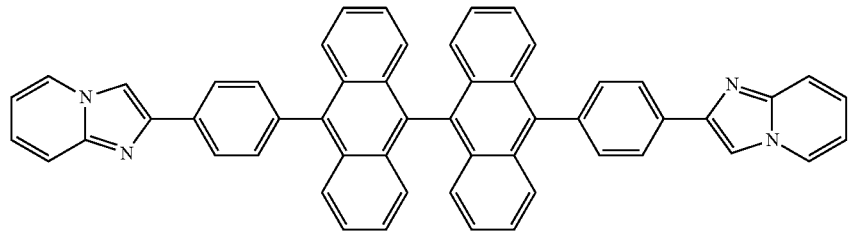
ETL-C13
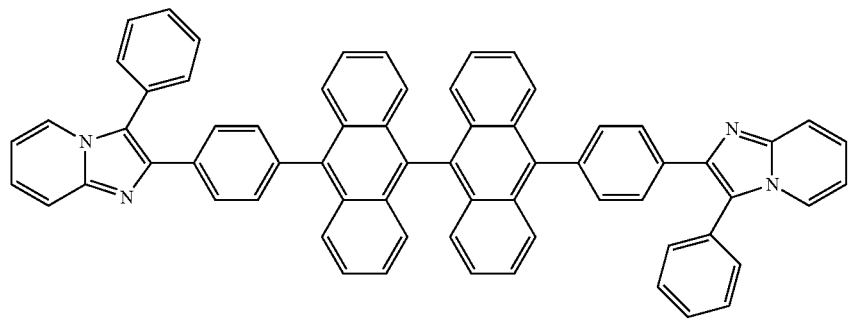
ETL-C14

-continued
ETL-C15
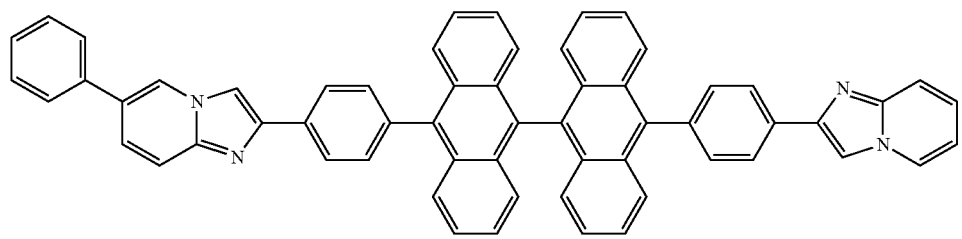
ETL-C16
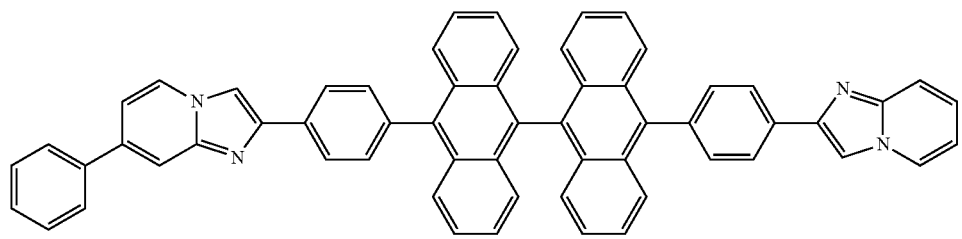
ETL-C17
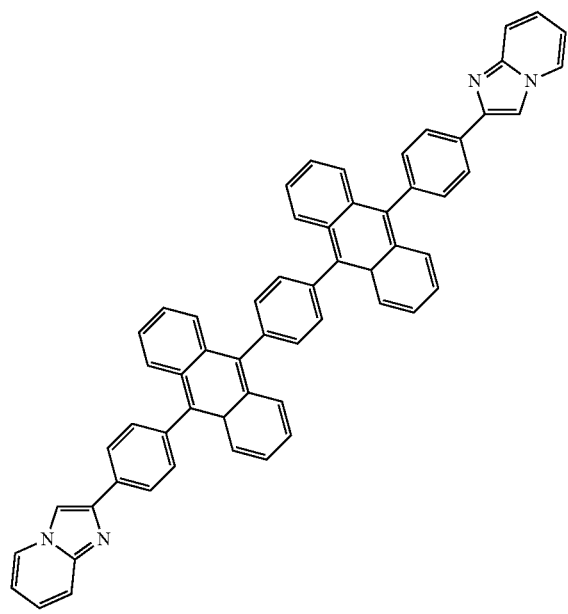
ETL-C18
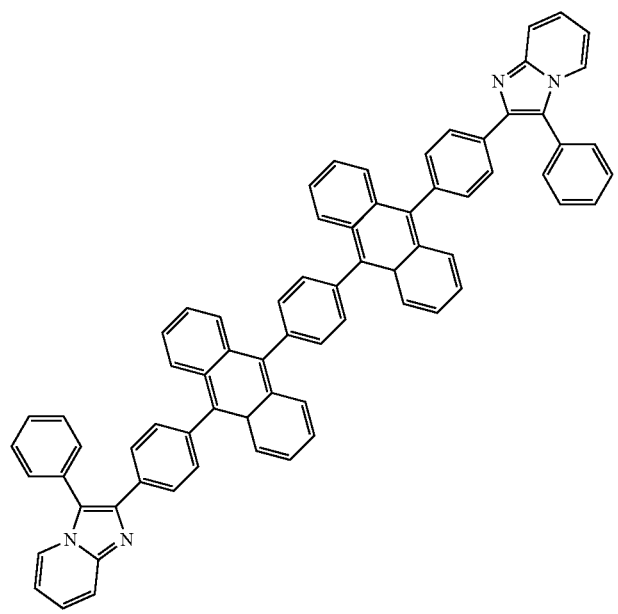

-continued
ETL-C19
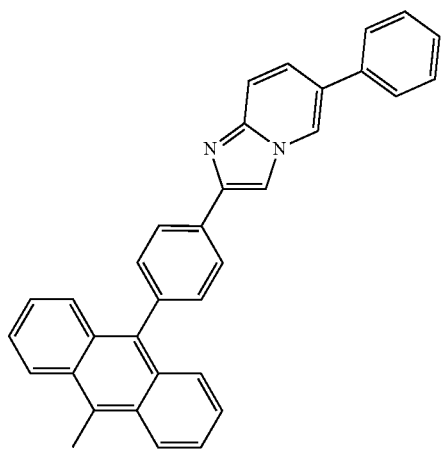
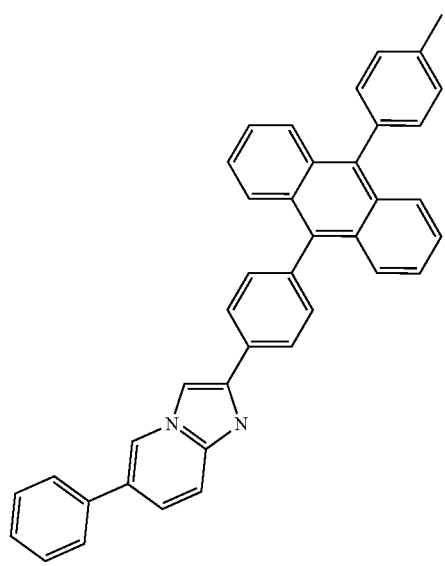
ETL-C20
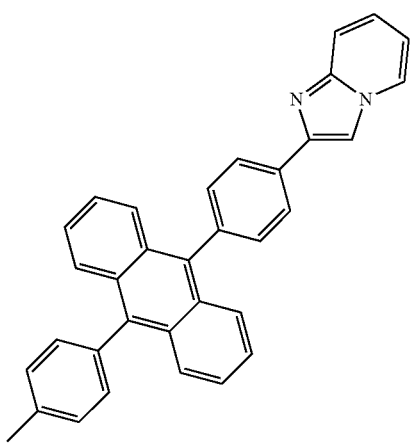

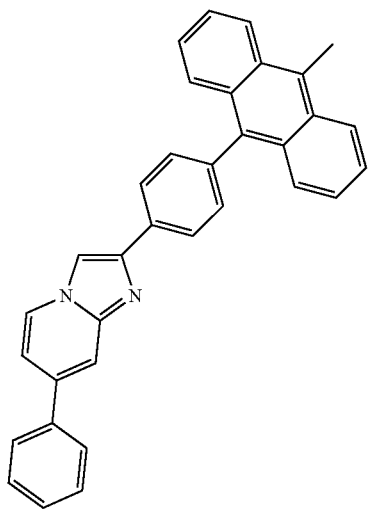

The azaindolizine compound such as this is excellent in terms of the electron transport property and the electron injection property. Therefore, light emitting efficiency of the light emitting element 1 may be increased.

The reason that the electron transport property and the electron injection property of the azaindolizine-based compound such as this are excellent is considered to be as follows.

As described above, in the azaindolizine-based compound having the azaindolizine skeleton and the anthracene skeleton within the molecule, since the entire molecule is connected by a π conjugated system, an electron cloud is spread over the entire molecule.

The azaindolizine skeleton portion in the azaindolizine-based compound such as this also has a function to receive electrons and to deliver the electrons received to the anthracene skeleton portion. Meanwhile, the anthracene skeleton portion in the azaindolizine-based compound such as this has a function to receive electrons from the azaindolizine skeleton portion and to transfer the electrons received to the layer adjacent to the electron transport layer 7 and the anode 3, that is, the light emitting layer 6.

Specifically, the azaindolizine skeleton portion in the azaindolizine-based compound such as this has two nitrogen atoms, a nitrogen atom at one side (near the anthracene skeleton portion) with an $sp^2$ hybrid orbital and a nitrogen atom at the other side (far from the anthracene skeleton portion) with an $sp^3$ hybrid orbital. The nitrogen atom with the sp hybrid orbital, at the same time forms part of the conjugated system of the molecule in the azaindolizine-based compound, functions as a part which accepts the electrons, since a nitrogen atom has a higher electronegativity than a carbon atom and is likely to attract the electrons. On the other hand, the nitrogen atom with the $sp^3$ hybrid orbital, even though it is not a normal conjugated system, since the nitrogen has an unshared electron pair, that these electrons function as a part which transport the electrons toward the conjugated system of the molecule in the azaindolizine-based compound.

On the other hand, the anthracene skeleton in the azaindolizine-based compound, since it is electrically neutral, may easily accept the electrons from the portion of the azaindolizine skeleton. Also, the anthracene skeleton portion in the azaindolizine-based compound easily transfers the electrons to the host material in the light emitting layer 6, since the overlap of the orbital between the anthracene skeleton and the component material of the light emitting layer 6, particularly the host material (acene-based material) is large.

Also, the azaindolizine-based compound such as this, since it is excellent in terms of the electron transport property and the electron injection property as described above, may as a result lower the driving voltage of the light emitting element 1.

Also, the azaindolizine skeleton portion is stable when the nitrogen atom with the $sp^2$ hybrid orbital is reduced and is also stable when the nitrogen atom with the $sp^3$ hybrid orbital is oxidized. For this reason, stability of the azaindolizine-based compound such as this with regard to the electrons and the holes is high. As a result, it is possible to extend the life of the light emitting element 1.

Also, in a case in which the electron transport layer 7 is used as a combination of two or more electron transporting materials as described above, it may be composed of mixed materials of two or more electron transporting materials or may be composed of a stacked layer in which a plurality of layers composed of different electron transporting materials are stacked.

Also, the electron transport layer 7 may include materials other than an azaindolizine-based compound.

In a case in which the electron transport layer 7 is composed of a stacked layer with a plurality of layers, it is preferable that the electron transport layer 7 includes a first electron transport layer which includes the azaindolizine-based compound as described above and a second electron transport layer which is installed between the first electron transport layer and the light emitting layer 6, is in contact with both of these layers and includes a second electron transporting material which is different from the first electron transporting material. As a result, it is possible to extend the life of the light emitting element 1.

Also, in this case, as the second electron transporting material, for example, Alq, a tetracene-based material, and an anthracene-based material or the like may be used. Also, the average thickness of the second electron transport layer, while not particularly limited, is, for example, preferably about 5 nm to 200 nm. As a result, the second electron transport layer forms a mixed layer with the light emitting layer 6 or the part of the first electron transport layer, and therefore, an electron transport property from the electron transport layer 7 to the light emitting layer 6 is favorable and it is possible to extend the life of the light emitting element 1.

The average thickness of the electron transport layer 7 such as this, while not particularly limited, is preferably about 1.0 to 200 nm and more preferably about 10 to 100 nm.

(Electron Injection Layer)

The electron injection layer 8 has a function to increase the efficiency of electron injection from the cathode 9.

As a component material for the electron injection layer 8 (an electron injection material), for example, a variety of inorganic insulation materials and a variety of inorganic semiconductor materials may be used.

As the inorganic insulation material such as this, for example, an alkali metal chalcogenide (an oxide, a sulfide, a selenide, a telluride), an alkaline earth metal chalcogenide, an alkali metal halide, an alkaline earth metal halide or the like may be used and may be used alone or as a combination of two or more. By using these as main materials to form the electron ejection layer 8, it is possible to further improve the electron injection property. In particular, an akali metal compound (an alkali metal chalcogenide, an alkali metal halide or the like) has a very small work function; therefore, by using it to form the electron ejection layer 8, high brightness of the light emitting element 1 may be obtained.

As alkali metal chalcogenides, for example, $Li_2O$, LiO, $Na_2S$, $Na_2Se$, NaO or the like may be used.

As alkaline earth metal chalcogenides, for example, CaO, BaO, SrO, BeO, BaS, MgO, CaSe or the like may be used.

As alkali metal halides, for example, CsF, LiF, NaF, KF, LiCl, KCl, NaCl or the like may be used.

As alkaline earth metal halides, for example, $CaF_2$, $BaF_2$, $SrF_2$, $MgF_2$, $BeF_2$ or the like may be used.

Also, as an inorganic semiconductor material, for example, an oxide, a nitride, a nitride-oxide containing at least one element of Li, Na, Ba, Ca, Sr, Yb, Al, Ga, In, Cd, Mg, Si, Ta, Sb, and Zn may be used and may be used alone or as a combination of two or more.

The average thickness of the electron injection layer 8 such as this, while not particularly limited, is preferably about 0.1 to 1,000 nm, more preferably about 0.2 to 100 nm, and even more preferably about 0.2 to 50 nm.

Also, the electron injection layer 8, depending on the component material or the thickness or the like of the cathode 9 and the electron transport layer 7, may not be included.

(Sealing Member) The sealing member 10 is installed to cover the anode 3, the stacked body 14, and the cathode 9, and has a function to seal them air-tight, and to block the oxygen or moisture. From the installation of the sealing member 10, effects such as improvement of reliability of the light emitting element 1 or prevention of an alteration and degradation (improvement of durability) may be achieved.

As a component material for the sealing member 10, for example, Al, Au, Cr, Nb, Ta, Ti or an alloy containing these, silicon oxide, a variety of resin materials or the like may be used. Also, in a case in which a material with conductivity is used as the component material for the sealing member 10, in order to prevent a short circuit, it is preferable that an insulating film be installed between the sealing member 10 and the anode 3, the stacked body 14, and the cathode 9, if necessary.

Also, the sealing member 10, as a planar type, is placed opposite to the substrate 2, and, for example, the sealant such as a heat-curable resin may be used to seal the gap.

According to the light emitting element 1 described above, along with using the thiadiazole-based material as the light emitting material of the light emitting layer 6, by using the tetracene-based material or the anthracene-based material as the host material of the light emitting layer 6, it is possible to achieve a high efficiency and long life along with emitting light in a near-infrared region.

Also, by using the azaindolizine-based compound as the electron transporting material of the electron transport layer 7, it is possible to achieve a higher efficiency and longer life along with emitting light in a near-infrared region.

The light emitting element 1 described above may be prepared, for example, as follows.

[1] First, the substrate 2 is prepared and the anode 3 is formed on the substrate 2.

The anode 3 may be formed using, for example, a plasma CVD, chemical vapor deposition (CVD) such as a thermal CVD, a dry plating method such as a vacuum deposition, a wet plating method such as an electrolytic plating, a spraying method, a sol-gel method, a MOD method, a metal foil joining or the like.

[2] Next, the hole injection layer 4 is formed on the anode 3.

The hole injection layer 4 is preferably formed from, for example, a vapor phase process using CVD or a dry plating method such as vacuum deposition and sputtering.

Also, the hole injection layer 4 may be formed, for example, as follows. A hole injection layer forming material obtained by dissolving the hole injection material in a solvent or by dispersing into a dispersion medium is supplied on the anode 3 and then is dried (removing the solvent or the dispersion medium).

As a method of supplying the hole injection layer forming material, for example, a variety of coating methods such as a spin coating method, a roll coating method, and an ink jet printing method may be used. These coating methods enable the hole injection layer 4 to be formed relatively easily.

As a solvent or a dispersion medium used to prepare the hole injection layer forming material, for example, a variety of inorganic solvents, a variety of organic solvents or mixed solvents containing these may be used.

Also, the drying may be carried out by, for example, leaving to stand under atmospheric pressure or reduced pressure, a heat treatment, spraying an inert gas or the like.

Also, prior to this step, an oxygen plasma treatment may be made on the upper surface of the anode 3. By doing so, it is possible to impart a lyophilic property on the upper surface of the anode 3, to remove (wash) the organic matter attached to the upper surface of the anode 3, and to adjust a work function near the surface of the anode 3 and the like.

Here, as a condition for the oxygen plasma treatment, for example, it is preferable that a plasma power be about 100 to 800 W, an oxygen gas flow rate be about 50 to 100 mL/min, a transport rate of the treated member (the anode 3) be about 0.5 to 10 mm/sec, and the temperature of the substrate 2 be about 70 to 90° C.

[3] Next, the hole transport layer 5 is formed on the hole injection layer 4.

The hole transport layer 5, is preferably formed from, for example, a vapor phase process using CVD or a dry plating method such as vacuum deposition and sputtering.

A hole transport layer forming material obtained by dissolving the hole transporting material in a solvent or by dispersing into a dispersion medium is supplied on the hole injection layer 4 and then is dried (removing the solvent or the dispersion medium).

[4] Next, the light emitting layer 6 is formed on the hole transport layer 5.

The light emitting layer 6 may be formed from, for example, a vapor phase process using a dry plating method such as a vacuum deposition.

[5] Next, the electron transport layer 7 is formed on the light emitting layer 6.

The electron transport layer 7, is preferably formed from, for example, a vapor phase process using a dry plating method such as vacuum deposition.

An electron transport layer forming material obtained by dissolving the electron transporting material in a solvent or by dispersing into a dispersion medium is supplied on the light emitting layer 6 and then is dried (removing the solvent or the dispersion medium).

[6] Next, the electron injection layer 8 is formed on the electron transport layer 7.

In a case in which an inorganic material is used as the component material for the electron injection layer 8, the electron injection layer 8 may be formed, for example, from a vapor phase process using a CVD or a dry plating method such as vacuum deposition or sputtering, from coating and baking of inorganic ink particles or the like.

[7] Next, the cathode 9 is formed on the electron injection layer 8.

The cathode 9 may be formed from, for example, a vapor deposition method, a sputtering method, metal foil joining, coating or baking of metallic ink particles or the like.

From the processes described above, the light emitting element 1 may be obtained.

Lastly, the sealing member 10 is made to cover the light emitting element 1 obtained and then connect to the substrate 2.

(Light Emitting Device)

Next, a light emitting device according to an embodiment of the present invention will be described with reference to the embodiments.

Figure 2:
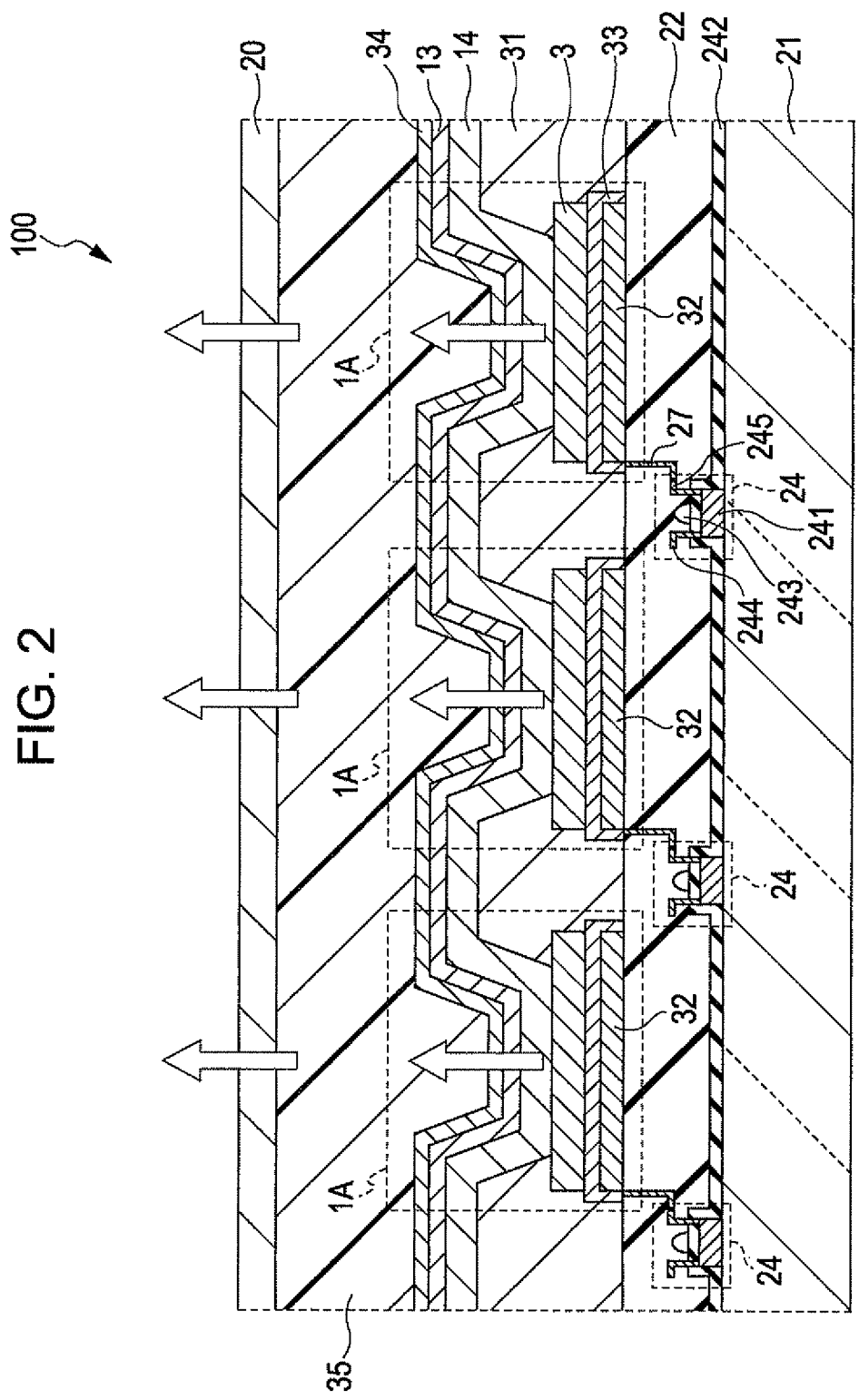
FIG. 2 is a diagram of a longitudinal section which shows a display device to which the light emitting device according to an embodiment of the present invention is applied.

FIG. 2 is a diagram of a longitudinal section which shows a display device to which a light emitting device according to an embodiment of the present invention is applied.

The display device 100 shown in FIG. 2 has a substrate 21, a plurality of light emitting elements 1A, and a plurality of driving transistors 24 to drive each light emitting element 1A respectively. Here, the display device 100 is a display panel with a top emission structure.

On the substrate 21, a plurality of driving transistors 24 are installed and the planarization layer 22 composed of an insulating material is formed so that it covers the driving transistors 24 such as these.

Each driving transistor 24 has a semiconductor layer 241 made of silicon, a gate insulation layer 242 formed on the semiconductor layer 241, a gate electrode 243 formed on the gate insulation layer 242, a source electrode 244, and a drain electrode 245.

On the planarization layer, the light emitting elements 1A are installed corresponding to each driving transistor 24.

In the light emitting elements 1A, a reflective film 32, a corrosion prevention film 33, the anode 3, the stacked body (organic EL light emitting section) 14, the cathode 13, and a cathode cover 34 are stacked on the planarization layer 22 in this order. In the present embodiment, the anode 3 of each light emitting element 1A forms a pixel electrode, and is electrically connected to the drain electrode 245 of each driving transistor 24 through a conductive section (wiring). Also, the cathode 13 of each light emitting element 1A is a normal electrode.

The light emitting elements 1A in FIG. 2 emits light in a near-infrared region.

In the space between the adjacent light emitting elements 1A, a partition 31 is installed. Also, on the light emitting elements 1A such as these, an epoxy layer 35 made of epoxy is formed so as to cover the elements.

Then on the epoxy layer 35, a sealing substrate 20 is installed so as to cover the layer.

As described above, the display device 100 is used as, for example, a near-infrared display used in military applications or the like.

According to the display device 100 such as this, it is possible to emit light in a near-infrared region. Also, the device is excellent in reliability since it is equipped with the light emitting elements 1A with high efficiency and long life.

(Authentication Device)

Next, an authentication device according to an embodiment of the present invention will be described with reference to the embodiments.

Figure 3:
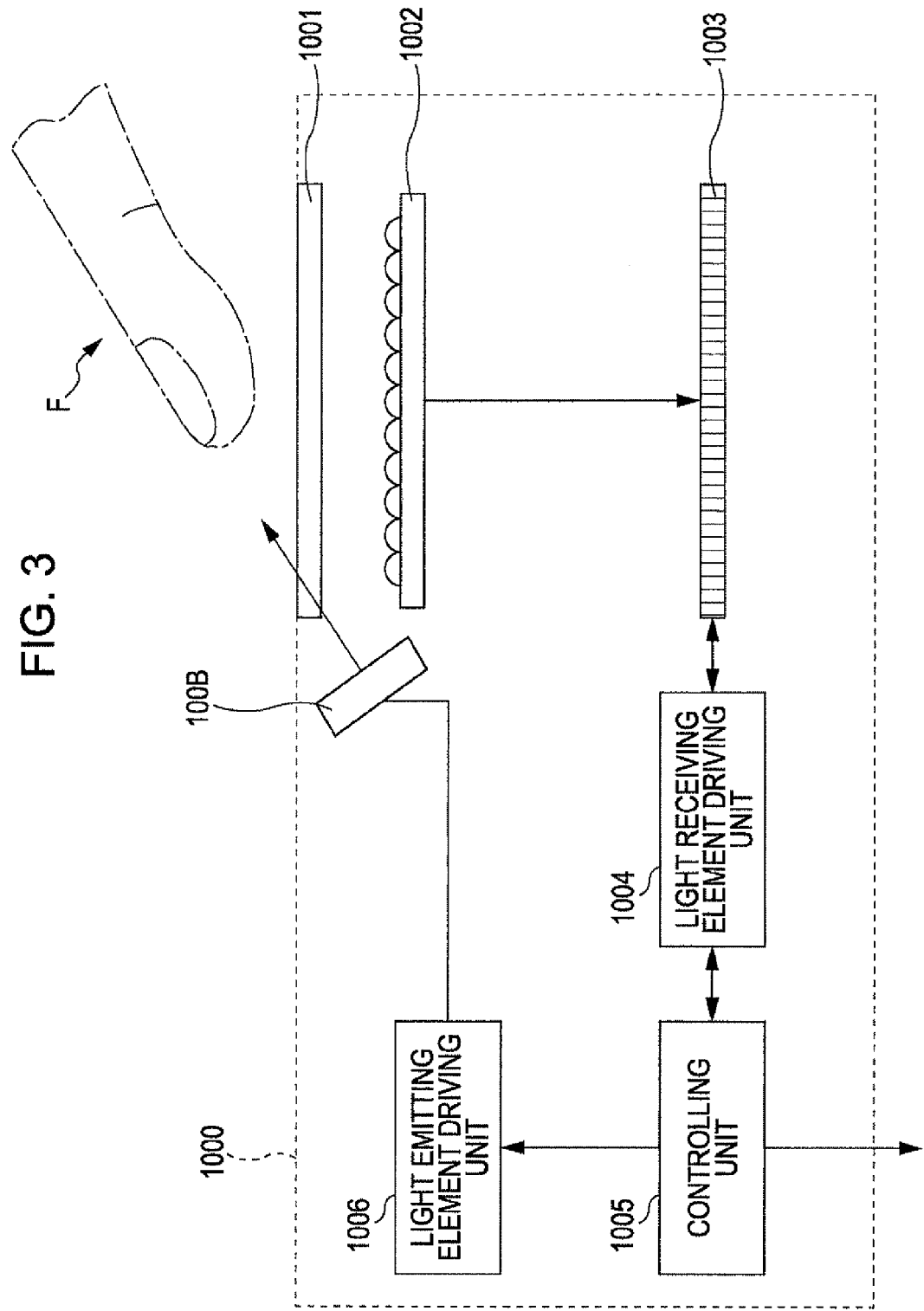
FIG. 3 is a diagram which shows an authentication device according to an embodiment of the present invention.

FIG. 3 is a diagram which shows an authentication device according to an embodiment of the present invention.

The authentication device 1000 shown in FIG. 3 is a biometric authentication device which authenticates a person using biometric information of body F (a fingerprint in the embodiments).

The authentication device 1000 has a light source 100B, a cover glass 1001, a micro-lens array 1002, a light receiving element group 1003, a light emitting element driving unit 1006, a light receiving element driving unit 1004, and a controller unit 1005.

The light source 100B is equipped with a plurality of light emitting elements 1 described above and irradiates a light in a near-infrared region toward the body F which is an object of imaging. For example, a plurality of light emitting elements 1 in this light source 100B is placed along the outer periphery of the cover glass 1001.

The cover glass 1001 is the region where the body F contacts or comes close to.

The micro-lens array 1002 is installed on the opposite side to the side where the body F of the cover glass 1001 contacts or comes close to. This micro-lens array 1002 is configured of a plurality of micro-lenses arranged in a matrix form.

The light receiving element group 1003 is installed on the opposite side to the cover glass 1001 with regard to the micro-lens array 1002. This light receiving element group 1003 is configured of a plurality of light receiving elements arranged in a matrix form corresponding to the plurality of micro-lenses of the micro-lens array 1002. As each light receiving element of this light receiving element group 1003, for example, a CCD (Charge Coupled Device), a CMOS or the like may be used.

The light emitting element driving unit 1006 is a driving circuit which drives the light source 100B.

The light receiving element driving unit 1004 is a driving circuit which drives the light receiving element group 1003.

The controller unit 1005 is, for example, an MPU, and has a function to control the driving of the light emitting element driving unit 1006 and the light receiving element driving unit 1004.

Also, the controller unit 1005 has a function to carry out the authentication of body F, from a light receiving result of the light receiving element group 1003 and from a comparison with the already stored biometric authentication information.

For example, the controller unit 1005 generates an image pattern on body F (for example, a vein pattern) based on the result of light received of the light receiving element group 1003. Then the controller unit 1005 compares the image pattern with an image pattern already stored as biometric authentication information, and carries out the authentication of body F (for example, a vein pattern) based on results of the comparison.

According to the authentication device 1000 such as this, it is possible to carry out a biometric authentication using near-infrared ray. Also, the device is excellent in reliability since it is equipped with the light emitting elements 1 with high efficiency and long life.

The authentication device 1000 such as this may be used to equip a variety of electronic devices.

(Electronic Device)

Figure 4:
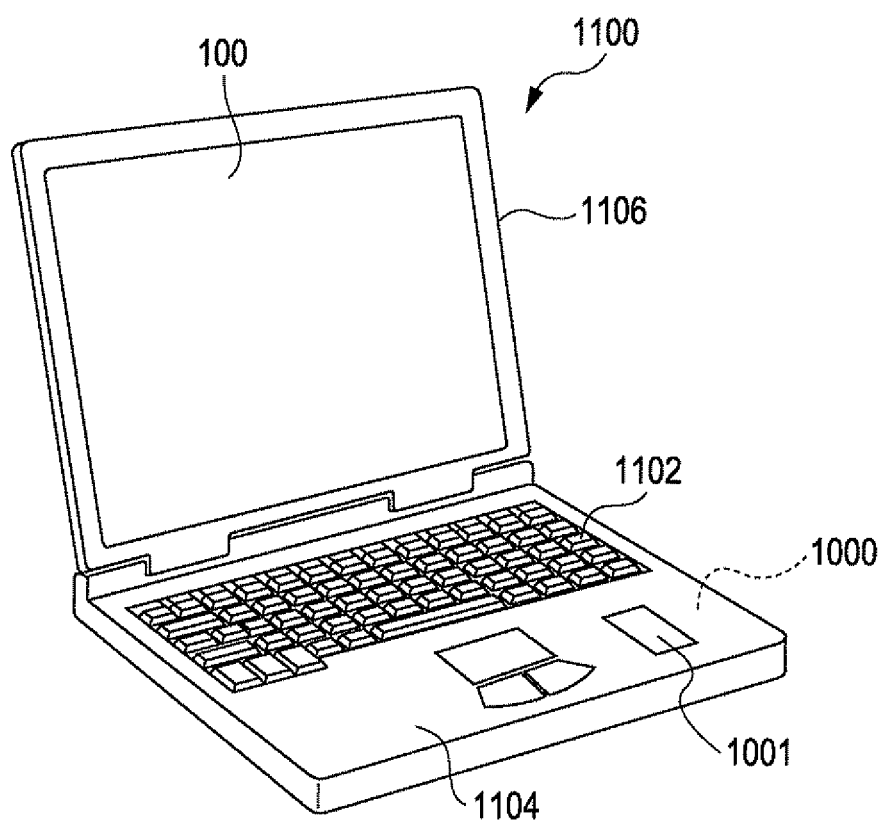
FIG. 4 is a perspective view which shows a configuration of a mobile type (or a lap-top type) personal computer to which an electronic device according to an embodiment of the present invention is applied.

FIG. 4 is a perspective view which shows a configuration of a mobile type (or a lap-top type) personal computer to which an electronic device according to an embodiment of the present invention is applied.

In this drawing, a personal computer 1100 consists of a main unit 1104 equipped with a keyboard 1102, a display unit 1106 equipped with a display section and the display unit 1106 is supported so that it is rotatable with regard to the main unit 1104 through a hinge structure unit.

In this personal computer 1100, the main unit 1104 is equipped with the authentication device 1000 described above.

The personal computer 1100 such as this is excellent in reliability since the light emitting elements 1 with high efficiency and long life are equipped.

Also, the electronic device according to an embodiment of the present invention, in addition to a personal computer (a mobile personal computer) in FIG. 4, may be applied to, for example, a mobile phone, a digital still camera, a television or a video camera, a viewfinder type or direct-view monitor type videotape recorder, a laptop personal computer, a car navigation device, a pager, an electronic organizer (including a communication function unit), an electronic dictionary, a calculator, an electronic games device, a word processor, a workstation, a video phone, a television monitor for security, electronic binoculars, a POS terminal, a device equipped with a touch panel (for example, a cash dispenser of a financial institution, or a vending machine), a medical device (for example, an electronic thermometer, a blood pressure meter, a blood glucose meter, a pulse measuring device, a pulse wave measuring device, an electrocardiograph display device, an ultrasonic diagnostic device, or an endoscope display device), a fishfinder, a variety of measuring devices, gauges (for example, gauges of a vehicle, an aircraft, or a ship), a flight simulator, a projection-type display device such as a variety of monitors or a projector, or the like.

Hereinbefore, the thiadiazole-based compound, the light emitting element compound, the light emitting element, the light emitting device, the authentication device, and the electronic device according to the embodiments of the present invention have been described with reference to the preferred embodiments shown in the accompanying drawings, however, the present invention is not limited to these embodiments.

For example, the light emitting element and the light emitting device according to the embodiments of the present invention may also be used as a light source for illumination.

EXAMPLES

Hereinafter, the present invention will be described with reference to specific examples.

1. Production of the Thiadiazole-Based Compound

Synthesis Example A1

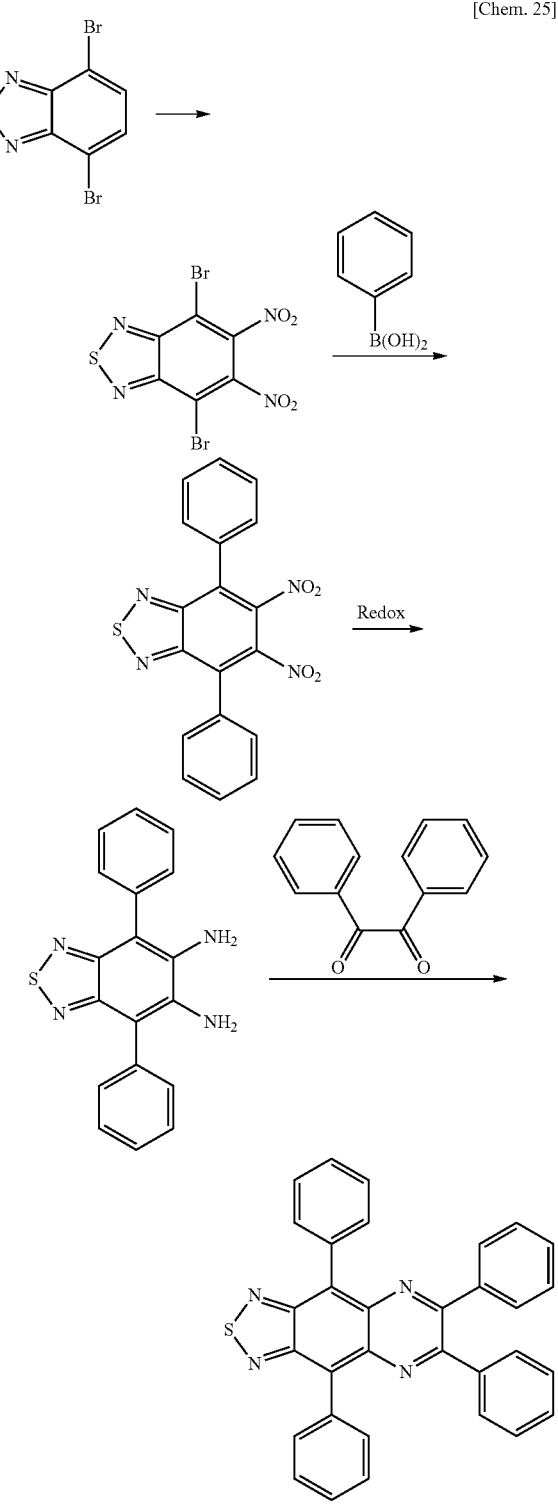

[Chem. 25]

Synthesis (A1-1)

1500 ml of fuming nitric acid was placed in a 5 liter flask and was cooled. 1500 ml of sulfuric acid was added in portions to the nitric acid while the temperature was maintained at 10 to 50° C. 150 g of dibromobenzothiadiazole compound (a) as a raw material was added thereto in small portions over 1 hour while the temperature of the solution was kept at equal to or less than 5° C. After the whole amount was added, the solution was allowed to react for 20 hours at room temperature (25° C.). After the reaction, the reaction mixture was poured into 3 kg of ice and was stirred overnight. After that, it was filtered and washed with methanol and heptane.

After the residue from the filtration was dissolved by heating in 200 ml of toluene, it was slowly cooled to room temperature and was filtered. After the residue was washed with a small amount of toluene, it was dried under reduced pressure.

As a result, 60 g of a compound (b) (4,7-dibromo-5,6-dinitrobenzo[1,2,5]thiadiazole) with a 95% purity by HPLC was obtained.

Synthesis (A1-2)

Under an argon (Ar) atmosphere, 30 g of the dibromo product compound (b), 23 g of phenylboronic acid (commercially available product), 2500 ml of toluene, 2M cesium carbonate aqueous solution (152 g/(distilled water) 234 ml) were placed in a 5 liter flask and were allowed to react overnight at 90° C. After the reaction, it was filtered, separated, concentrated, and the resulting 52 g of crude product was separated using a silica-gel column (SiO$_2$ 5 kg) and a purple-red solid was obtained.

As a result, 6 g of a compound (c) (5,6-dinitro-4,7-diphenylbenzo[1,2,5]thiadiazole) with a 96% purity by HPLC was obtained.

Synthesis (A1-3)

Under an argon (Ar) atmosphere, 6 g of the dinitro-based compound (c), 7 g of reduced iron, and 600 ml of acetic acid were placed in a 1 liter flask, were allowed to react for 4 hours at 80° C., and were cooled to room temperature. After the reaction, the reaction solution was poured into 1.5 liters of ion-exchanged water and 1.5 liters of ethyl acetate was additionally added. After the addition, a solid was precipitated, therefore, by adding 1 liter of tetrahydrofuran and 300 g of table salt, the liquid was separated. The aqueous layer was re-extracted with 1 liter of tetrahydrofuran. By being concentrated, dried and washed again with small amount of water and methanol, an orange solid was obtained.

As a result, 7 g of a compound (d) (4,7-diphenylbenzo[1,2,5]thiadiazole-5,6-diamine) with an 80% purity by HPLC was obtained.

Synthesis (A1-4)

Under an argon (Ar) atmosphere, 4.5 g of the diamine product compound (d), 3.7 g of benzil, and 300 ml of acetic acid as a solvent were placed in a 1 liter flask, and were allowed to react for 2 hours at 80° C. After the reaction, the reaction mixture was cooled to room temperature, was poured into 1 liter of ion-exchanged water, crystals were filtered, washed with water and 7 g of a black-green solid was obtained. Then, the black-green solid was purified using a silica-gel column (SiO$_2$ 1 kg).

As a result, 4 g of a compound (e) (a compound expressed by the Formula D-1) with a 99% purity by HPLC was obtained. The result of mass analysis of this compound (e) was, M+: 492.

Also, the compound (e) obtained was purified by sublimation at the set temperature of 340° C. The purity of the compound (e) by HPLC was 99% after the purification by sublimation.

Synthesis Example A2

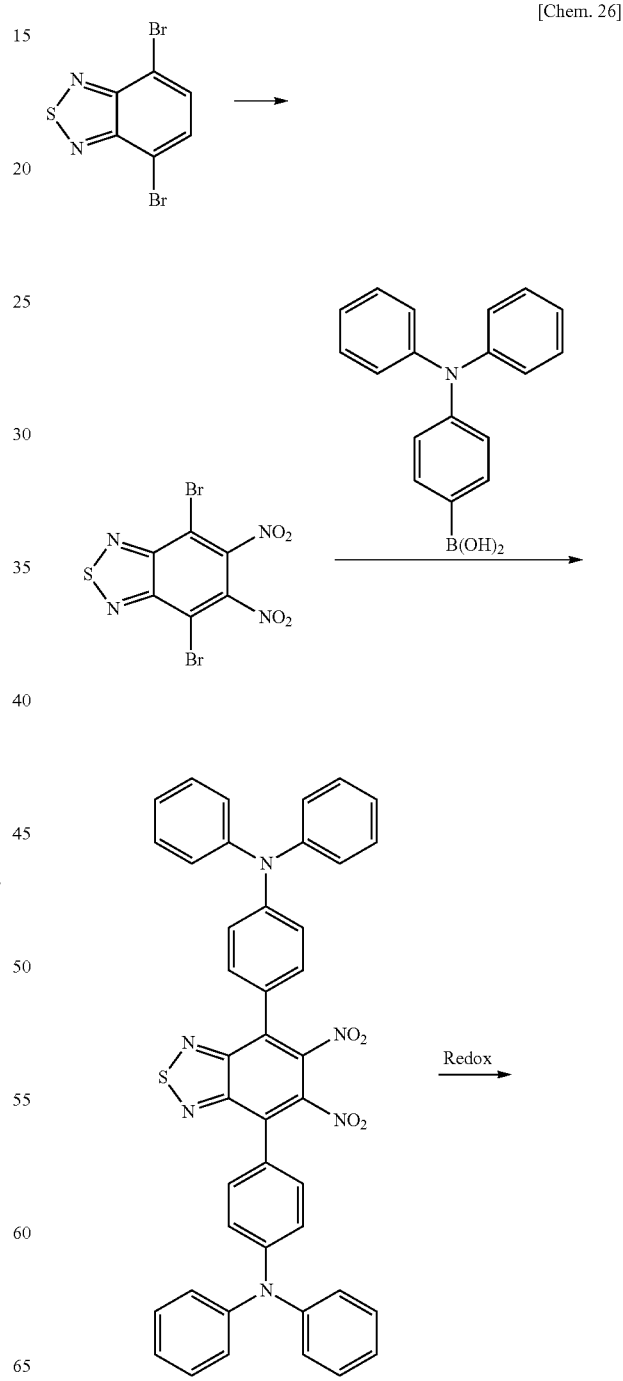

[Chem. 26]

-continued

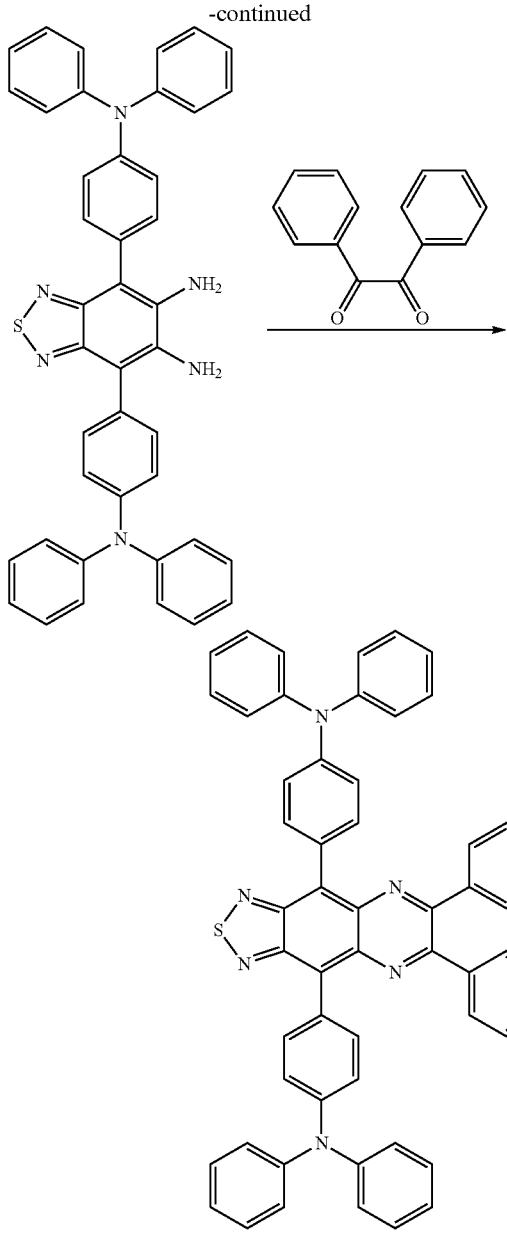

The synthesis was carried out in the same manner as that of the synthesis example A1 described above, except for triphenylamineboronic acid product which was used instead of phenylboronic acid used in synthesis (A1-2) of the synthesis example A1 described above. A compound (h) expressed by the Formula D-2 was obtained by this process.

Here, triphenylamineboronic acid product was synthesized as follows. Under an argon (Ar) atmosphere, 246 g of 4-bromotriphenylamine (commercially available product), and 1500 ml of anhydrous tetrahydrofuran were placed in a 5 liter flask, and 570 ml of 1.6M n-BuLi/hexane solution was added dropwise over 3 hours at −60° C. After 30 minutes, 429 g of triisopropylborate was added dropwise over 1 hour. Then, it was allowed to react overnight at ambient temperature. After the reaction, 2 liters of water was added dropwise, and after that, the mixture was extracted and the liquid was separated using 2 liters of toluene. The organic layer was concentrated, recrystallized, filtered, dried and 160 g of white boronic acid product, a target compound, was obtained.

The purity of the boronic acid product obtained by HPLC was 99%.

Using the boronic acid product obtained, a compound (f) was also obtained by a synthesis carried out in the same manner as that of the synthesis (A1-2) of the synthesis example A1 described above.

Using the compound (f) obtained, a compound (g) was also obtained by a synthesis carried out in the same manner as that of the synthesis (A1-3) of the synthesis example A1 described above.

Using the compound (g) obtained, a compound (h) expressed by the Formula D-2 was also obtained by a synthesis carried out in the same manner as that of the synthesis (A1-4) of the synthesis example A1 described above.

Synthesis Example A3

[Chem. 27]

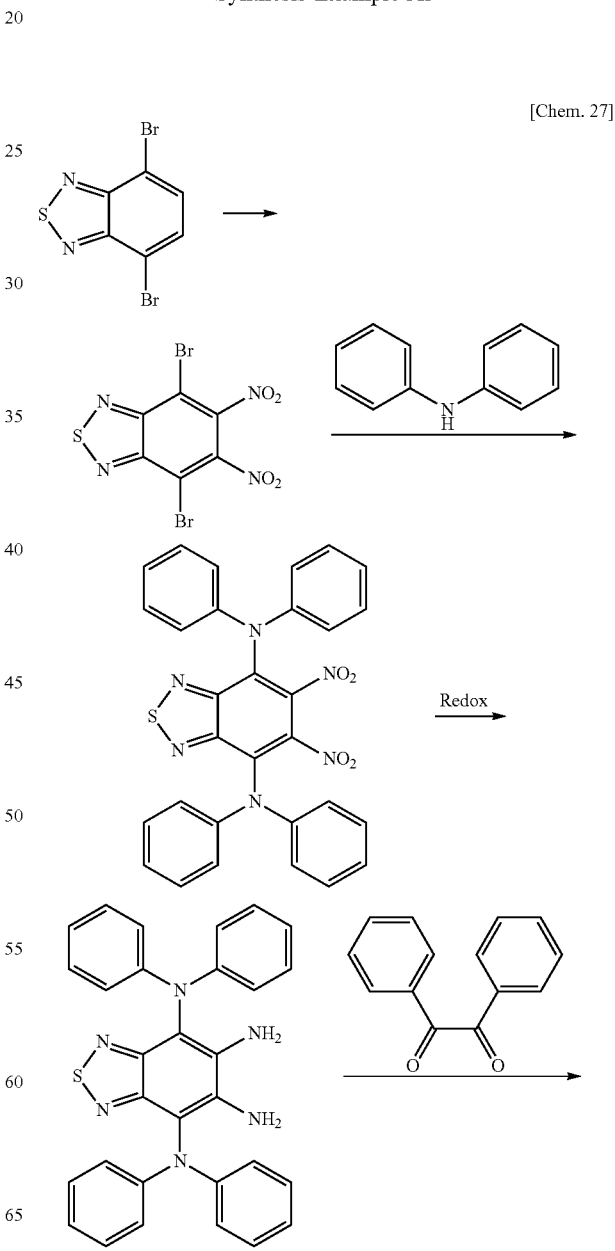

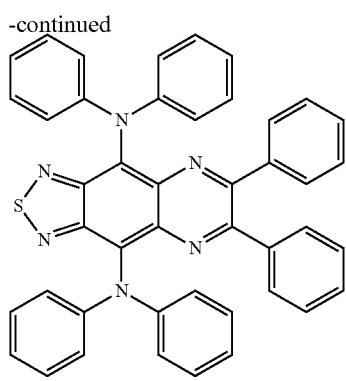

The synthesis was carried out in the same manner as that of the synthesis example A1 described above, except for diphenylamine which was used instead of phenylboronic acid used in synthesis (A1-2) of the synthesis example A1 described above. A compound (k) represented by the Formula D-3 was obtained by this process.

Here, the synthesis using diphenylamine was carried out as follows. Under an argon (Ar) atmosphere, 11 g of palladium(0) tetrakistriphenyl was dissolved in 100 ml of toluene in a 300 ml flask and was heated to 100° C. 8 g of tri-t-butylphosphine was added thereto, the reaction mixture was allowed to react for 30 minutes, and was used as a catalyst (Pd catalyst).

Meanwhile, under an argon (Ar) atmosphere, 30 g of dibromo product compound (b), and 33 g of diphenylamine (commercially available product) were dissolved in 2500 ml of toluene in a 5 liter flask and was heated to 100° C. The already adjusted Pd catalyst and 20 g of t-BuOK were added thereto and the reaction mixture was heated under reflux for 3 hours.

After the reaction, it was cooled to room temperature, and 100 ml of water was added. After the mixture was stirred for approximately 1 hour, water was separated using a separation funnel and the organic layer was dried, resulting in a solid. The solid obtained was separated by a silica-gel column ($SiO_2$ 5 kg), and a purple solid was obtained.

As a result, 10 g of a compound (i) (5,6-dinitro-N,N,N', N'-tetraphenylbenzo[1,2,5]thiadiazole) with a 96% purity by HPLC was obtained.

Using the compound (i) obtained, a compound (j) was also obtained by a synthesis carried out in the same manner as that of the synthesis (A1-3) of the synthesis example A1 described above.

Using the compound (j) obtained, a compound (k) represented by the Formula D-3 was also obtained by a synthesis carried out in the same manner as that of the synthesis (A1-4) of the synthesis example A1 described above.

2. Production of Host Material (Tetracene-Based Material) (Synthesis Example B1) Synthesis of a Compound Expressed by Formula H1-2

[Chem. 28]

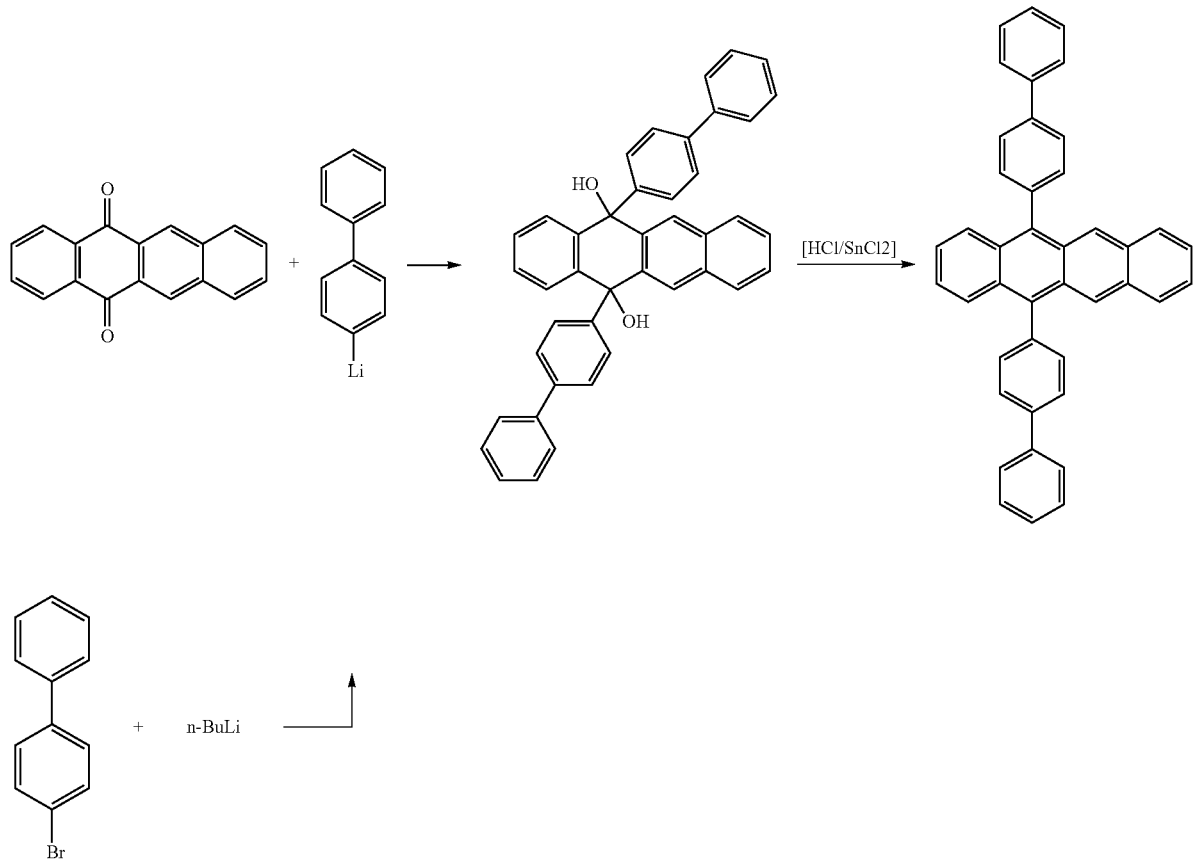

Synthesis (B1-1)

Under an argon (Ar) atmosphere, 6 g of 4-bromobiphenyl and 50 ml of dry diethyl ether were placed in a 300 ml flask. At room temperature, 14.5 ml of 1.6M n-BuLi/hexane solution was added dropwise and the reaction mixture was allowed to react for 30 minutes.

Meanwhile, separately, under an argon (Ar) atmosphere, 2.7 g of 5,12-naphthacenequinone and 100 ml of dry toluene were placed in a 500 ml flask. The already adjusted biphenyllithium was added dropwise thereto and the reaction mixture was allowed to react for 3 hours. After the reaction, 20 ml of distilled water was added, was stirred for 30 minutes, and after the reaction mixture was placed in methanol, the solid was filtered and separated. The solid obtained was purified with silica-gel ($SiO_2$ 500 g).

As a result, 4.5 g of a white solid (5,12-bisbiphenyl-4-yl-5,12-dihydronaphthacene-5,12-diol) was obtained.

Synthesis (B1-2)

4.5 g of the diol product obtained from the synthesis (B1-1) and 300 ml of acetic acid were weighed and placed in a 1000 ml of flask. 5 g of tin chloride (II) (anhydrous) dissolved in 5 g of hydrochloric acid (35%) was added thereto and the mixture was stirred for 30 minutes. After that, the mixture was transferred to a separatory funnel, separated and washed in distilled water by adding toluene, and was dried. The solid obtained was purified with silica-gel ($SiO_2$ 500 g) resulting in 4 g of a yellow solid (a compound expressed by the Formula H1-2).

(Synthesis Example B2) Synthesis of a Compound Expressed by Formula H1-5

Synthesis (B2-1)

Under an argon (Ar) atmosphere, 6 g of 4-bromo-[1,1';3',1"]terphenyl and 50 ml of dry diethyl ether were placed in a 300 ml flask. At room temperature, 14.5 ml of 1.6M n-BuLi/hexane solution was added dropwise and the reaction mixture was allowed to react for 30 minutes.

Meanwhile, separately, under an argon (Ar) atmosphere, 2 g of 5,12-naphthacenequinone and 100 ml of dry toluene were placed in a 500 ml flask. The already adjusted terphenyllithium was added dropwise thereto and the reaction mixture was allowed to react for 3 hours. After the reaction, 20 ml of distilled water was added, was stirred for 30 minutes, and after the reaction mixture was placed in methanol, the solid was filtered and separated. The solid obtained was purified with silica-gel ($SiO_2$ 500 g).

As a result, 5 g of a white solid (5,12-bis-[1,1';3',1"]terphenyl-4'-yl-5,12-dihydronaphthacene-5,12-diol) was obtained.

Synthesis (B2-2)

5 g of the diol product obtained from the synthesis (B2-1) and 300 ml of acetic acid were weighed and placed in a 1000 ml of flask. 5 g of tin chloride (II) (anhydrous) dissolved in 5 g of hydrochloric acid (35%) was added thereto and the mixture was stirred for 30 minutes. After that, the mixture was transferred to a reparatory funnel, separated and washed in distilled water by adding toluene, and was dried. The solid obtained was purified with silica-gel ($SiO_2$ 500 g) resulting in 4.5 g of a yellow solid (a compound represented by the Formula H1-5).

[Chem. 29]

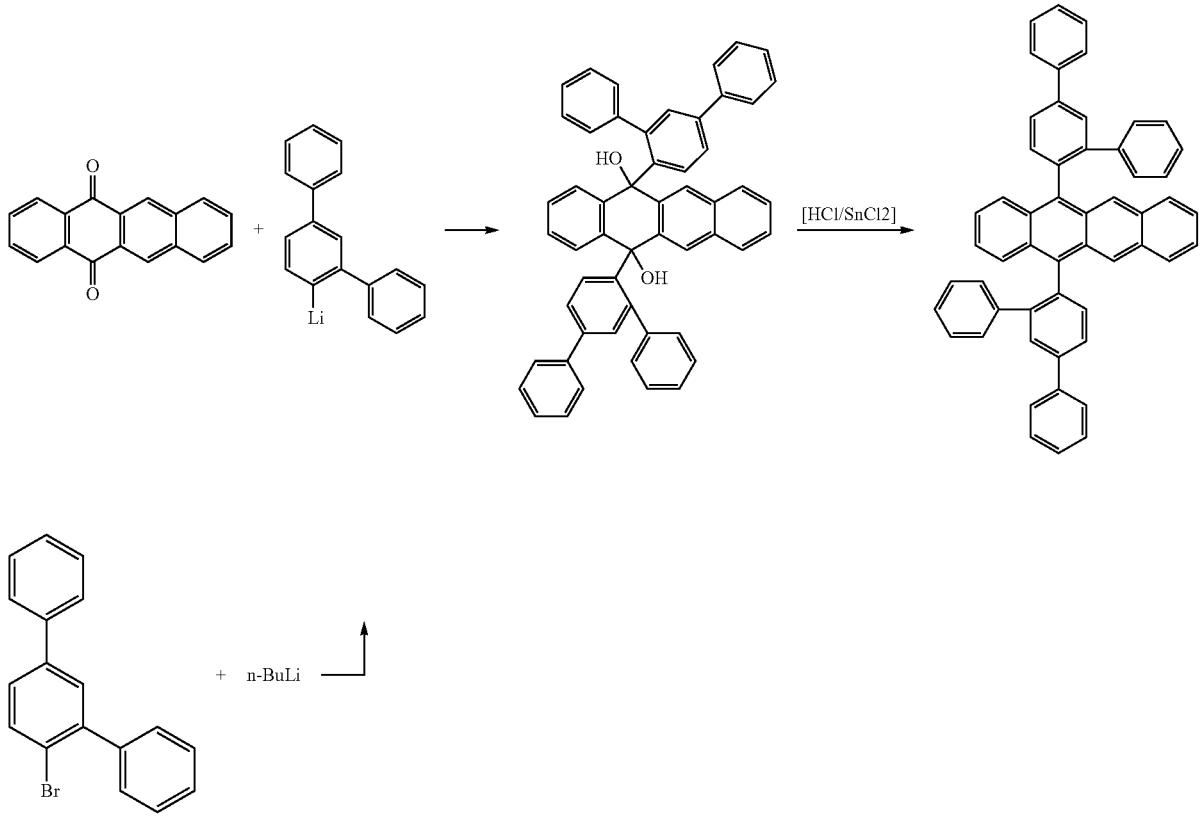

(Synthesis Example B3) Synthesis of a Compound Represented by Formula H1-13

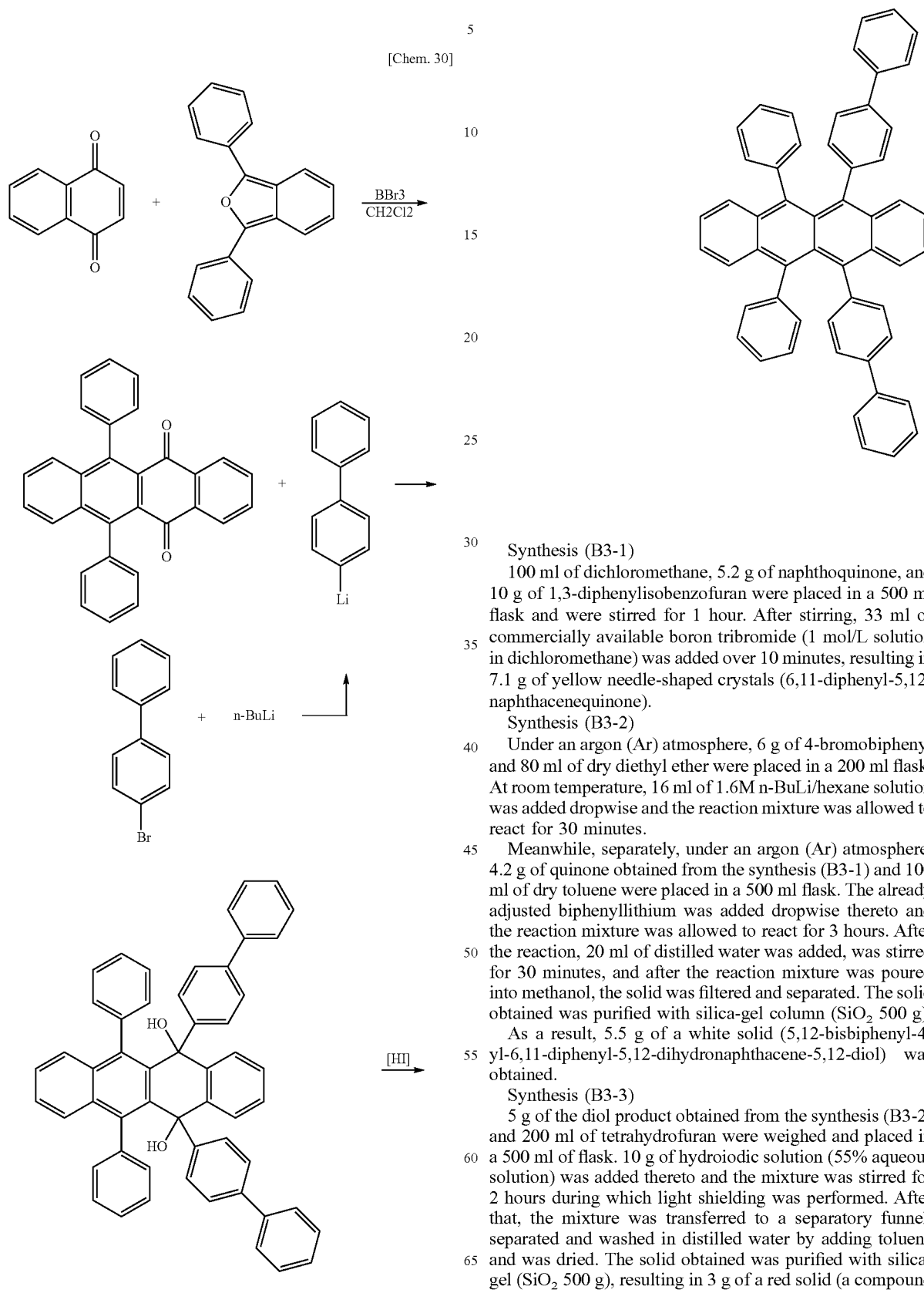

Synthesis (B3-1)

100 ml of dichloromethane, 5.2 g of naphthoquinone, and 10 g of 1,3-diphenylisobenzofuran were placed in a 500 ml flask and were stirred for 1 hour. After stirring, 33 ml of commercially available boron tribromide (1 mol/L solution in dichloromethane) was added over 10 minutes, resulting in 7.1 g of yellow needle-shaped crystals (6,11-diphenyl-5,12-naphthacenequinone).

Synthesis (B3-2)

Under an argon (Ar) atmosphere, 6 g of 4-bromobiphenyl and 80 ml of dry diethyl ether were placed in a 200 ml flask. At room temperature, 16 ml of 1.6M n-BuLi/hexane solution was added dropwise and the reaction mixture was allowed to react for 30 minutes.

Meanwhile, separately, under an argon (Ar) atmosphere, 4.2 g of quinone obtained from the synthesis (B3-1) and 100 ml of dry toluene were placed in a 500 ml flask. The already adjusted biphenyllithium was added dropwise thereto and the reaction mixture was allowed to react for 3 hours. After the reaction, 20 ml of distilled water was added, was stirred for 30 minutes, and after the reaction mixture was poured into methanol, the solid was filtered and separated. The solid obtained was purified with silica-gel column ($SiO_2$ 500 g).

As a result, 5.5 g of a white solid (5,12-bisbiphenyl-4-yl-6,11-diphenyl-5,12-dihydronaphthacene-5,12-diol) was obtained.

Synthesis (B3-3)

5 g of the diol product obtained from the synthesis (B3-2) and 200 ml of tetrahydrofuran were weighed and placed in a 500 ml of flask. 10 g of hydroiodic solution (55% aqueous solution) was added thereto and the mixture was stirred for 2 hours during which light shielding was performed. After that, the mixture was transferred to a separatory funnel, separated and washed in distilled water by adding toluene and was dried. The solid obtained was purified with silica-gel ($SiO_2$ 500 g), resulting in 3 g of a red solid (a compound represented by the Formula H1-13).

3. Production of Host Material (Anthracene-Based Material) (Synthesis Example C1) Synthesis of a Compound Expressed by Formula H2-34

After 3 hours, extraction with toluene was carried out in a separatory funnel and purification using silica gel (SiO$_2$ 500 g) was carried out.

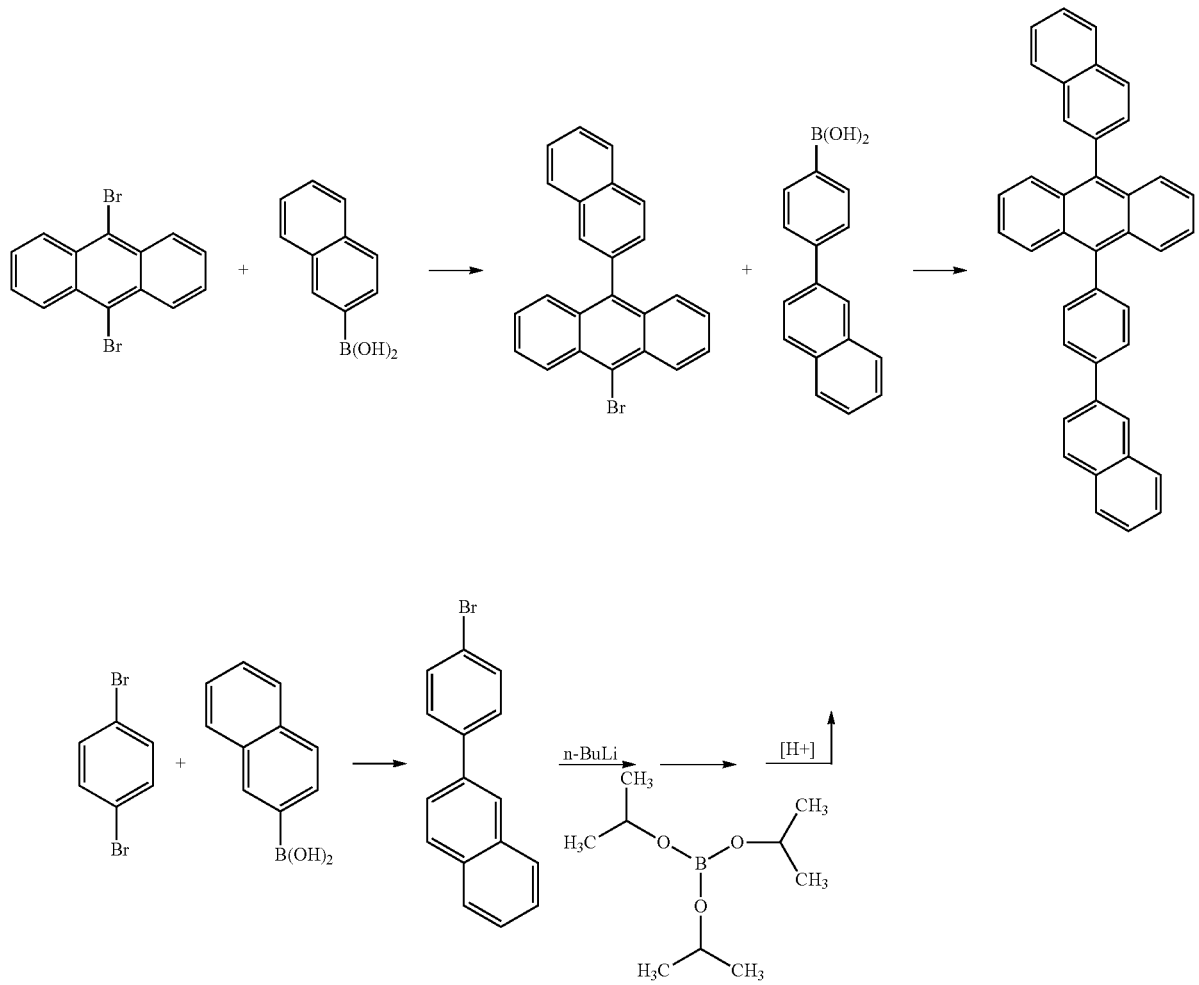

[Chem. 31]

Synthesis (C1-1)

2.1 g of commercially available 2-naphthaleneboronic acid and 5 g of 9,10-dibromoanthracene were dissolved in 50 ml of dimethoxyethane and were heated to 80° C. 50 ml of distilled water and 10 g of sodium carbonate were added thereto. Also, 0.4 g of tetrakis-triphenylphosphine palladium (0) was added thereto.

After 3 hours, extraction with toluene was carried out in a separatory funnel and purification using silica gel (SiO$_2$ 500 g) was carried out.

As a result, 3 g of pale yellow crystals (9-bromo-10-naphthalen-2-yl-anthracene) was obtained.

Synthesis (C1-2)

Under an Ar atmosphere, in a 500 ml flask, 10.5 g of commercially available 2-naphthaleneboronic acid and 17.5 g of 1,4-dibromobenzene were dissolved in 250 ml of dimethoxyethane and were heated to 80° C. 250 ml of distilled water and 30 g of sodium carbonate were added thereto. Also, 2 g of tetrakis-triphenylphosphine palladium (0) was added thereto.

As a result, 10 g of white crystals (2-(4-bromophenyl)-naphthalene) was obtained.

Synthesis (C1-3)

Under an Ar atmosphere, 10 g of (2-(4-bromophenyl)-naphthalene) obtained from synthesis (C1-2) and 500 ml of anhydrous tetrahydrofuran were placed in a 1 liter flask, and 22 ml of 1.6 M n-BuLi/hexane solution was added dropwise over 30 minutes at −60° C. After 30 minutes, 7 g of triisopropyl borate was added. After the dropwise addition, reaction overnight at ambient temperature was performed. After the reaction, 100 ml of water was added dropwise, and after that, the mixture was extracted and the liquid was separated using 2 liters of toluene. The organic layer was concentrated, recrystallized, filtered, dried and 5 g of white phenylboronic acid derivative was obtained.

Synthesis (C1-4)

Under an Ar atmosphere, in a 500 ml flask, 3 g of 9-bromo-10-naphthalen-2-yl-anthracene obtained from synthesis (C1-1) and 3 g of boronic acid obtained from synthesis (C1-3) were dissolved in 200 ml of dimethoxyethane and were heated to 80° C. 250 ml of distilled water and 10 g of sodium carbonate were added thereto. Also, 0.5 g of tetrakis-triphenylphosphine palladium(0) was added thereto.

After 3 hours, extraction with toluene was carried out in a separatory funnel and purification using silica gel chromatography was carried out.

As a result, 3 g of pale off-white solid (a compound expressed by the Formula H2-34) was obtained.

(Synthesis Example C2) Synthesis of a Compound Expressed by Formula H2-61

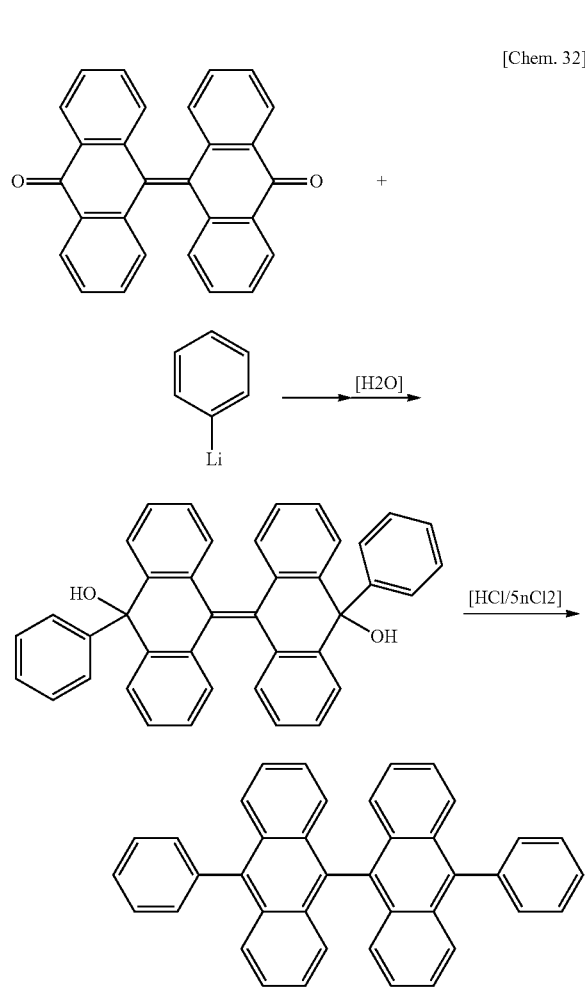

[Chem. 32]

Synthesis (C2-1)

Under an Ar atmosphere, 5 g of bianthrone and 150 ml of dry diethyl ether were placed in a 300 ml flask. 5.5 ml of commercially available phenyllithium reagent (19% butyl ether solution) was added thereto and the mixture was stirred for 3 hours at room temperature. Then, after 10 ml of water was introduced, the mixture was transferred to a separatory funnel and the object was extracted in toluene, dried, separated and purified using silica gel ($SiO_2$, 500 g).

As a result, 5 g of a white substance (10,10'-diphenyl-10H,10'H-[9,9']bianthracenylidene-10,10'-diol) was obtained.

Synthesis (C2-2)

5 g of diol product obtained from synthesis (C2-1) and 300 ml of acetic acid were placed in a 500 ml flask. 5 g of tin chloride (II) (anhydrous) dissolved in 5 g of hydrochloric acid (35%) was added thereto and the mixture was stirred for 30 minutes. After that, the mixture was transferred to a separatory funnel, separated and washed in distilled water by adding toluene and was dried. The solid obtained was purified with silica-gel ($SiO_2$ 500 g) resulting in 5.5 g of pale yellow solid (a compound expressed by the Formula H2-61).

(Synthesis Example C3) Synthesis of a Compound Expressed by Formula H2-66

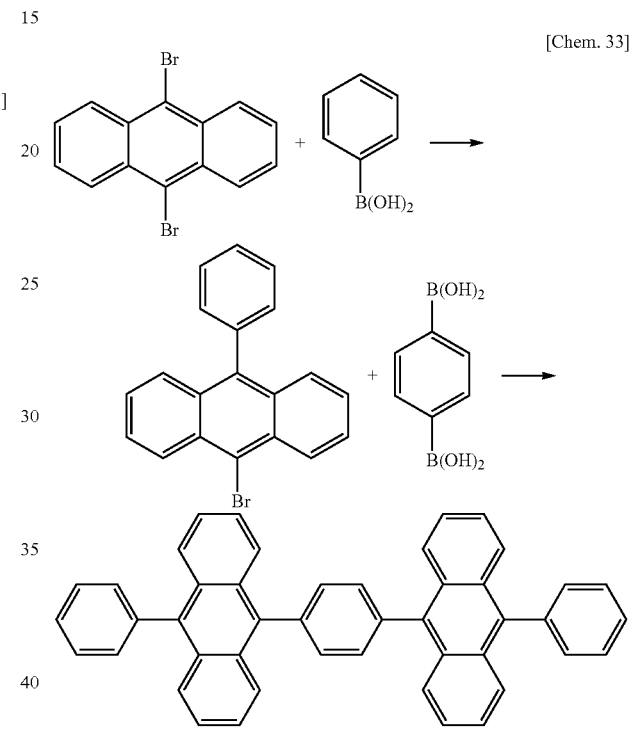

[Chem. 33]

Synthesis (C3-1)

2.2 g of commercially available phenylboronic acid and 6 g of 9,10-dibromoanthracene were dissolved in 100 ml of dimethoxyethane and were heated to 80° C. 50 ml of distilled water and 10 g of sodium carbonate were added thereto. Also, 0.5 g of tetrakis-triphenylphosphine palladium (0) was added thereto.

After 3 hours, extraction with toluene was carried out in a separatory funnel and purification using silica gel ($SiO_2$, 500 g) was carried out.

As a result, 4 g of pale yellow crystals (9-bromo-10-phenylanthracene) was obtained.

Synthesis (C3-2) Under an Ar atmosphere, in a 500 ml flask, 4 g of 9-bromo-10-phenylanthracene obtained from synthesis (C3-1) and 0.8 g of commercially available phenylenediboronic acid were dissolved in 200 ml of dimethoxyethane and were heated to 80° C. 250 ml of distilled water and 10 g of sodium carbonate were added thereto. Also, 0.5 g of tetrakis-triphenylphosphine palladium(0) was placed thereto.

After 3 hours, extraction with toluene was carried out in a separatory funnel and purification using silica gel chromatography was carried out.

As a result, 2 g of pale yellow solid (a compound expressed by the Formula H2-66) was obtained.

4. Production of Electron Transporting Material (Azaindolizine-Based Compound)

(Synthesis Example D1) Synthesis of a Compound Expressed by Formula ETL-A3 was heated and dissolved in 1 liter of methanol, and after the insoluble impurities were removed by filtration, concentrated and precipitated resultant was recovered.

As a result, 8 g of a target compound as white solid (2-(4-bromophenyl)-imidazo[1,2-a]pyridine) was obtained.

[Chem. 34]

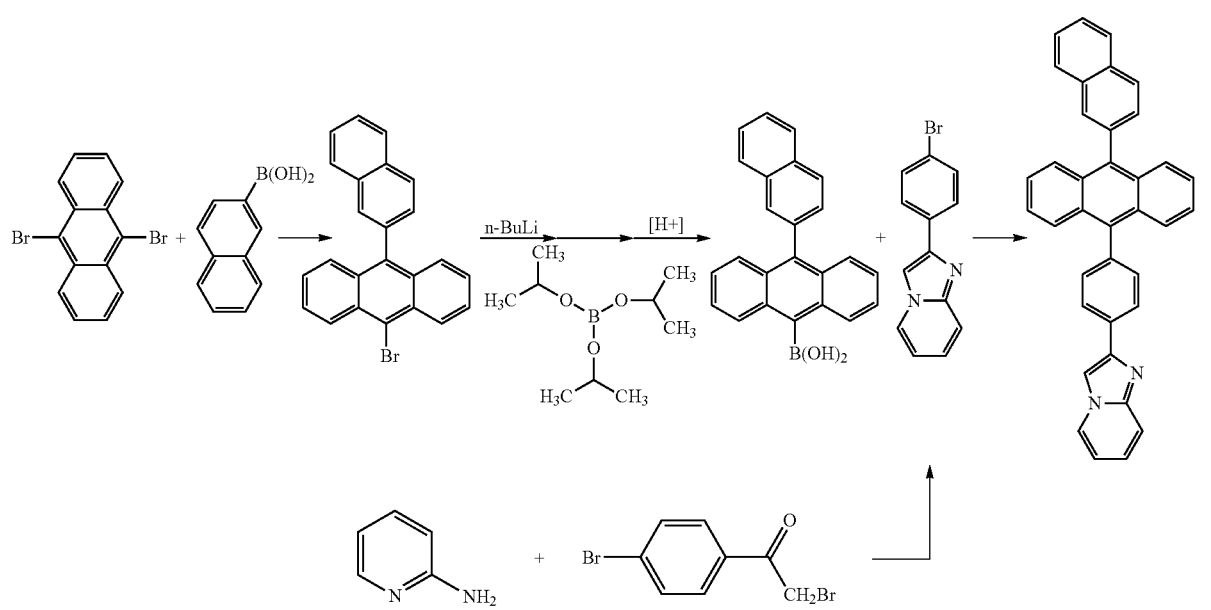

Synthesis (D1-1)

2.1 g of commercially available 2-naphthaleneboronic acid and 5 g of 9,10-dibromoanthracene were dissolved in 50 ml of dimethoxyethane and were heated to 80° C. 50 ml of distilled water and 10 g of sodium carbonate were added thereto. Also, 0.4 g of tetrakis-triphenylphosphine palladium (0) was added thereto.

After 3 hours, extraction with toluene was carried out in a separatory funnel and purification using silica gel (SiO$_2$, 500 g) was carried out.

As a result, 3 g of pale yellow crystal (9-bromo-10-naphthalen-2-yl-anthracene) was obtained.

Synthesis (D1-2)

Under an Ar atmosphere, 3 g of 9-bromo-10-naphthalen-2-yl-anthracene obtained from synthesis (D1-1) and 500 ml of dehydrated tetrahydrofuran were placed in a 1 liter flask, and 6 ml of 1.6 M n-BuLi/hexane solution was added dropwise over 10 minutes at −60° C. After 30 minutes, 1.5 g of triisopropyl borate was added. After the dropwise addition, it was allowed to react for 3 hours at ambient temperature. After the reaction, 50 mL of distilled water was added dropwise, and after that, the mixture was extracted and the liquid was separated using 1 liter of toluene. The organic layer was concentrated, recrystallized, filtered, dried and 2 g of a white substance (boronic acid product) was obtained.

Synthesis (D1-3)

Under an Ar atmosphere, into a 300 ml flask, 3.4 g of 2-aminopyridine was weighed, and 40 ml of ethanol and 40 mL of acetone were added thereto and were dissolved. 10 g of 4-bromophenacyl bromide was added thereto and was heated under reflux. After 3 hours, heating was stopped and the mixture was cooled to room temperature. After the solvent was removed under reduced pressure, the mixture Synthesis (D1-4)

Under an Ar atmosphere, in a 500 ml flask, 2 g of boronic acid product obtained from synthesis (D1-2) and 1.7 g of imidazopyridine derivative obtained from synthesis (D1-3) were dissolved in 200 ml of dimethoxyethane and were heated to 80° C. 250 ml of distilled water and 10 g of sodium carbonate were added thereto. Also, 0.5 g of tetrakis-triphenylphosphine palladium(0) was added thereto.

After 3 hours, extraction with toluene was carried out in a separatory funnel and purification using silica gel (SiO$_2$, 500 g) was carried out.

As a result, 2 g of white solid (a compound expressed by the Formula ETL-A3) was obtained.

5. Production of Light Emitting Element

Example 1-1

<1> First, a transparent glass substrate with average thickness of 0.5 mm was prepared. Next, on the substrate, an ITO electrode (anode) with average thickness of 100 nm was formed by a sputtering method.

Next, the substrate was immersed in acetone and 2-propanol in that order, was cleaned by ultrasonic waves, and was subjected to an oxygen plasma treatment and an argon plasma treatment. These plasma treatments were performed with 100 W of plasma power, 20 sccm of gas flow, and 5 seconds of treatment time while the substrate was kept warm at 70 to 90° C.

<2> Next, on the ITO electrode, tetrakis-p-biphenyl-benzidine (the compound represented by following Formula HTL-1) was deposited using a vacuum deposition method as an amine-based hole transporting material, and a hole transport layer with average thickness of 50 nm was formed.

[Chem. 35]

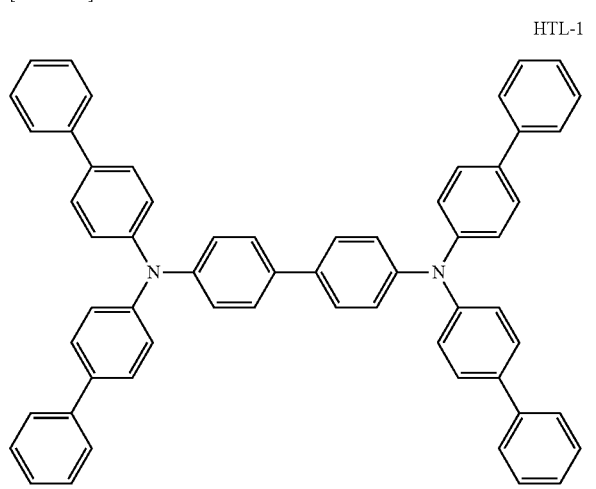

HTL-1

<3> Next, on the hole transport layer, a component material for a light emitting layer was deposited using a vacuum deposition method, and the light emitting layer with an average thickness of 25 nm was formed. As a component material for the light emitting layer, the compound represented by the Formula D-2 was used as a light emitting material (guest material) and the compound represented by the Formula H1-2 (tetracene-based material) was used as a host material. Also, a content of the light emitting material (dopant) in the light emitting layer (doping concentration) was 4.0 wt %.

<4> Next, on the light emitting layer, 2,9-dimethyl-4,7-diphenyl-1,10-phenanthroline (BCP) was formed as a film using a vacuum deposition method, and an electron transport layer with average thickness of 80 nm was formed.

<5> Next, on the electron transport layer, lithium fluoride (LiF) was formed as a film using a vacuum deposition method, and an electron injection layer with average thickness of 1 nm was formed.

<6> Next, on the electron injection layer, Al was formed as a film using a vacuum deposition method. A cathode consisted of Al with average thickness of 100 nm was formed from this process.

<7> Next, a protecting cover (sealing member) made of glass was used for covering so as to cover each layer formed, and epoxy resin was used for fixing and sealing.

From these processes, a light emitting element was prepared.

Example 1-2

The light emitting element was prepared in the same manner as that of Example 1-1 described above, except that the compound represented by the Formula H1-5 (the tetracene-based material) was used as the host material of the light emitting layer.

Example (1-3)

The light emitting element was prepared in the same manner as that of Example 1-1 described above, except that the compound represented by the Formula H1-13 (the tetracene-based material) was used as the host material of the light emitting layer.

Example 1-4

The light emitting element was prepared in the same manner as that of Example 1-1 described above, except that a content of the light emitting material (dopant) in the light emitting layer (doping concentration) was 1.0 wt %.

Example 1-5

The light emitting element was prepared in the same manner as that of Example 1-1 described above, except that a content of the light emitting material (dopant) in the light emitting layer (doping concentration) was 2.0 wt %.

Example 1-6

The light emitting element was prepared in the same manner as that of Example 1-1 described above, except that a content of the light emitting material (dopant) in the light emitting layer (doping concentration) was 10.0 wt %.

Example 1-7

The light emitting element was prepared in the same manner as that of Example 1-1 described above, except that, along with an average thickness of the light emitting layer being 15 nm, an average thickness of the electron transport layer was 90 nm.

Example 1-8

The light emitting element was prepared in the same manner as that of Example 1-1 described above, except that, along with an average thickness of the light emitting layer being 50 nm, an average thickness of the electron transport layer was 55 nm.

Example 1-9

The light emitting element was prepared in the same manner as that of Example 1-1 described above, except that, along with an average thickness of the light emitting layer being 70 nm, an average thickness of the electron transport layer was 35 nm.

Example 1-10

The light emitting element was prepared in the same manner as that of Example 1-1 described above, except that the compound represented by the Formula D-1 was used as the light emitting material of the light emitting layer.

Example 1-11

The light emitting element was prepared in the same manner as that of Example 1-1 described above, except that the compound represented by the Formula D-3 was used as the light emitting material of the light emitting layer.

Comparative Example 1-1

The light emitting element was prepared in the same manner as that of Example 1-1 described above, except that $Alq_3$ was used as the host material of the light emitting layer.

Example 2-1

The light emitting element was prepared in the same manner as that of Example 1-1 described above, except that the compound represented by the Formula H2-34 (the anthracene-based material) was used as the host material of the light emitting layer.

Example 2-2

The light emitting element was prepared in the same manner as that of Example 2-1 described above, except that the compound represented by the Formula H2-61 (the anthracene-based material) was used as the host material of the light emitting layer.

Example 2-3

The light emitting element was prepared in the same manner as that of Example 2-1 described above, except that the compound represented by the Formula H2-66 (the anthracene-based material) was used as the host material of the light emitting layer.

Example 2-4

The light emitting element was prepared in the same manner as that of Example 2-1 described above, except that a content of the light emitting material (dopant) in the light emitting layer (doping concentration) was 1.0 wt %.

Example 2-5

The light emitting element was prepared in the same manner as that of Example 2-1 described above, except that a content of the light emitting material (dopant) in the light emitting layer (doping concentration) was 2.0 wt %.

Example 2-6

The light emitting element was prepared in the same manner as that of Example 2-1 described above, except that a content of the light emitting material (dopant) in the light emitting layer (doping concentration) was 10.0 wt %.

Example 2-7

The light emitting element was prepared in the same manner as that of Example 2-1 described above, except that, along with an average thickness of the light emitting layer being 15 nm, an average thickness of the electron transport layer was 90 nm.

Example 2-8

The light emitting element was prepared in the same manner as that of Example 2-1 described above, except that, along with an average thickness of the light emitting layer being 50 nm, an average thickness of the electron transport layer was 55 nm.

Example 2-9

The light emitting element was prepared in the same manner as that of Example 2-1 described above, except that, along with an average thickness of the light emitting layer being 70 nm, an average thickness of the electron transport layer was 35 nm.

Example 2-10

The light emitting element was prepared in the same manner as that of Example 2-1 described above, except that the compound represented by the Formula D-1 was used as the light emitting material of the light emitting layer.

Example 2-11

The light emitting element was prepared in the same manner as that of Example 2-1 described above, except that the compound represented by the Formula D-3 was used as the light emitting material of the light emitting layer.

Comparative Example 2-1

The light emitting element was prepared in the same manner as that of Example 2-1 described above, except that $Alq_3$ was used as the host material of the light emitting layer.

Example 3-1

The light emitting element was prepared in the same manner as that of Example 1-1 described above, except that tris(8-quinolinolato)aluminum ($Alq_3$) was used as the host material of the light emitting layer and the compound represented by the Formula ETL-A3 (the azaindolizine-based compound) was used in the electron transport layer.

Example 3-2

The light emitting element was prepared in the same manner as that of Example 3-1 described above, except that the compound represented by the Formula H1-5 (the tetracene-based material) was used as the host material of the light emitting layer.

Example 3-3

The light emitting element was prepared in the same manner as that of Example 3-1 described above, except that the compound represented by the Formula H1-13 (the tetracene-based material) was used as the host material of the light emitting layer.

Example 3-4

The light emitting element was prepared in the same manner as that of Example 3-1 described above, except that, along with the compound represented by the Formula H1-5 (the tetracene-based material) being used as the host material of the light emitting layer, an average thickness of the light emitting layer was 45 nm and an average thickness of the electron transport layer was 60 nm.

Example 3-5

The light emitting element was prepared in the same manner as that of Example 3-1 described above, except that, along with the compound represented by the Formula H1-5 (the tetracene-based material) being used as the host material of the light emitting layer, an average thickness of the light emitting layer was 15 nm and an average thickness of the electron transport layer was 90 nm.

Example 3-6

The light emitting element was prepared in the same manner as that of Example 3-1 described above, except that the compound represented by the Formula H1-5 (the tetracene-based material) was used as the host material of the light emitting layer and also the electron transport layer was formed from stacking Alq$_3$ and the compound represented by the Formula ETL-A3 in this order using a vapor deposition method.

Here, in the electron transport layer, an average thickness of the layer made of Alq$_3$ was 20 nm and an average thickness of the layer made of the compound represented by the Formula ETL-A3 was 60 nm.

Example 3-7

The light emitting element was prepared in the same manner as that of Example 3-1 described above, except that the compound represented by the Formula H1-5 (the tetracene-based material) was used as the host material of the light emitting layer and also the electron transport layer was formed from stacking the compound represented by the Formula H1-5, Alq$_3$, and the compound represented by the Formula ETL-A3 in this order using a vapor deposition method.

Here, an average thickness of the light emitting layer was 35 nm. Also, in the electron transport layer, an average thickness of the layer made of the compound represented by the Formula H1-5 was 20 nm, an average thickness of the layer made of Alq$_3$ was 20 nm and an average thickness of the layer made of the compound represented by the Formula ETU-A3 was 30 nm.

Example 3-8

The light emitting element was prepared in the same manner as that of Example 3-1 described above, except that the compound represented by the Formula D-1 was used as the light emitting material of the light emitting layer and the compound represented by the Formula H1-5 (the tetracene-based material) was used as the host material of the light emitting layer.

Example 3-9

The light emitting element was prepared in the same manner as that of Example 3-1 described above, except that the compound represented by the Formula D-3 was used as the light emitting material of the light emitting layer and the compound represented by the Formula H1-5 (the tetracene-based material) was used as the host material of the light emitting layer.

Comparative Example 3-1

The light emitting element was prepared in the same manner as that of Example 3-1 described above, except that 2,9-dimethyl-4,7-diphenyl-1,10-phenanthroline (BCP) was used as the electron transporting material of the electron transport layer.

Reference Example 1

The light emitting element was prepared in the same manner as that of Example 3-1 described above, except that, along with the compound represented by the Formula H1-5 (the tetracene-based material) being used as the host material of the light emitting layer and 2,9-dimethyl-4,7-diphenyl-1,10-phenanthroline (BCP) being used as the electron transporting material of the electron transport layer, an average thickness of the light emitting layer was 45 nm and an average thickness of the electron transport layer was 60 nm.

Reference Example 2

The light emitting element was prepared in the same manner as that of Example 3-1 described above, except that, along with the compound represented by the Formula H1-5 (the tetracene-based material) being used as the host material of the light emitting layer and 2,9-dimethyl-4,7-diphenyl-1,10-phenanthroline (BCP) being used as the electron transporting material of the electron transport layer, an average thickness of the light emitting layer was 15 nm and an average thickness of the electron transport layer was 90 nm.

Reference Example 3

The light emitting element was prepared in the same manner as that of Example 3-1 described above, except that the compound represented by the Formula H1-5 (the tetracene-based material) was used as the host material of the light emitting layer and also the electron transport layer was formed from stacking Alq$_3$ and BCP in this order using a vapor deposition method.

Here, in the electron transport layer, an average thickness of the layer made of Alq$_3$ was 20 nm and an average thickness of the layer made of BCP was 60 nm.

Reference Example 4

The light emitting element was prepared in the same manner as that of Example 3-1 described above, except that the compound represented by the Formula H1-5 (the tetracene-based material) was used as the host material of the light emitting layer and also the electron transport layer was formed from stacking the compound represented by the Formula H1-5, Alq$_3$, and BCP in this order using a vapor deposition method.

Here, an average thickness of the light emitting layer is 35 nm. Also, in the electron transport layer, an average thickness of the layer made of the compound represented by the Formula H1-5 was 20 nm an average thickness of the layer made of Alq$_3$ was 20 nm and an average thickness of the layer made of BCP was 30 nm.

Reference Example 5

The light emitting element was prepared in the same manner as that of Example 3-1 described above, except that the compound represented by the Formula H1-5 (the tetracene-based material) was used as the host material of the light emitting layer and Alq$_3$ was used as the electron transporting material of the electron transport layer.

Reference Example 6

The light emitting element was prepared in the same manner as that of Example 3-1 described above, except that the compound represented by the Formula D-1 was used as the light emitting material of the light emitting layer, the compound represented by the Formula H1-5 (the tetracene-based material) was used as the host material of the light emitting layer, and BCP was used as the electron transporting material of the electron transport layer.

Reference Example 7

The light emitting element was prepared in the same manner as that of Example 3-1 described above, except that the compound represented by Formula D-3 was used as the light emitting material of the light emitting layer, the compound represented by Formula H1-5 (the tetracene-based material) was used as the host material of the light emitting layer, and ECP was used as the electron transporting material of the electron transport layer.

6. Evaluation For each of the examples and the comparative example, a constant current of 100 mA/cm² was flowing to the light emitting element using a constant current power (KEITHLEY 2400, manufactured by TOYO Technica Co., Ltd.) and the light emitting peak wavelength at the time was measured using a spectral emission brightness meter (CS-2000, manufactured by Konica Minolta Sensing Co., Ltd.). Light emitting power was measured using an optical power measuring device (optical power meter 8230, manufactured by ADC Co., Ltd.). Also, for the measurement of light emitting peak wavelength and light emitting power in Examples 1-11, 2-11, and 3-9 and Reference Example 7, S2000 manufactured by Ocean Optics, Inc. was used.

Also, the voltage value (driving voltage) at the time was measured.

In addition, the time for the brightness to become 80% of the initial brightness (LT80) was measured.

Figure 5:
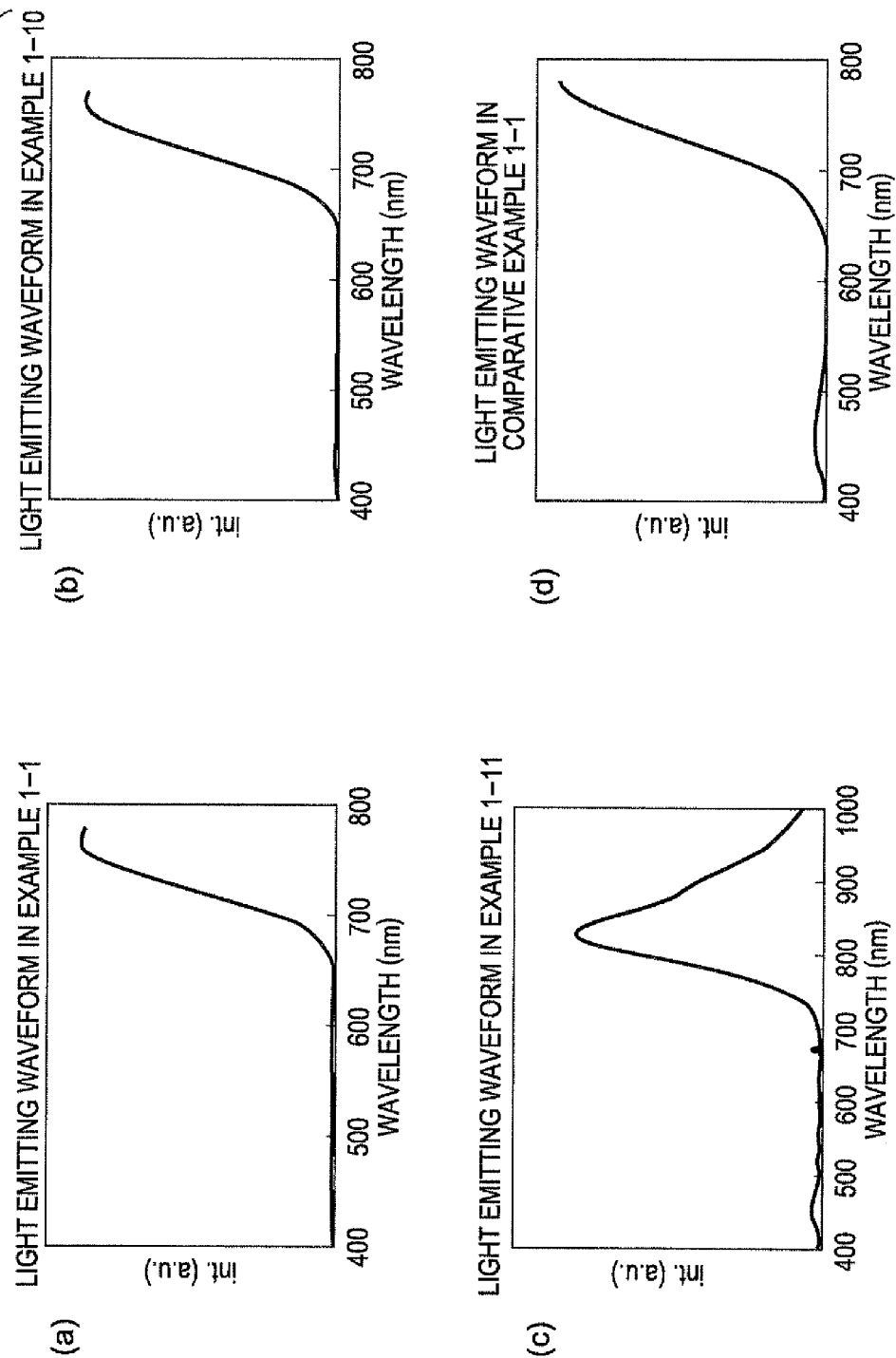
FIG. 5 are diagrams which show light emission spectra of a light emitting element in Examples (Examples 1-1, 1-10, 1-11) and the Comparative Example 1-1 according to an embodiment of the present invention.
Figure 6:
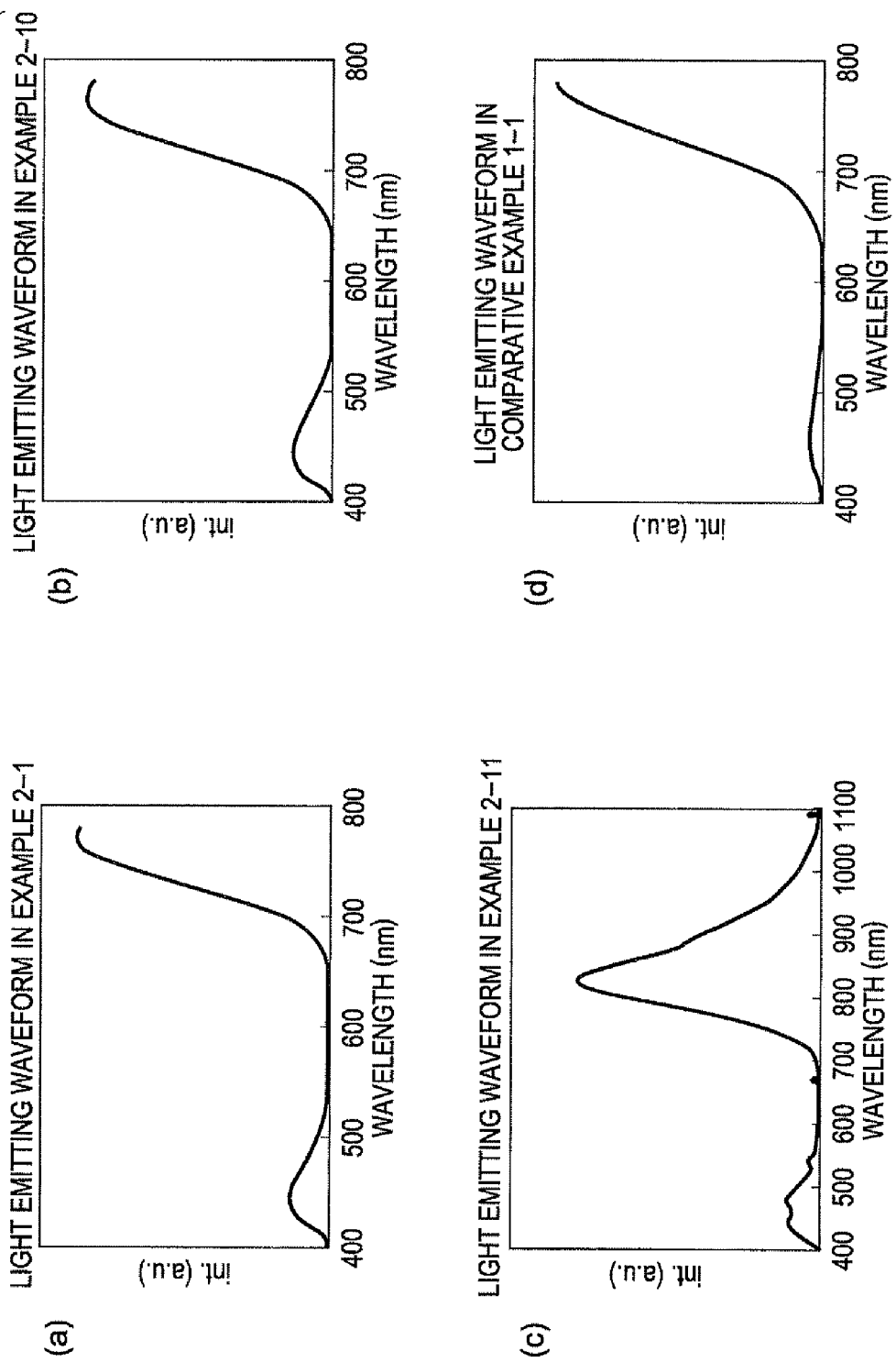
FIG. 6 are diagrams which show light emission spectra of a light emitting element in Examples (Examples 2-1, 2-10, 2-11) and the Comparative Example 2-1 according to an embodiment of the present invention.
Figure 7:
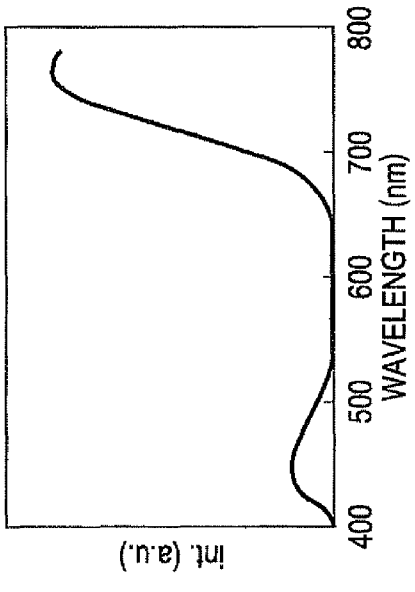
FIG. 7 are diagrams which show light emission spectra of a light emitting element in Examples (Examples 3-2, 3-8, 3-9) and the Comparative Example 3-1 according to an embodiment of the present invention.
Figure 7:
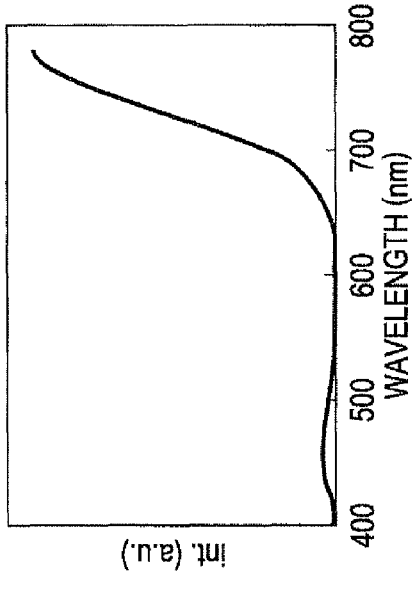
Figure 7:
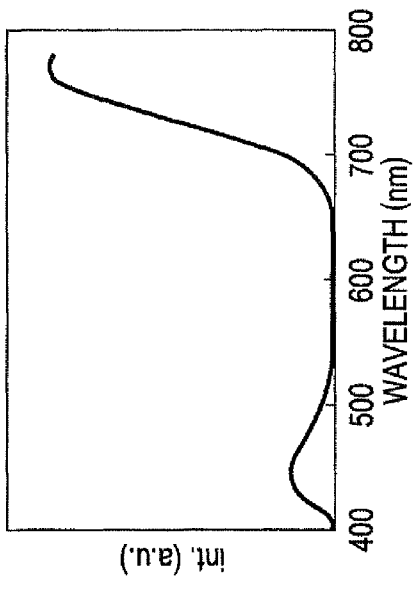
Figure 7:
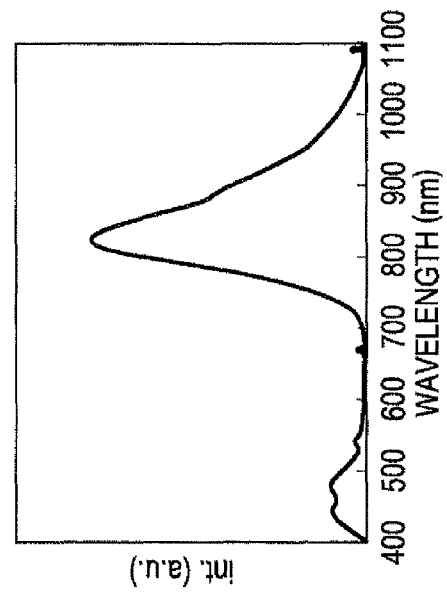

These measurement results are shown in Table 1, Table 2 and Table 3. Also, light emission spectra of the light emitting element in Examples 1-1, 1-10, and 1-11 and the Comparative Example 1-1 are shown in FIG. 5, light emission spectra of the light emitting element in Examples 2-1, 2-10, and 2-11 and the Comparative Example 2-1 are shown in FIG. 6, and light emission spectra of the light emitting element in Examples 3-2, 3-8, and 3-9 and the Comparative Example 3-1 are shown in FIG. 7.

TABLE 1

| | Light emitting layer | | | | Electron transport layer | | Evaluation | | | |
|---|---|---|---|---|---|---|---|---|---|---|
| | Light emitting material | Host material | Concentration of light emitting material [w %] | Average thickness [nm] | Material | Average thickness [nm] | Light emitting peak wavelength [nm] | Light emitting power [mW/cm²] | Voltage [V] | LT80 [hr] |
| Example 1-1 | D-2 | H1-2 | 4 | 25 | BCP | 80 | 770 | 4.5 | 5.5 | 100 |
| Example 1-2 | D-2 | H1-5 | 4 | 25 | BCP | 80 | 770 | 4.6 | 5.5 | 120 |
| Example 1-3 | D-2 | H1-13 | 4 | 25 | BCP | 80 | 770 | 4.8 | 5.6 | 90 |
| Example 1-4 | D-2 | H1-2 | 1 | 25 | BCP | 80 | 760 | 4.8 | 5.3 | 110 |
| Example 1-5 | D-2 | H1-2 | 2 | 25 | BCP | 80 | 765 | 4.7 | 5.2 | 100 |
| Example 1-6 | D-2 | H1-2 | 10 | 25 | BCP | 80 | 775 | 4.2 | 5.7 | 100 |
| Example 1-7 | D-2 | H1-2 | 4 | 15 | BCP | 90 | 770 | 4.5 | 5.2 | 80 |
| Example 1-8 | D-2 | H1-2 | 4 | 50 | BCP | 55 | 770 | 4.4 | 5.7 | 110 |
| Example 1-9 | D-2 | H1-2 | 4 | 70 | BCP | 35 | 770 | 4.3 | 5.8 | 110 |
| Example 1-10 | D-1 | H1-2 | 4 | 25 | BCP | 80 | 760 | 4.5 | 5.3 | 110 |
| Example 1-11 | D-3 | H1-2 | 4 | 25 | BCP | 80 | 820 | 3.7 | 5.5 | 100 |
| Comparative Example 1-1 | D-2 | Alq | 4 | 25 | BCP | 80 | 780 | 0.9 | 6.4 | 30 |

TABLE 2

| | Light emitting layer | | | | Electron transport layer | | Evaluation | | | |
|---|---|---|---|---|---|---|---|---|---|---|
| | Light emitting material | Host material | Concentration of light emitting material [w %] | Average thickness [nm] | Material | Average thickness [nm] | Light emitting peak wavelength [nm] | Light emitting power [mW/cm²] | Voltage [V] | LT80 [hr] |
| Example 2-1 | D-2 | H2-34 | 4 | 25 | BCP | 80 | 770 | 2.2 | 7 | 400 |
| Example 2-2 | D-2 | H2-61 | 4 | 25 | BCP | 80 | 770 | 2.2 | 6.8 | 330 |
| Example 2-3 | D-2 | H2-66 | 4 | 25 | BCP | 80 | 770 | 2.3 | 7 | 300 |
| Example 2-4 | D-2 | H2-34 | 1 | 25 | BCP | 80 | 760 | 2.4 | 7 | 350 |
| Example 2-5 | D-2 | H2-34 | 2 | 25 | BCP | 80 | 765 | 2.3 | 7 | 380 |
| Example 2-6 | D-2 | H2-34 | 10 | 25 | BCP | 80 | 775 | 2 | 7.3 | 330 |
| Example 2-7 | D-2 | H2-34 | 4 | 15 | BCP | 90 | 770 | 2.2 | 8 | 350 |
| Example 2-8 | D-2 | H2-34 | 4 | 50 | BCP | 55 | 770 | 2.2 | 6.5 | 380 |
| Example 2-9 | D-2 | H2-34 | 4 | 70 | BCP | 35 | 770 | 2.1 | 6.3 | 380 |
| Example 2-10 | D-1 | H2-34 | 4 | 25 | BCP | 80 | 760 | 2.5 | 6.8 | 400 |
| Example 2-11 | D-3 | H2-34 | 4 | 25 | BCP | 80 | 820 | 1.8 | 7.1 | 400 |
| Comparative Example 2-1 | D-2 | Alq | 4 | 25 | BCP | 80 | 780 | 0.9 | 6.4 | 30 |

TABLE 3

| | Light emitting layer | | | | Electron transport layer | | Evaluation | | | |
|---|---|---|---|---|---|---|---|---|---|---|
| | Light emitting material | Host material | Concentration of light emitting material [w %] | Average thickness [nm] | Material | Average thickness [nm] | Light emitting peak wavelength [nm] | Light emitting power [mW/cm²] | Voltage [V] | LT80 [hr] |
| Example 3-1 | D-2 | Alq | 4 | 25 | ETL-A3 | 80 | 780 | 3 | 5 | >1000 |
| Example 3-2 | D-2 | H1-5 | 4 | 25 | ETL-A3 | 80 | 770 | 8.5 | 4.8 | >1000 |
| Example 3-3 | D-2 | H1-13 | 4 | 25 | ETL-A3 | 80 | 770 | 8.8 | 4.8 | >1000 |
| Example 3-4 | D-2 | H1-5 | 4 | 45 | ETL-A3 | 60 | 770 | 8.5 | 5 | >1000 |
| Example 3-5 | D-2 | H1-5 | 4 | 15 | ETL-A3 | 90 | 770 | 8.1 | 4.8 | >1000 |
| Example 3-6 | D-2 | H1-5 | 4 | 25 | Alq ETL-A3 | 20 60 | 770 | 8.5 | 6 | >1000 |
| Example 3-7 | D-2 | H1-5 | 4 | 35 | H1-5 Alq ETL-A3 | 20 20 30 | 770 | 8.2 | 6.1 | >1000 |
| Example 3-8 | D-1 | H1-5 | 4 | 25 | ETL-A3 | 80 | 760 | 8.8 | 5 | >600 |
| Example 3-9 | D-3 | H1-5 | 4 | 25 | ETL-A3 | 80 | 820 | 5 | 4.8 | >600 |
| Comparative Example 3-1 | D-2 | Alq | 4 | 25 | BCP | 80 | 780 | 2 | 9.4 | 30 |
| Reference Example 1 | D-2 | H1-5 | 4 | 45 | BCP | 60 | 770 | 5.8 | 9.3 | 40 |
| Reference Example 2 | D-2 | H1-5 | 4 | 15 | BCP | 90 | 770 | 5.8 | 10 | 40 |
| Reference Example 3 | D-2 | H1-5 | 4 | 25 | Alq BCP | 20 60 | 770 | 5.2 | 10.5 | 60 |
| Reference Example 4 | D-2 | H1-5 | 4 | 35 | H1-5 Alq BCP | 20 20 30 | 770 | 5.5 | 10 | 60 |
| Reference Example 5 | D-2 | H1-5 | 4 | 25 | Alq | 80 | 770 | 6 | 11 | 70 |
| Reference Example 6 | D-1 | H1-5 | 4 | 25 | BCP | 80 | 760 | 6.2 | 9.5 | 40 |
| Reference Example 7 | D-3 | H1-5 | 4 | 25 | BCP | 80 | 820 | 3 | 9.5 | 40 |

As is apparent from Table 1, it was possible that the light emitting element in Examples 1-1 to 1-11 gain high light emitting power compared with the light emitting element in the Comparative Example 1-1, along with emitting light in a near-infrared region. Also, it was possible that the light emitting element in Examples 1-1 to 1-11 suppress the driving voltage compared with the light emitting element in the Comparative Example 1-1. Therefore it was found that the light emitting element in Examples 1-1 to 1-11 had excellent light emitting efficiency.

Also, the light emitting element in Examples 1-1 to 1-11 has longer life compared with the light emitting element in the Comparative Example 1-1.

As is apparent from Table 2, it was possible that the light emitting element in Examples 2-1 to 2-11 gain high light emitting power compared with the light emitting element in the Comparative Example 2-1, along with emitting light in a near-infrared region. Also, it was possible that the light emitting element in Examples 2-1 to 2-11 suppress the driving voltage compared with the light emitting element in the Comparative Example 2-1. Therefore it was found that the light emitting element in Examples 2-1 to 2-11 had excellent light emitting efficiency.

Also, the light emitting element in Examples 2-1 to 2-11 had longer life compared with the light emitting element in the Comparative Example 2-1.

As is apparent from Table 3, it was possible that the light emitting element in Examples 3-1 to 3-9 gain high light emitting power compared with the light emitting element in the Comparative Example 3-1, along with emits light in a near-infrared region. Also, it was possible that the light emitting element in Examples 3-1 to 3-9 suppress the driving voltage compared with the light emitting element in the Comparative Example 3-1 and Reference Examples 1 to 7. Therefore it was found that the light emitting element in Examples 3-1 to 3-9 had excellent light emitting efficiency.

Also, the light emitting element in Example 3-1 to 3-9 had longer life compared with the light emitting element in the Comparative Example 3-1 and Reference Examples 1 to 7.

The present invention contains subject matter related to Japanese Patent Application No. 2011-088559 and Japanese Patent Application No. 2011-088560 and Japanese Patent Application No. 2011-088562 filed in the Japanese Patent Office on Apr. 12, 2011, and the entire contents of which are incorporated herein by reference.

The invention claimed is:

1. A thiadiazole-based compound represented by following Formula (6),

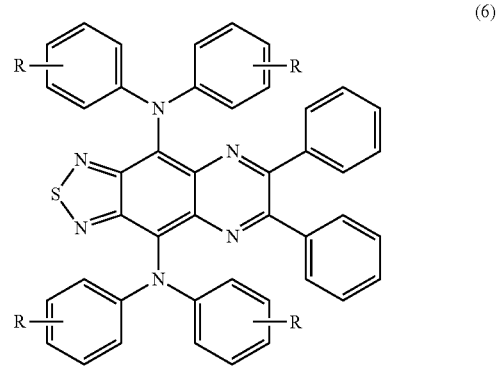

(6)

wherein, in Formula (6), R independently represent a hydrogen atom, an alkyl group, or an aryl group which may have a substituent, adjacent carbons in two Rs may be connected and form a cyclic shape.

2. A light emitting element compound comprising:
the thiadiazole-based compound according to claim 1.

3. A light emitting element comprising:
an anode,
a cathode, and
a light emitting layer that is installed between the anode and the cathode and emits light by applying an electric voltage between the anode and the cathode, wherein
the light emitting element emits light in a near-infrared region,
the light emitting layer comprises a compound represented by following Formula (1) as a light emitting material,

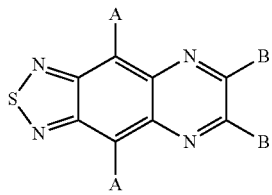
(1)

wherein, in the Formula (1), A independently comprises a diarylamino group, and
each B independently represents a phenyl group, and
the light emitting layer further comprises a compound represented by following Formula IRH-1 as a host material,

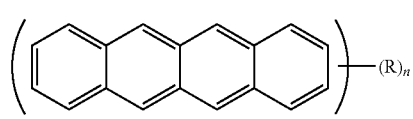
IRH-1 wherein, in the Formula IRH-1,
n represents a natural number of 1 to 12, and
R represents a substituent or a functional group, wherein
each R is independently selected from a hydrogen atom, an alkyl group, an aryl group, or an arylamino group.

4. The light emitting element according to claim 3, wherein the light emitting layer further comprises a compound represented by following Formula IRH-2 as a host material,

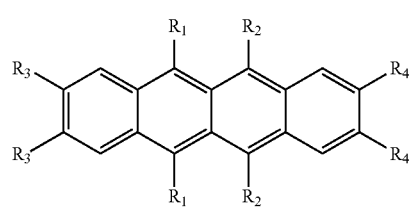
IRH-2 wherein, in the Formula IRH-2, $R_1$ to $R_4$ each independently represent a hydrogen atom, an alkyl group, an aryl group that may have a substituent, or an arylamino group.

5. The light emitting element according to claim 3, wherein the light emitting layer further comprises a compound represented by following Formula IRH-3 as a host material,

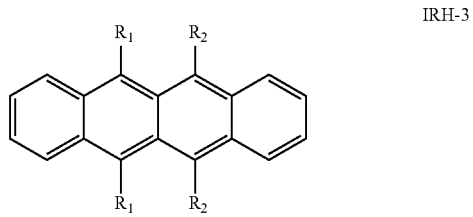
IRH-3 wherein, in the Formula IRH-3, $R_1$ and $R_2$ each independently represent a hydrogen atom, an alkyl group, an aryl group that may have a substituent or an arylamino group.

6. The light emitting element according to claim 3, further comprising:
an electron transport layer that is installed between the anode and the light emitting layer, is in contact with the light emitting layer and has an electron transport property,
wherein the electron transport layer comprises a compound having an azaindolizine skeleton and an anthracene skeleton within a molecule as an electron transporting material.

7. The light emitting element according to claim 6, wherein, as the electron transporting material, the number of the azaindolizine skeletons and the anthracene skeletons included within one molecule is one or two, respectively.

8. The light emitting element according to claim 6, wherein the electron transport layer comprises a first electron transport layer that comprises the compound having the azaindolizine skeleton and the anthracene skeleton within the molecule as a first electron transporting material, and a second electron transport layer that is installed between the first electron transport layer and the light emitting layer, is in contact with both of these layers and comprises a second electron transporting material that is different from the first electron transporting material.

9. A light emitting device comprising:
the light emitting element according to claim 3.

10. An authentication device comprising:
the light emitting element according to claim 3.

11. An electronic device comprising:
the light emitting element according to claim 3.

12. The light emitting element according to claim 3, wherein
the compound represented by Formula IRH-1 is a compound of Formula H1-5 as a host material that contains the light emitting material

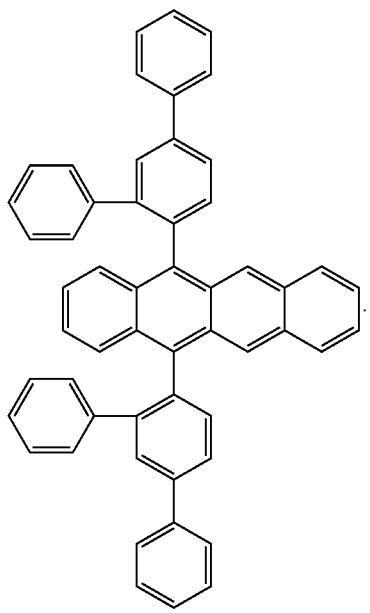

H1-5

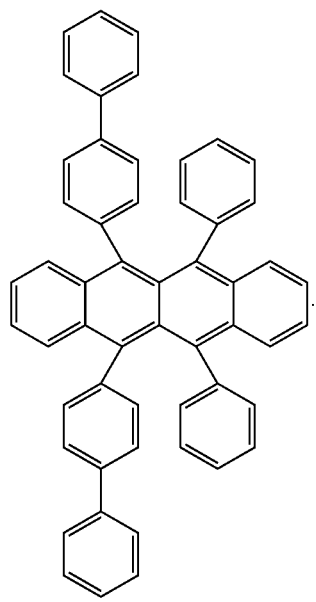

H1-13

15. The light emitting element according to claim 3, wherein
the compound represented by Formula (1) is a compound of Formula D-2 or D-3 as a light emitting material 13. The light emitting element according to claim 3, wherein
the compound represented by Formula IRH-1 is a compound of Formula H1-2 as a host material that contains the light emitting material

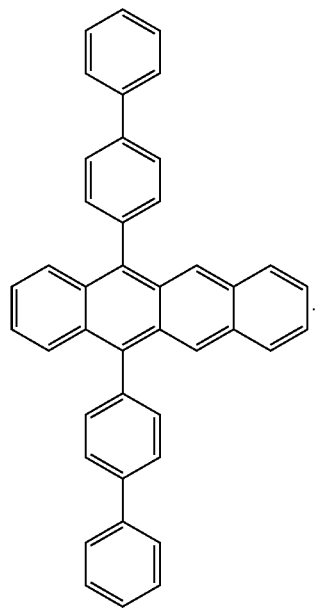

H1-2

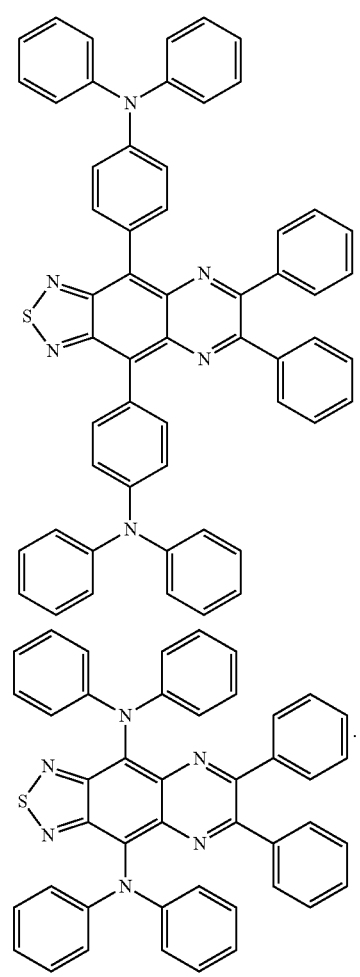

D-2

D-3

14. The light emitting element according to claim 5, wherein
the compound represented by Formula IRH-1 is a compound of Formula H1-13 as a host material that contains the light emitting material

* * * * *